US012285279B2

(12) United States Patent
Subramanyan et al.

(10) Patent No.: US 12,285,279 B2
(45) Date of Patent: Apr. 29, 2025

(54) MOVABLE AND STATIC COLLIMATORS AND X-RAY SOURCE ARRANGEMENTS FOR INTRAORAL TOMOSYNTHESIS

(71) Applicant: CARESTREAM DENTAL LLC, Atlanta, GA (US)

(72) Inventors: Krishnamoorthy Subramanyan, Palatine, IL (US); Vincent Loustauneau, Fontenay sous Bois (FR); Jay S. Schildkraut, Rochester, NY (US); Jean-Marc Inglese, Bussy-Saint-Georges (FR)

( * ) Notice: Subject to any disclaimer, the term of this patent is extended or adjusted under 35 U.S.C. 154(b) by 583 days.

(21) Appl. No.: 17/431,743

(22) PCT Filed: Mar. 11, 2020

(86) PCT No.: PCT/US2020/021974
§ 371 (c)(1),
(2) Date: Aug. 18, 2021

(87) PCT Pub. No.: WO2020/185823
PCT Pub. Date: Sep. 17, 2020

(65) Prior Publication Data
US 2022/0151576 A1    May 19, 2022

Related U.S. Application Data

(60) Provisional application No. 62/817,048, filed on Mar. 12, 2019.

(51) Int. Cl.
*A61B 6/02* (2006.01)
*A61B 6/00* (2006.01)
(Continued)

(52) U.S. Cl.
CPC ............... *A61B 6/025* (2013.01); *A61B 6/06* (2013.01); *A61B 6/08* (2013.01); *A61B 6/4007* (2013.01);
(Continued)

(58) Field of Classification Search
None
See application file for complete search history.

(56) References Cited

U.S. PATENT DOCUMENTS

| 5,416,822 A * | 5/1995 | Kunik | G03B 42/042 378/170 |
| 8,433,033 B2 * | 4/2013 | Harata | A61B 6/583 378/38 |

(Continued)

FOREIGN PATENT DOCUMENTS

| WO | WO-2019038304 A1 * | 2/2019 | ........... A61B 5/0066 |
| WO | WO-2019040056 A1 * | 2/2019 | |

*Primary Examiner* — Thomas R Artman

(57) ABSTRACT

An intraoral tomosynthesis imaging apparatus having an intraoral detector coupled to a frame or radio-opaque marker attached to its radiation facing surface without any frame attached, wherein the frame defines a target aperture for an incident radiation beam. An enclosure seats against the target aperture and houses at least one x-ray source configured to emit a radiation beam from each of a plurality of focal points within the enclosure A collimator is disposed to form a collimated radiation beam and direct the collimated beam through the target aperture and to the detector. A geometric calibration phantom having a plurality of radio-opaque markers is disposed in the path of the collimated beam. This arrangement is modified to operate as a regular intraoral imaging device by accommodating a high-power central source at the same or different distances as other sources from the detector and displacing the phantom from the field of view.

23 Claims, 45 Drawing Sheets

(51) Int. Cl.
*A61B 6/06* (2006.01)
*A61B 6/08* (2006.01)
*A61B 6/40* (2024.01)
*A61B 6/42* (2024.01)
*A61B 6/51* (2024.01)
*A61B 6/58* (2024.01)
*A61B 90/00* (2016.01)

(52) U.S. Cl.
CPC .......... *A61B 6/4085* (2013.01); *A61B 6/4233* (2013.01); *A61B 6/4241* (2013.01); *A61B 6/4452* (2013.01); *A61B 6/512* (2024.01); *A61B 6/5205* (2013.01); *A61B 6/5264* (2013.01); *A61B 6/547* (2013.01); *A61B 6/583* (2013.01); *A61B 6/584* (2013.01); *A61B 6/587* (2013.01); *A61B 90/39* (2016.02); *A61B 2090/3966* (2016.02)

(56) References Cited

U.S. PATENT DOCUMENTS

| | | | |
|---|---|---|---|
| 8,831,322 B2 * | 9/2014 | Abboud | A61B 6/583 |
| | | | 382/128 |
| 9,872,663 B2 * | 1/2018 | Duewer | G06T 5/50 |
| 10,039,508 B2 * | 8/2018 | Abramovich | A61B 6/025 |
| 10,456,097 B2 * | 10/2019 | Kim | A61B 6/145 |
| 10,772,594 B2 * | 9/2020 | Duewer | G06T 11/008 |
| 10,912,530 B2 * | 2/2021 | Mandelkern | G06T 7/12 |
| 11,051,771 B2 * | 7/2021 | Lu | A61B 6/5205 |
| 11,903,752 B2 * | 2/2024 | Inglese | A61B 5/0066 |
| 12,004,890 B2 * | 6/2024 | Capo | A61B 6/022 |
| 12,016,716 B2 * | 6/2024 | Lu | A61B 6/583 |
| 2009/0310845 A1 * | 12/2009 | Ogawa | A61B 6/14 |
| | | | 382/132 |
| 2012/0263363 A1 * | 10/2012 | Abboud | G06T 3/40 |
| | | | 382/131 |
| 2016/0220212 A1 * | 8/2016 | Duewer | G06T 5/005 |
| 2016/0287198 A1 * | 10/2016 | Abramovich | A61B 6/105 |
| 2017/0281110 A1 * | 10/2017 | Mandelkern | A61B 6/5217 |
| 2017/0311911 A1 * | 11/2017 | Kim | A61B 6/032 |
| 2017/0319160 A1 * | 11/2017 | Lu | A61B 6/583 |
| 2019/0175131 A1 * | 6/2019 | Duewer | G06T 11/006 |
| 2020/0337655 A9 * | 10/2020 | Lu | A61B 6/583 |
| 2020/0352530 A1 * | 11/2020 | Inglese | A61B 6/584 |
| 2021/0338180 A1 * | 11/2021 | Lu | A61B 6/14 |
| 2022/0110595 A1 * | 4/2022 | Capo | A61B 6/56 |
| 2022/0151576 A1 * | 5/2022 | Subramanyan | A61B 6/4233 |
| 2022/0330911 A1 * | 10/2022 | Schildkraut | A61B 6/466 |

* cited by examiner

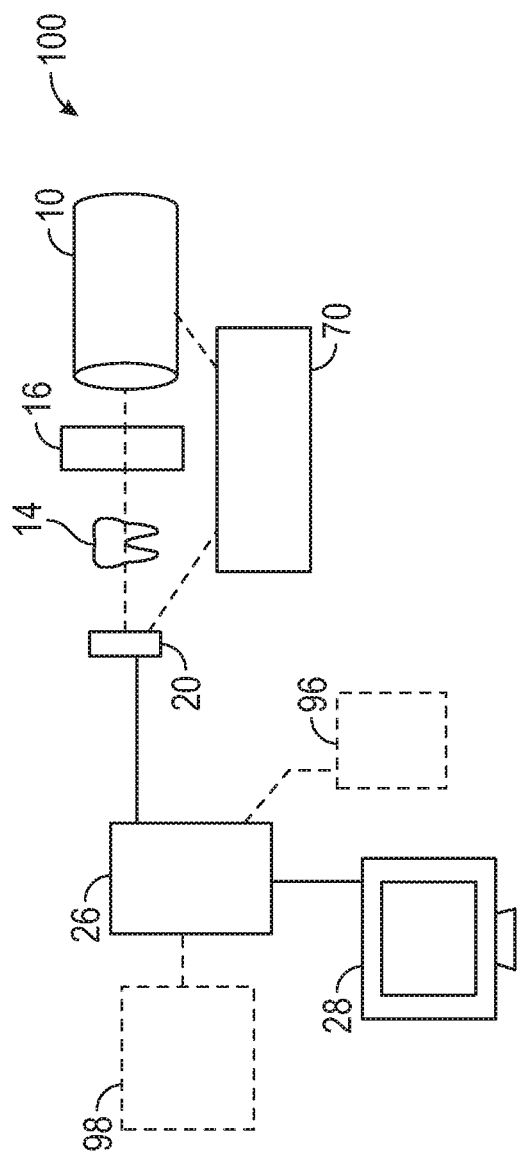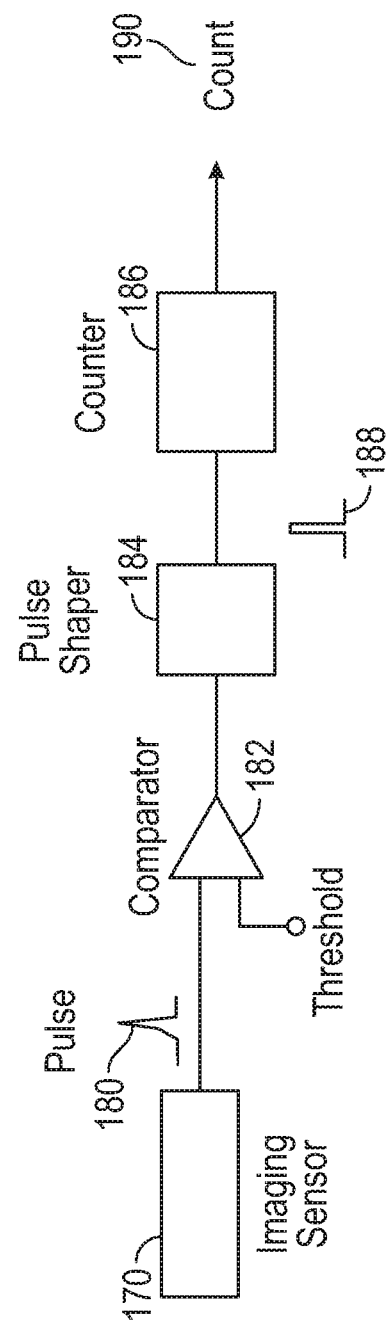

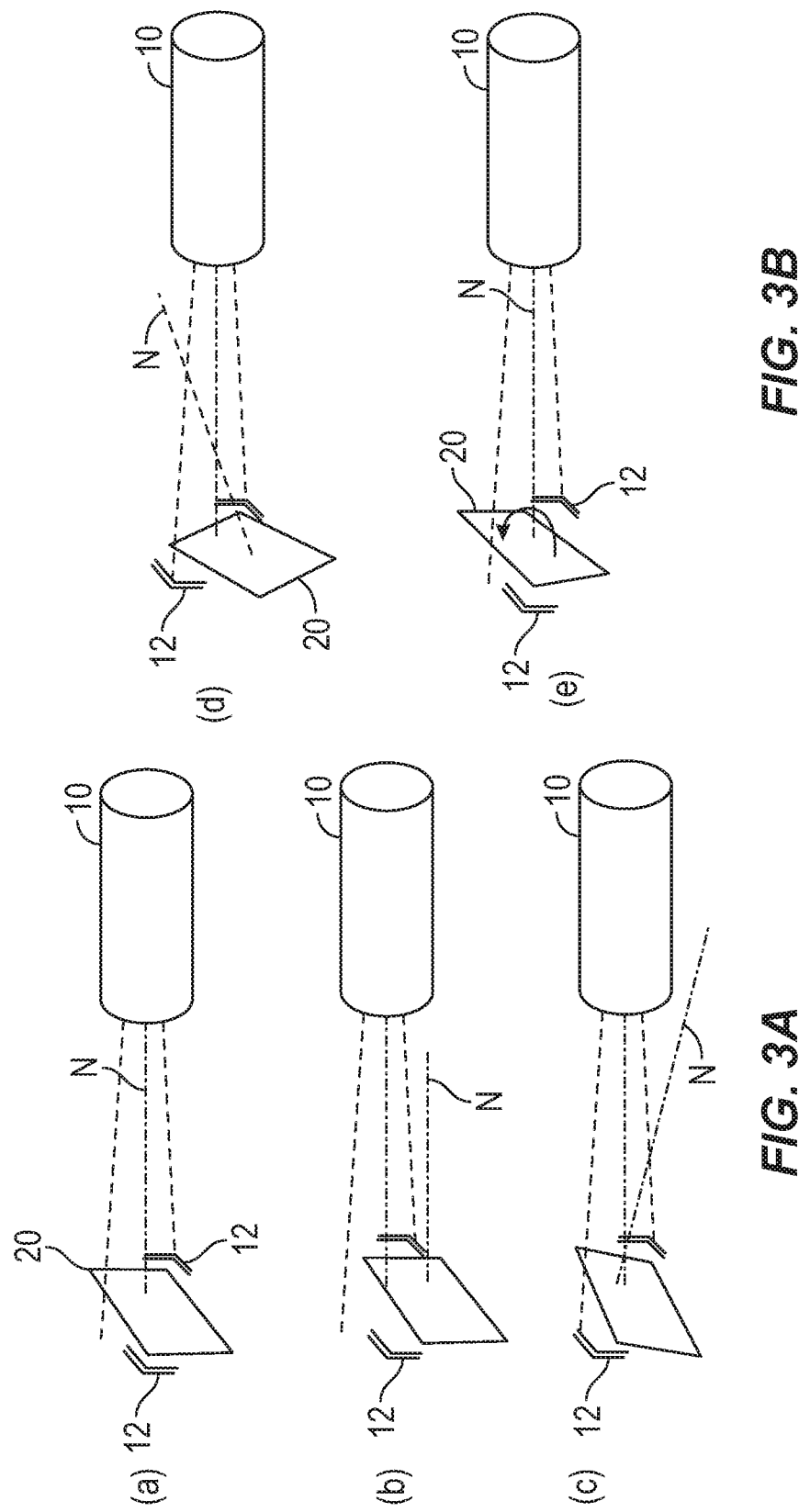

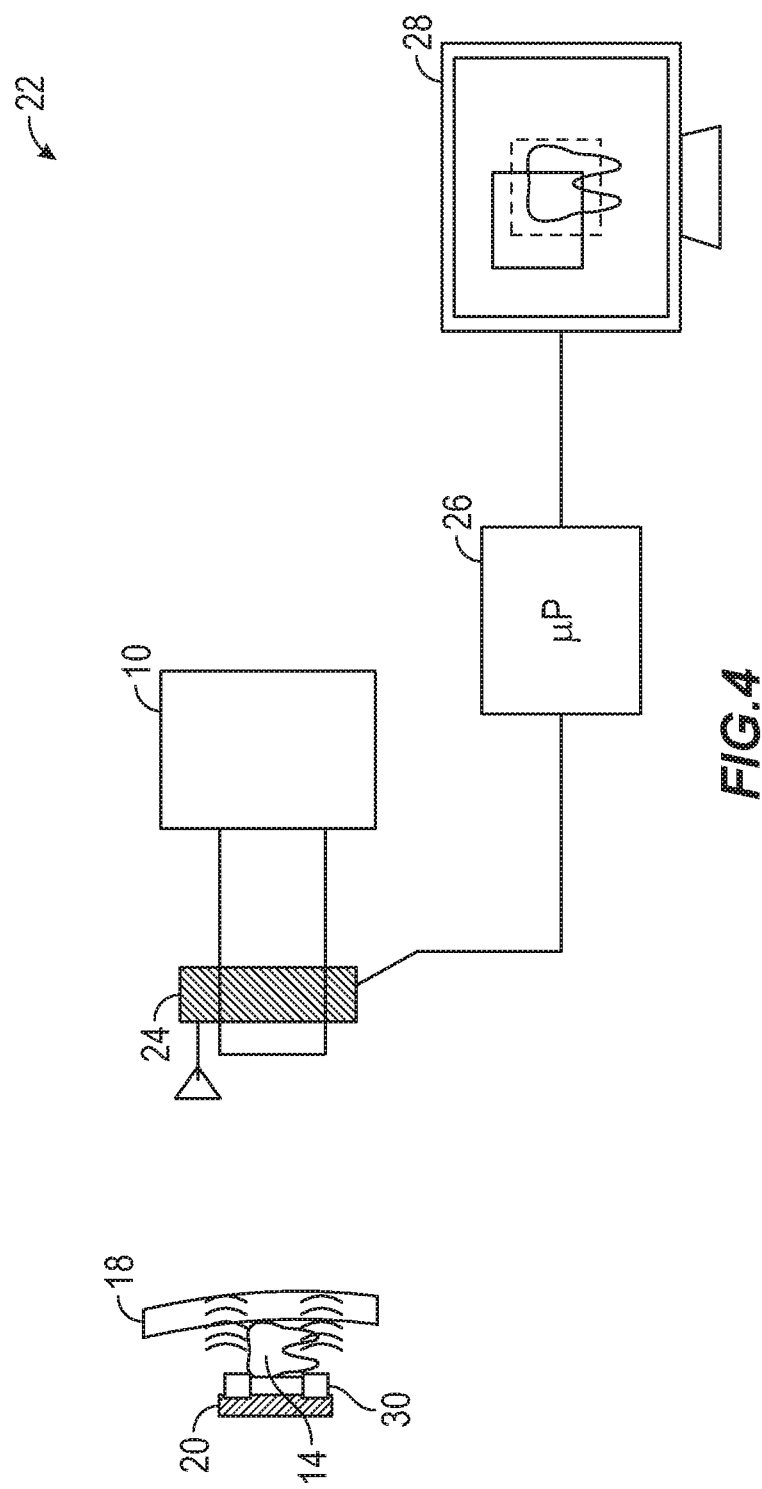

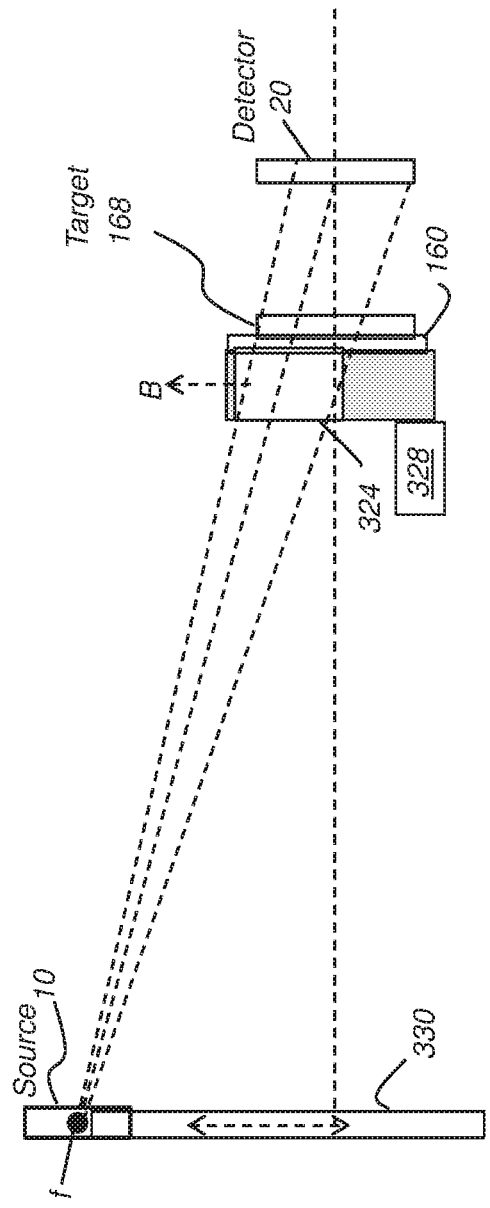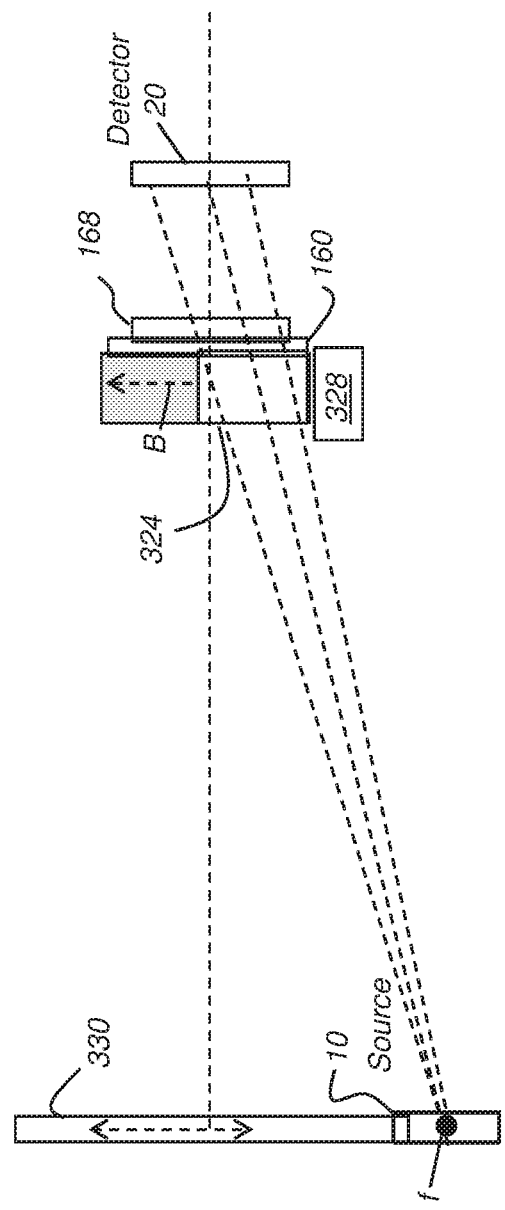

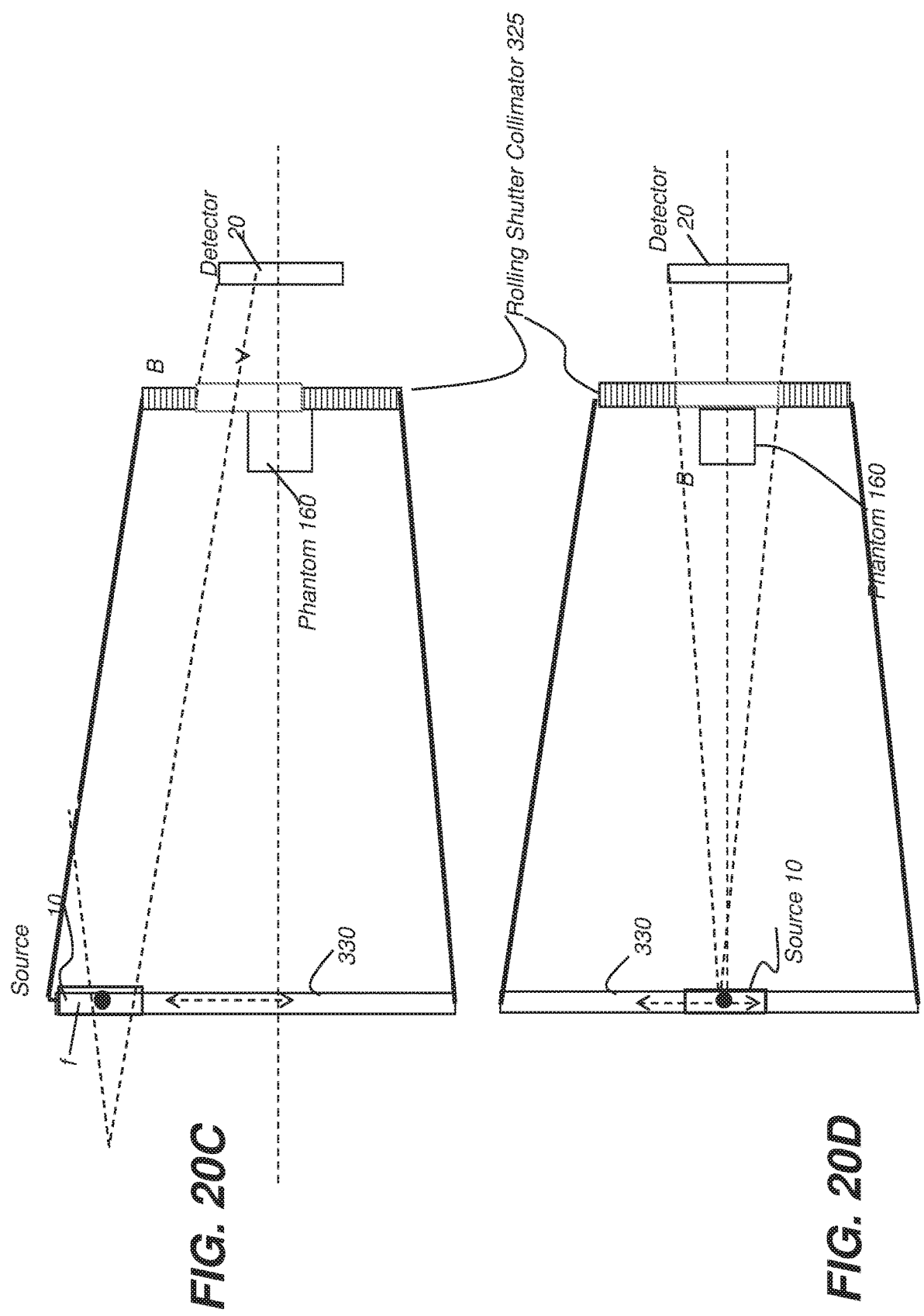

MOVABLE AND STATIC COLLIMATORS AND X-RAY SOURCE ARRANGEMENTS FOR INTRAORAL TOMOSYNTHESIS

TECHNICAL FIELD

The disclosure relates generally to intraoral imaging and, more particularly, to methods and apparatuses for collimation of the radiation path with intraoral tomosynthesis imaging.

BACKGROUND

A three-dimensional (3-D) or volume x-ray image can be of significant value for diagnosis and treatment of teeth and supporting structures. A volume x-ray image for this purpose is formed by combining image data from two or more individual two-dimensional (2-D) projection images, obtained within a short time of each other and with a well-defined angular and positional geometry between each projection image and the subject tooth and between each projection image and the other projection images. Cone-Beam Computed Tomography (CBCT) is one established method for obtaining a volume image of dental structures from multiple projection images. In CBCT imaging, an image detector and a radiation source orbit a subject and obtain a series of x-ray projection images at small angular increments. The information obtained is then used to synthesize a volume image that faithfully represents the imaged subject to within the available resolution of the system, so that the volume image that is formed can then be viewed from any number of angles. A commercially available CBCT apparatus for dental applications includes the CS 8100 3D System from Carestream Dental, LLC of Atlanta, Ga.

While CBCT imaging is a powerful diagnostic tool, there can be cases, however, where even though volume imaging is beneficial, the full-fledged capability of CBCT imaging is not needed. For some types of volume imaging such as for use in guiding implant placement, for example, a rudimentary volume imaging capability that provides a measure of depth information would be useful. Volume imaging can also help to avoid superposition anomalies between adjacent dental structures. For uses such as these, numerous x-ray projection images, such as those provided from a CBCT system, would not be required. Instead, sufficient depth information can be obtained using a smaller number of x-ray images, provided a spatial coordinate reference between images is maintained.

As a general principle, it would be advantageous to use the minimum number of x-ray exposures needed in order to generate the volume diagnostic data. A complete CBCT series of projection images acquired over a 180-degree orbit requires higher cumulative radiation dosage than does a partial series that is either taken over a smaller range of angles or uses fewer projection images taken at increased relative angular increments. Thus, the use of certain known methods can help to reduce patient exposure where full CBCT imaging is not needed.

Tomosynthesis appears to offer the dental practitioner a number of advantages over conventional 2-D radiography and 3-D tomography imaging, such as CBCT imaging, of intraoral features. In tomosynthesis, as with other volume imaging approaches, a limited number of 2-D projection images are obtained in sequence, with each image frame shifted in terms of relative angle from the previously acquired image frame. Reconstruction techniques can then be used to form a volume image of sufficient depth and resolution for a number of diagnosis and assessment functions. This gives tomosynthesis some of the benefits of full-scale tomography imaging for providing volume data with limited depth, but at lower dose than tomography requires.

Tomosynthesis imaging employs incremental geometric change of the relative radiation source angle, at each image, with respect to the detector surface. Conventional tomosynthesis systems, such as those used for mammography, for example, have inherent control of source position relative to detector and thus automatically achieve geometric alignment, which applies from one imaging exam to the next. With intraoral imaging, however, such types of mechanically fixed geometry are not easily obtainable. The intraoral detector is largely hidden from view and must be flexibly positionable at various locations within the mouth, frustrating attempts at straightforward source-to-detector alignment. Not only should the system be able to positively identify the boundary geometry of the detector outline, but the path traced by the partial orbit of the source should be symmetrical to detector pixel row/column geometry.

Related difficulties for intraoral tomosynthesis include the need for accurate collimation of the radiation beam. Effective collimation helps to prevent unnecessary exposure of areas that lie beyond boundaries of the detector. Still other aspects of the intraoral tomosynthesis system relate to the need to represent the reconstructed tomosynthesis image in suitable format for ease of use in assisting diagnosis. Thus, although a number of solutions have been proposed for providing intraoral tomosynthesis, there remain considerable areas for improvement in making tomosynthesis technology suitable for the dental practitioner. In particular, it can be appreciated that there would be advantages to apparatuses and methods that provide suitable collimation of the radiation path for intraoral tomosynthesis imaging.

SUMMARY

Broadly described, the present invention comprises apparatuses and methods for intraoral tomosynthesis imaging. In apparatus and/or method example embodiments, a volume image is generated from a small number of x-ray images acquired by an intraoral imaging detector.

According to one aspect of the disclosure, there is provided an intraoral imaging apparatus for tomosynthesis imaging comprising (a) an intraoral detector that is coupled to a frame that defines a target aperture for an incident radiation beam, and (b) an enclosure that is configured to seat against the target aperture. The enclosure houses (i) at least one x-ray source that is configured to emit a radiation beam from each of a plurality of focal points within the enclosure, (ii) a collimator that is disposed to form a collimated beam from the emitted radiation beam and direct the collimated radiation beam through the target aperture and to the detector as the incident radiation beam, and (iii) a geometric calibration phantom having a plurality of radio-opaque markers and disposed in the path of the collimated beam.

According to another aspect of the invention, there is provided an intraoral imaging apparatus for tomosynthesis imaging comprising (a) an intraoral detector that is free and not attached to any frame and also includes a radio-opaque marker on its surface, and (b) an enclosure that is configured to be positioned freely without any attachment to the patient's anatomy or the intraoral detector location. The enclosure houses (i) at least one x-ray source that is configured to emit a radiation beam from each of a plurality of focal points within the enclosure, (ii) a collimator that is disposed to form a collimated beam from the emitted radiation beam and direct the collimated radiation to the detector as the incident radiation beam, and (iii) a radio-opaque marker attached to the collimator so it is in the path of the beam projected onto the detector and is able to align the x-ray focus to the detector, and (iv) a geometric calibration phantom having a plurality of radio-opaque markers and disposed in the path of the collimated beam.

The foregoing and other aspects, features, and advantages of the invention will be apparent from the following more particular description of example embodiments of the invention and the accompanying drawings which are not to scale.

BRIEF DESCRIPTION OF THE DRAWINGS

FIG. 1 is a schematic diagram showing components of a chairside tomosynthesis imaging apparatus according to an example embodiment.

FIG. 2A is a schematic diagram that displays a photon-counting apparatus.

FIGS. 3A and 3B are simplified schematic block diagrams that display different aspects of an alignment problem.

FIG. 4 is a schematic block diagram displaying an imaging apparatus that calculates a lateral position and angular orientation of an intraoral image detector.

FIGS. 20A and 20B display basic geometrical considerations for shifting a collimator window in conjunction with a changing focal point for emission.

FIGS. 20C and 20D display basic geometrical considerations for a rolling shutter collimator window in conjunction with a changing focal point for emission.

DESCRIPTION OF EXAMPLE EMBODIMENTS

Figure 2B:
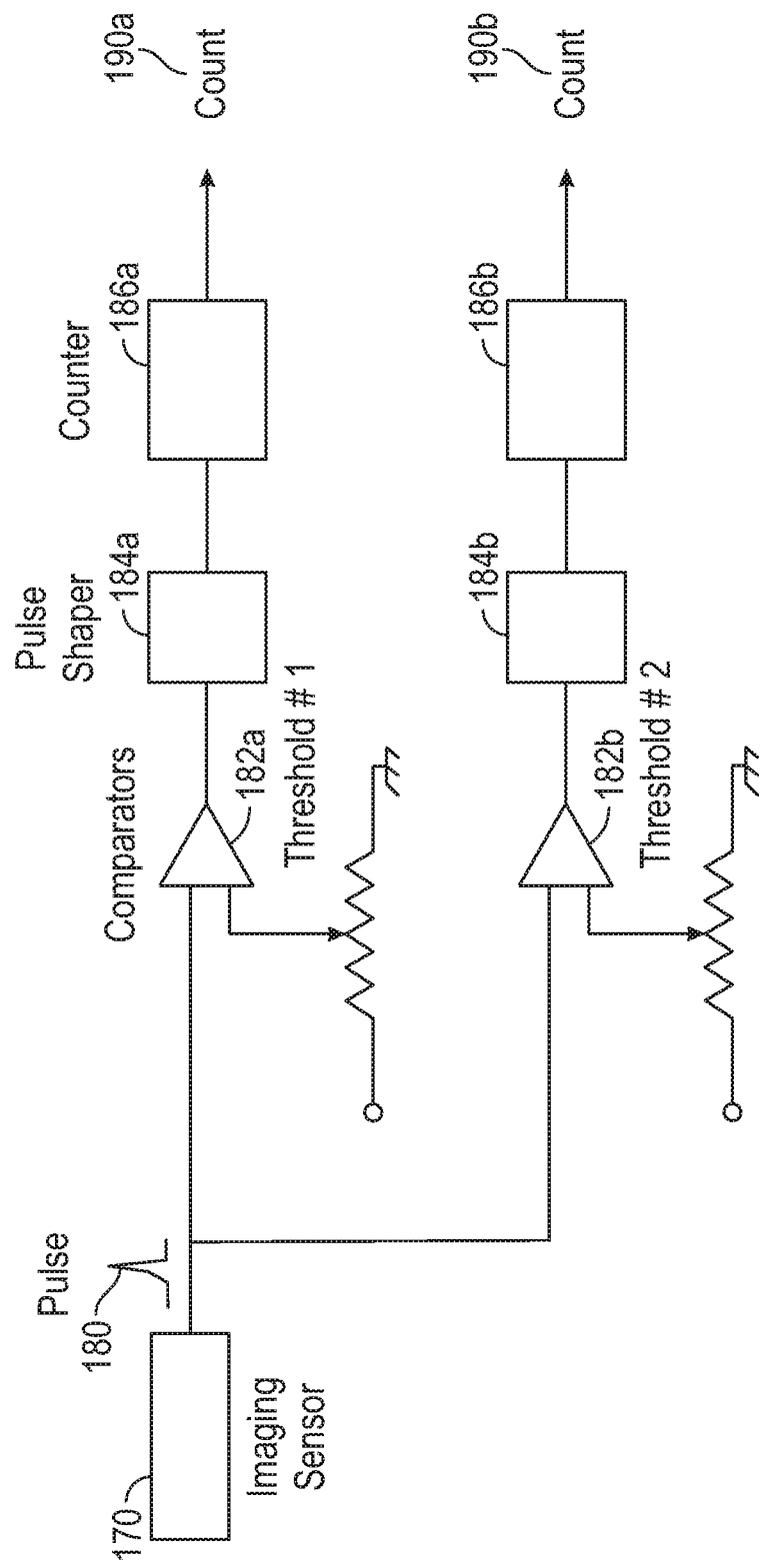
FIG. 2B is a schematic diagram that displays a photon-counting apparatus for measurement at two different energy levels.

The following is a detailed description of example embodiments of the present invention, reference being made to the drawings in which the same reference numerals identify the same elements of structure or steps of a method in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components configured with connection to a power source and actuable to perform an indicated function upon receiving power and, optionally, upon receiving an enabling signal.

In the context of the present disclosure, the terms "viewer", "operator", and "user" are considered to be equivalent and refer to the viewing practitioner, technician, or other person who views and manipulates an image, such as a dental image, on a display monitor. An "operator instruction" or "viewer instruction" is obtained from explicit commands entered by the viewer, such as by clicking a button on a camera or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the present disclosure, the term "detector" refers to the element that is placed in the patient's mouth, receives radiation, and provides the image content. Such a detector is a digital detector that provides the x-ray image data directly to an imaging system.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional volume images and a pixel for 2-dimensional images. Volume images, such as those from CT or CBCT apparatus, are formed by obtaining multiple 2-D images of pixels or projection images, taken at different relative angles, then combining or reconstructing the image data to form corresponding 3-D voxels. For the purposes of the description herein, the terms voxel and pixel can generally be considered equivalent, describing an image elemental datum that is capable of having a range of numerical values. Voxels and pixels have the attributes of both spatial location and image data code value.

Planes can be considered "in parallel" if they are parallel to within no more than 12 degrees in any direction.

FIG. 1 is a schematic diagram showing components of a chairside tomosynthesis imaging apparatus 100 according to certain example method and/or apparatus example embodiments of the present invention. An x-ray source 10 directs radiant energy through a subject tooth 14 or other feature toward an intraoral detector 20, over a range of angles. A collimator 16 conditions the angular extent of source 10 radiation so that the exposure is constrained to within the region of interest. An alignment apparatus 70 senses and optionally controls the alignment of the radiation field from source 10 and through collimator 16 to provide radiation over the region of interest. Intraoral detector 20 is in signal communication with a control logic processor 26 that acquires and processes the image content to provide a tomosynthesis image on a display 28. Tomosynthesis imaging requires a changing relative angle of the source 10 to the detector 20, as described in more detail herein. Control logic processor 26 provides the control required for tomosynthesis image acquisition.

Tomosynthesis imaging requires that the components shown in FIG. 1 acquire two or more 2-D projection images of the region of interest, such as images of one or more adjacent teeth, for example. The generated image content includes some amount of contour and depth information, but not the more geometrically complete image volume data obtained from tomography, such as from CBCT systems.

The tomosynthesis data provides a measure of depth information without full volume image content. Tomosynthesis allows generation of slices or layer images into the imaged object, wherein the slices/layers are at different depths.

It should be noted that collimator 16, shown in generalized form in FIG. 1, typically includes two collimator assemblies, spaced apart from each other along the radiation path and cooperating to provide the beam collimator function. A first collimator is typically included as an integral component of the x-ray source 10, with collimator blades or other beam-guidance features positioned to define the shape of the emitted x-ray radiation as it proceeds along the radiation path. A second collimator can be provided near the detector 20, further defining the beam outline so that the x-ray beam is incident within the detector 20.

Reflectance Image Acquisition

An optional reflectance imaging apparatus 96 may also be provided as part of some exemplary chairside oral imaging method and/or apparatus embodiments, such as for providing more accurate positioning information for the detector 20 placed within the mouth of the patient. Imaging apparatus 96 can provide contour imaging, such as by projection of a structured light pattern onto the intraoral feature of interest. Contour information is then processed in order to generate a 3-D mesh showing surface features. For this purpose, the reflectance imaging camera serves as an optical scanner. Alternately, imaging apparatus 96 can be a 2-D camera for obtaining one or more monochromatic or color images from and around the region of interest.

Reflectance imaging may be used, for example, to determine head size and/or orientation. Acquired reflectance images may also serve as an aid to detecting patient motion during tomosynthesis and/or another radiological image acquisition. A contour imaging camera image, such as provided by a CS3600 intraoral scanner from Carestream Dental LLC, can provide more information than 2-D reflectance images for guiding and/or correcting the volume reconstruction processing used in tomosynthesis and for motion detection during the tomosynthesis exam. An optional ultrasound imaging apparatus 98 can similarly be provided as a support system for chairside oral imaging apparatus 100.

According to an alternate example embodiment according to the application, a full-mouth scanning apparatus works in conjunction with the radiographic imaging system. This enables the simultaneous acquisition of both radiographic and reflectance images, for example, which can be useful for subsequent reconstruction processing. The reflectance and tomosynthesis image content can be fused together to show some depth information with reference to highly accurate surface contour information.

Types of imaging apparatus that acquire depth-resolved image content, such as optical coherence tomography (OCT) and ultrasound imaging systems, obtain from captured reflectance signals not only surface contour information, but also potentially provide some amount of additional information for characterization of tissue and features detected, up to some depth below the surface. This type of depth-resolved image content can be a more useful aid to support and validate positioning of the tomosynthesis acquisitions as well as to help identify and report or compensate for detected movement of the patient during the imaging session. There can be supportive information obtained by depth-resolved imaging apparatus for features just beneath the surface, for example, that can be more useful for positioning guidance and verification than is available when only using surface contour imaging content.

Radiation Source

According to example method and/or apparatus embodiments of the present invention, the x-ray source 10 is a Spindt-type field emitter (including carbon nanotube or CNT-based field emitters), providing radiant energy from a number of distributed x-ray sources. The x-ray sources may be, for example, a distributed array or panel (2d array) of Spindt-type field emitters, which can be peripherally arranged about a central thermionic source. The x-ray sources are stationary or relatively fixed in position with respect to each other within the array/panel; the array itself moves as a single unit. This type of x-ray source is capable of rapid on/off switching on the order of microseconds.

Other suitable x-ray sources may include paired pulsed conventional fluoro-capable thermionic sources in an array, where the sources are spatially separated. These options provide sufficient x-ray fluence with short exposure times and simultaneously allow exposure sequences without overheating.

A Spindt-type field emitter-based x-ray source has one or more cathodes within a vacuum chamber, wherein each cathode is formed from a large number of individual Spindt-type field emitters that, given excitation current, provide electrons that are then accelerated toward one or more anodes in the chamber.

Alternately, the x-ray source may be a more conventional thermionic source, coupled with a transport apparatus that provides the needed energy to move the x-ray source along a linear or non-linear (e.g., curved) travel path that can be segmented or continuous for directing radiation toward the subject.

According to an example embodiment of the present invention, the same x-ray source may be used in any of a set of modes for conventional radiography or 3-D imaging. Thus, the same radiation imaging apparatus may be used for acquiring single-shot radiographic images, or for acquiring and processing projection images for tomography including CBCT, tomosynthesis, or for fluoroscopy or radioscopy imaging, as described in more detail herein.

Generator

The radiation generator that is part of the x-ray source may provide pulsed or continuous operation. The generator may provide a single pulse or a series of pulses, with pulse widths varied in order to provide suitable exposure conditions for particular features.

Imaging Detector

The imaging detector of the methods and/or apparatuses of the example embodiments is a small, intraoral digital radiography (DR) detector that acquires image data at a rate sufficient for tomosynthesis imaging. The imaging detector may be any suitable shape and may be rigid or flexible.

Signal communication with the imaging detector may be wired or wireless. The image detector may receive power from a cable or may have an on-board rechargeable battery.

In order to meet the requirements of tomosynthesis imaging, the intraoral detector has a fast response time, with an image acquisition rate sufficient for tomosynthesis acquisition, acquiring at least about 2 frames per second (fps), at least 5 fps, or at least 10 fps.

The imaging detector may be a conventional DR detector that generates image content using relative energy integration or may be a photon counting detector. According to an example embodiment of the present invention, the same imaging apparatus may allow connection to multiple types of imaging detector. This allows a versatile imaging apparatus capable of single-frame radiographic imaging (e.g., up to 43×43 cm) with one detector and multiple projection image acquisition (e.g., 3-D or volume imaging) using a different detector, for example, in addition to chairside tomosynthesis imaging described herein.

Some of the advantages of the photon counting detection compared to the energy integration detection include: (i) reduction of electrical noise and improvement of the signal-to-noise ratio; and (ii) improvement of image contrast, such as adjusting weighting factors for images acquired with energy binning. Photon counting tomosynthesis can provide improved diagnostic accuracy.

Conventional integrating x-ray sensors are spatially digitized and provide an analog output that represents the accumulated charge received for each pixel during the exposure. High noise levels can be a problem with integrating sensors. In photon counting, each incoming photon generates a charge and each charge event is recorded. The actual count of photons, or a value correspondingly computed based on the count, is provided as the image data for each pixel. Advantageously, photon counting has high immunity to noise, provided that pulse strength exceeds background noise levels.

FIG. 2A displays a photon-counting apparatus in schematic form. An incoming photon generates a pulse 180 at a given energy level. The pulse 180 energy is compared against a threshold value at a comparator 182 and shaped in a pulse shaper 184 to form a shaped pulse 188. A counter 186 then records the pulse event and provides a digital output, a pulse count value 190. A separate pulse count value 190 is obtained for each pixel element in imaging sensor 170 that is used for detector 20. The threshold value can be adjustable or selectable from a range of values, depending on the photon energies of interest. Photon counting x-ray detectors provide suitable performance at low signal level, and therefore allow reducing the x-ray dose given to a patient.

It should be understood and appreciated that multiple detector technologies may be combined. Example combinations include, but are not limited to: (1) Indirect-Detection with Integration, (2) Direct-Detection with Integration, (3) Indirect-Detection with Photon-Counting, and (4) Direct-Detection with Photon-Counting. Indirect-Detection with Integration provides reduced detector cost and scalability. Direct-Detection with Integration provides reduced dose with larger-scale detectors. Indirect-Detection with Photon-Counting provides for reduced dose. Direct-Detection with Photon-Counting may provide reduced dose and/or color x-ray, as described in more detail herein.

A further advantage of pulse counting relates to its capability to count pulses 180 at multiple threshold values. Referring to the schematic diagram of FIG. 2B, two comparators 182a and 182b are shown for measuring pulse energy. In this particular configuration, a comparator 182a, a pulse shaper 184a, and a counter 186a provide a count 190a value for all pulses above a first threshold; similarly, a comparator 182b, a pulse shaper 184b, and a counter 186b account for only pulses above a higher, second threshold and provide a count 190b accordingly. Simple subtraction then identifies the different power levels achieved for each pulse. It should be understood and appreciated that more than two threshold levels may be measured, using a corresponding arrangement of comparator circuitry, allowing pulse counts at any of a number of threshold values. In addition, thresholds may be selectable, such as adjustable to adjust the response of imaging sensor 170 to various photon energy levels. Thus, for example, an operator may use a set of preset thresholds for differentiating softer from denser tissue in the image that is finally generated.

In addition to setting minimum of floor thresholds (e.g., for noise reduction), embodiments of the present invention for multi-spectral x-ray imaging may also provide the option of using additional upper or maximum thresholds for photon energy. This upper threshold capability may be used for a number of functions, including reducing the generation of excessive noise signals such as from metal artifacts or x-rays passing directly through the direct detection material.

The capability to count photons at different energy thresholds, as described with reference to FIG. 2B, allows the intraoral detector to differentiate between energy levels obtained from irradiating the subject and provides added dimension to the image data that is provided as a result of each exposure. This capability, described as multi-spectral or "color" x-ray imaging, enables information to be obtained about the material composition of a subject pixel. As is well known, two materials A and B can have different coefficients of attenuation, μ, that vary with the level of radiation energy exposure. At a given exposure, material A attenuates a photon with an energy that corresponds to material A. Similarly, radiation impinging on material B attenuates a photon with an energy that corresponds to material B. Where photons of these different energy values can be differentiated from each other, it is possible to identify one or both materials in the same pixel or voxel image element of the obtained image. This same basic behavior in response to radiation also allows some measure of capability to differentiate tissue types. Different linear absorption characteristics allow differentiation between various types of tissue such as, without limitation, between bone types.

Color x-ray using photon counting detectors provides for low cost and low dose color x-ray imaging. The use of multi-spectral or "color" x-ray imaging may have a number of potential benefits of value for intraoral imaging. These include minimization of metal artifacts, separate reconstruction of soft and hard tissue, more efficient segmentation algorithms for tooth and bone features, improved pathology detection for cancer and other disease, and detection of trace materials or contrast agents.

According to an example embodiment of the present invention, chairside intraoral imaging apparatus 100 may have two or more interchangeable detectors 20, suitable for different imaging functions. For example, a conventional integrating image detector may be connected to processor 26 for radiographic imaging and a photon counting detector may be connected only when needed for tomosynthesis or radioscopic imaging. Keyed connectors or other mechanical or signaling mechanism may be used to indicate which type of detector is connected.

Among techniques that may be used for providing adjustable resolution and increasing acquisition speed are detector binning, described in more detail herein. Binning groups together uniform sets of adjacent sensor elements to provide a single, averaged value for the individual area of each set of pixels.

Source/Detector Alignment

Detector alignment may be difficult for dental or intraoral radiography. The detector position is within the patient's mouth and is not visible to the technician. Instead, the technician typically places the detector into some type of holder, and then inserts the holder into place in the mouth. The holder may have a bite plate or other type of supporting member that helps to position the detector appropriately. As is well known, holders of this type can be cumbersome and uncomfortable to the patient. Holders and other positioning devices are not error-proof, and positioning errors with these devices may mean that the images obtained are not suitable for diagnosis. Poorly aligned detectors may be the cause of problems such as cone cuts, missed apices, and elongation and related angulation or parallax errors, for example. These alignment problems may result in the need for re-takes, additional image captures to acquire an acceptable image. Re-takes are undesirable due to the additional x-ray radiation exposure to the patient and prolonged patient discomfort with the detector or sensor in the mouth.

Conventional x-ray sources have included aim indicators that help the technician adjust the position and angle of the x-ray source. Often these aim indicators use visible light to trace an outline that helps to center the radiation beam. These work well where the radiation detector can be seen, but fall short of what is needed where the detector is not visible, such as with intraoral imaging. The technician must guess or estimate both the position of the intraoral sensor and the angle of incidence of x-rays on the sensor.

The simplified schematic of FIGS. 3A and 3B show how misalignment between an x-ray source 10 and a detector 20 can occur. In these examples, x-ray source 10 provides visible light aim indices 12 used for aim centering. When correct aim alignment is achieved (shown at example (a)), detector 20 is centered as shown within aim indices 12. Aim is incorrect in examples (b) and (d).

For best imaging results, proper alignment with respect to angle, or angulation, is also needed. Incident radiation from x-ray source 10 is preferably orthogonal to detector 20 as shown in example (a). Line N in FIGS. 3A and 3B indicates a normal, or orthogonal line, to the surface of detector 20. Examples (c) and (d) show incorrect angular alignment. In example (c), aim or centering is correct, but angulation or pitch is incorrect. In example (d), both aim (centering) and angulation (pitch) are incorrect. In example (e), detector 20 is rotated in plane (roll).

It is instructive to note that the schematic examples of FIGS. 3A and 3B assume an orthogonal positioning of x-ray source 10 to detector 20. In some embodiments, an oblique orientation may be used.

Alignment and positioning are particularly important for volume imaging applications in which images taken at different angles are to be combined in some way to form volume image data. In tomosynthesis, the relative movement between source and detector introduce further complexity into the alignment problem. It is generally most favorable for reconstruction processing to have the line or arc of movement disposed such that the spatial position of the source is within the same plane relative to the detector surface, or equidistant from the surface, so that movement aligns with pixel positions on the detector surface for each acquired projection image.

In order to better understand the parts and operation of the apparatus of the present invention, it is helpful to show how proper alignment may be detected by an imaging system. Referring to the schematic block diagram of FIG. 4, there is shown an intraoral imaging apparatus 22 that detects alignment of imaging detector 20 with x-ray source 10. In the FIG. 4 arrangement, detector 20 is placed at a detector position that is adjacent to a tooth 14, inside a cheek 18 of the patient. Incorporated as part of detector 20 are a number of detectable elements 30, which are shown as electromagnetic signal emitters, such as radio-frequency (RF) emitters. Detectable elements 30 are typically spaced apart from each other in order to provide triangulation information. A sensor 24, itself aligned and positionally coupled with x-ray source 10, senses the presence of detectable element 30 in some way, such as by sensing emitted RF signals. Methods for energizing and sensing RF emitters, such as the tiny emitters used in RFID tags, for example, are well known to those in the signal detection arts. A control logic processor 26, in signal communication with one or more sensors 24, employs conventional trigonometric calculations based on the received signals from, or other detectable features of, detectable elements 30 and the known position of sensor 24 with relation to x-ray source 10. This is performed in order to determine the corresponding positional and angular alignment of detector 20 in the patient's mouth relative to x-ray source 10. An operator console display 28 on a computer display monitor then indicates alignment information for the operator and may recommend the needed adjustment settings. Sensors 24 are energizable to receive electromagnetic signals of one or more predetermined frequencies.

Figure 5:
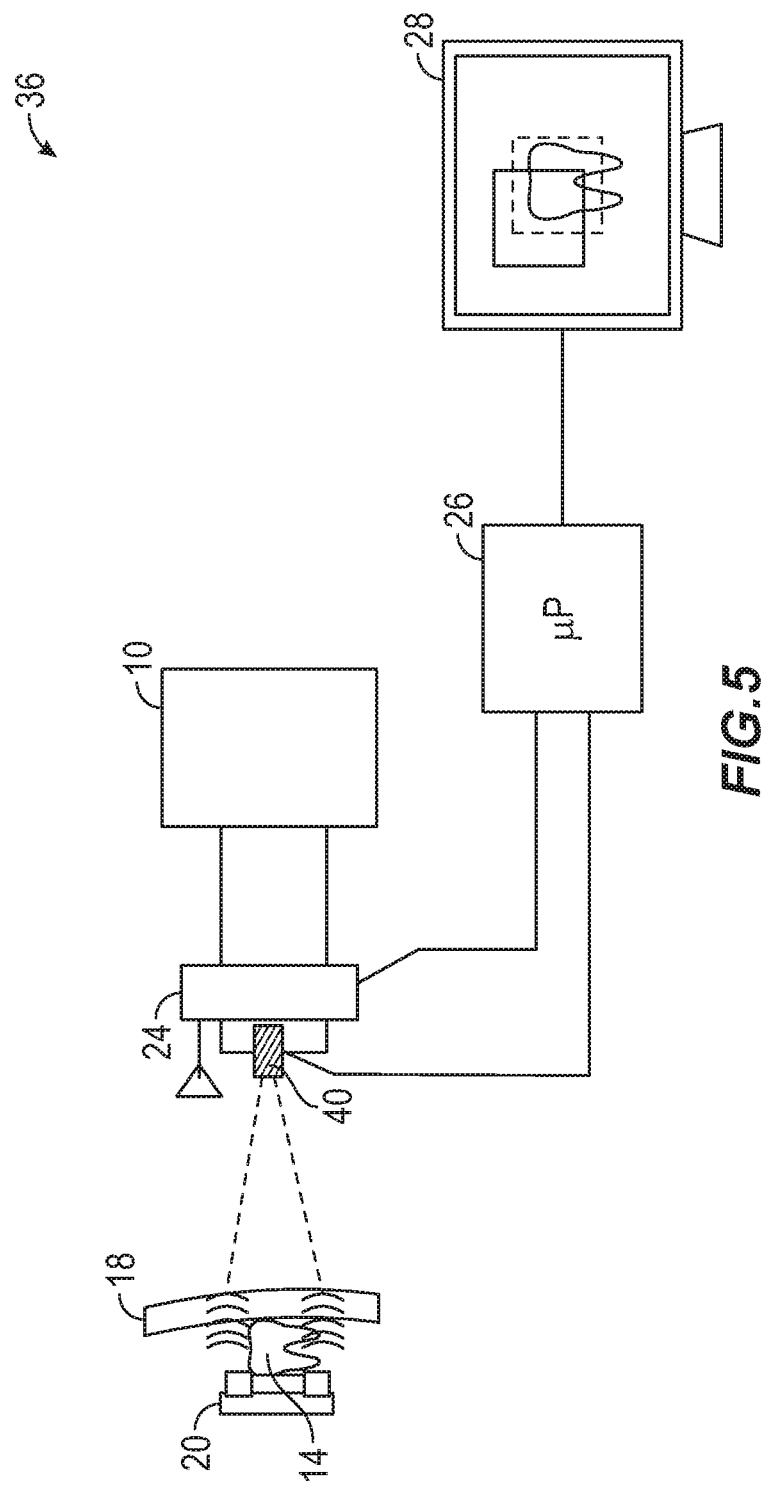
FIG. 5 is a schematic block diagram displaying an imaging apparatus that calculates a lateral position and angular orientation of an intraoral image detector and projects a display onto a patient's cheek.

Certain example method and/or apparatus embodiments of the present invention improve upon the basic system of FIG. 4 by providing alignment information to the technician where it can be more easily used, particularly where this information is needed in order to obtain the individual images used for forming a volume image. Example alignment apparatus of the present invention can project an image onto the cheek or other portion of the dental patient as a guide for proper alignment of the x-ray tube with respect to the position and angle of the detector. Referring to an embodiment of an imaging apparatus 36 in FIG. 5, control logic processor 26 obtains alignment information in similar manner to that described in FIG. 4. In addition, as shown in FIG. 5, control logic processor 26 may also be in image data signal communication with a projector 40 for projecting an image onto the patient's cheek 18, lips, or face.

Figure 6A:
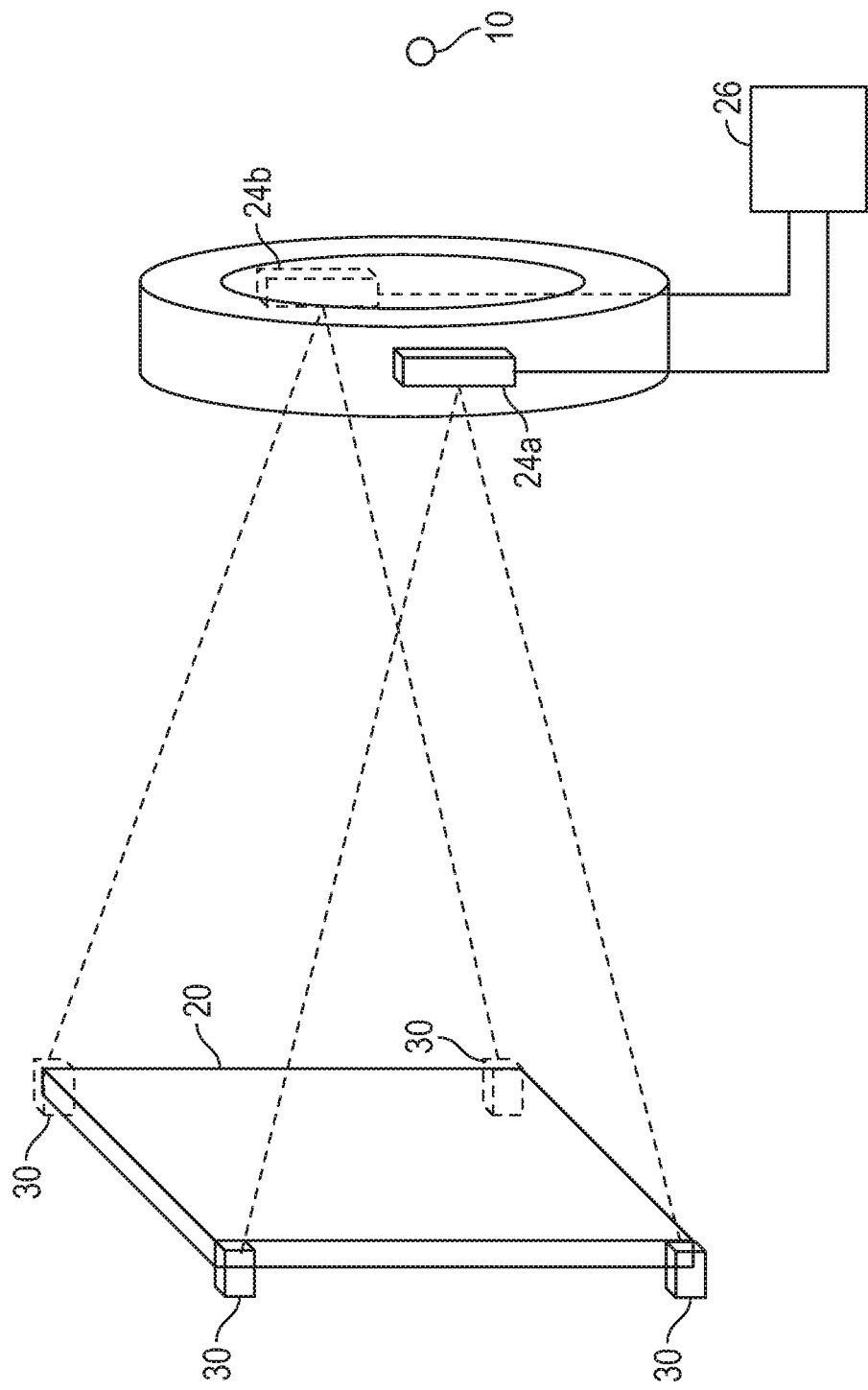
FIG. 6A is a schematic diagram that displays how triangulation is used for position detection in one example embodiment of the present invention.

The perspective view of FIG. 6A shows, in schematic form, how triangulation may be used to indicate position and angle of detector 20 in order to determine alignment offset in one embodiment. Sensors 24a and 24b, RF transceivers in one embodiment, are at a known position relative to the x-ray source 10 such as mounted near the x-ray source on the x-ray tube, for example. Signal emitters or other type of detectable elements 30 are typically disposed in pairs, positioned at corners of detector 20. Each detectable element 30 has a detectable feature that can be sensed by sensors 24a and 24b. In one embodiment, each detectable element 30 is an RF device that generates an electromagnetic field, such as in response to a transmitted signal from its corresponding signal receiver, sensors 24a or 24b. Phase, intensity or other characteristic of the emitted electromagnetic field is measured at the corresponding sensors 24a and 24b, and is used in order to determine relative distance between emitting and receiving components. For the RF detection embodiment of FIG. 6A, for example, when signals for each pair of emitters, acting as detectable elements 30, are in phase, good alignment has been achieved. An out-of-phase condition indicates poor alignment and may indicate the needed direction for adjustment. Sensors 24a and 24b are in signal communication with control logic processor 26.

In a similar manner, relative signal strength may alternately be used to indicate the position and angle of detector 20 with respect to the x-ray source for determining alignment offset. Using this approach in an RF embodiment, the nearest signal emitter acting as detectable element 30 has, correspondingly, the strongest intensity signal at sensor 24a or 24b. When the arrangement of FIG. 6A is used, signals of equal intensity emitted from all four emitters or other type of detectable element 30 indicate good alignment. When signal intensities vary, the pattern for their variation can be used to indicate which adjustments are needed. As one example, a position detection system may use triangulation and sensing of multiple emitted signals to compute alignment positioning. It should be understood and appreciated that any of a number of different configurations may be used for determining proper alignment using one or more sensors 24 and detectable elements 30, as is well known to those skilled in the signal processing and position sensing arts.

Figure 6B:
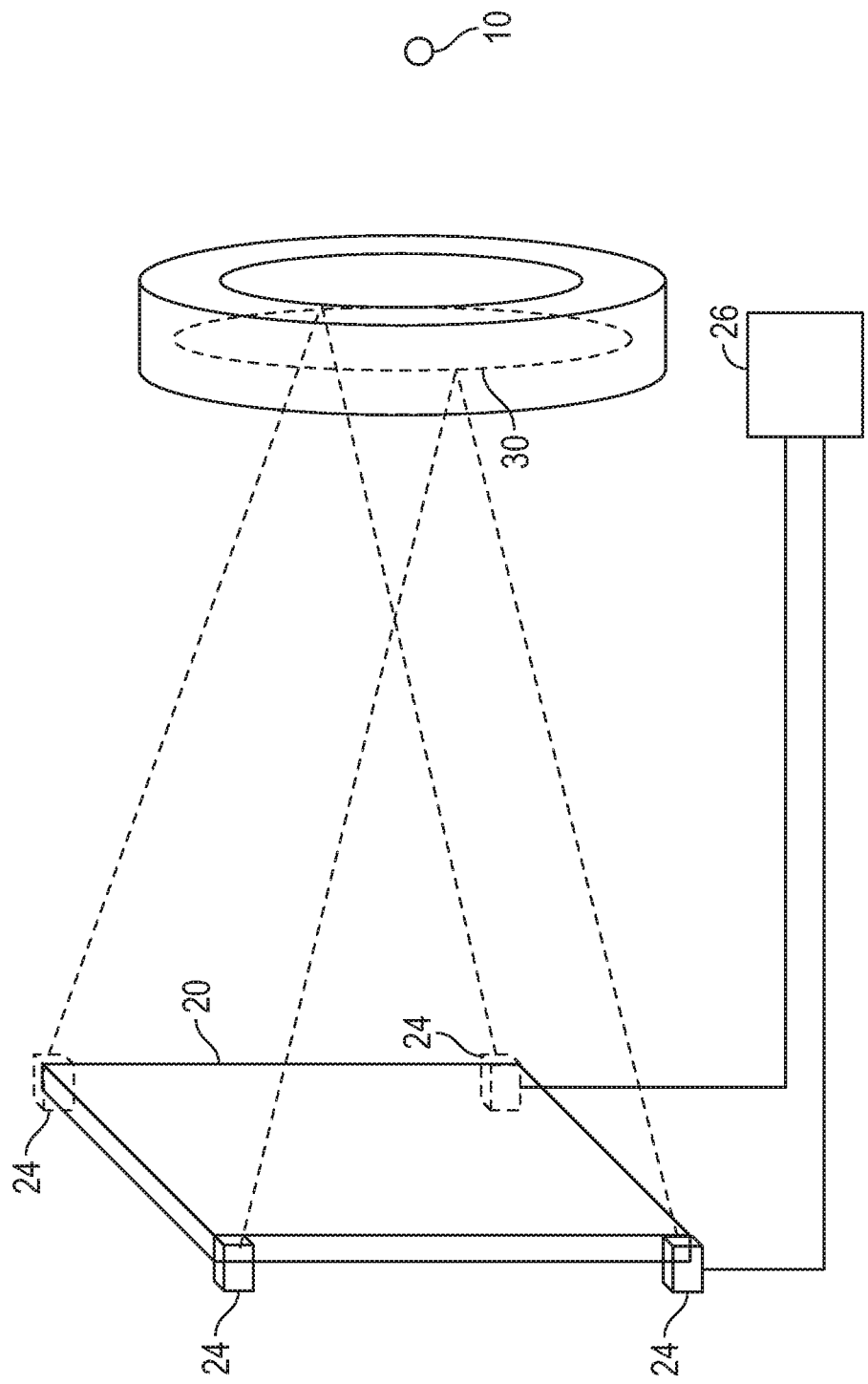
FIG. 6B is a schematic diagram that displays position detection in an alternate example embodiment of the present invention.

In one alternative example embodiment, shown in FIG. 6B, the emitter-detector arrangement that was shown in FIG. 6A is reversed, so that one or more emitters that provide one or more detectable elements 30 are mechanically coupled to x-ray source 10 and two or more sensors 24 are attached to detector 20. In the embodiment shown in FIG. 6B, for example, detectable element 30 (shown in dashed outline) is a coil that generates an electromagnetic field that is sensed by sensors 24. Sensors 24 are in signal communication with control logic processor 26, either through a direct (e.g., wired) or an indirect (e.g., wireless) connection.

Alternate Alignment Mechanisms

In one example embodiment of the present invention, an intraoral scanner or other reflectance imaging sensor may be used as an aid to source alignment with the detector. The optical scan data obtained from a contour image or conventional reflectance image may be analyzed as a type of "scout" scan in order to determine the desired trajectory for the tomosynthesis scan.

In another exemplary embodiment of the present invention, ultrasound imaging may also be used as an alignment aid for source positioning. Ultrasound may be particularly useful with its capability to image soft tissue structures within the anatomy.

It should be noted that CNT (carbon nanotube) source alignment may be adjustable to control the trajectory of relative positional change of the radiation source for each subsequent image.

Figure 6D:
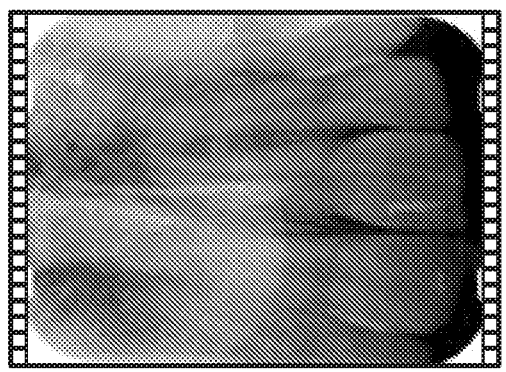
FIGS. 6D and 6E display how markers appear in an acquired image, along borders of the imaged intraoral features.
Figure 6E:
Figure 6C:
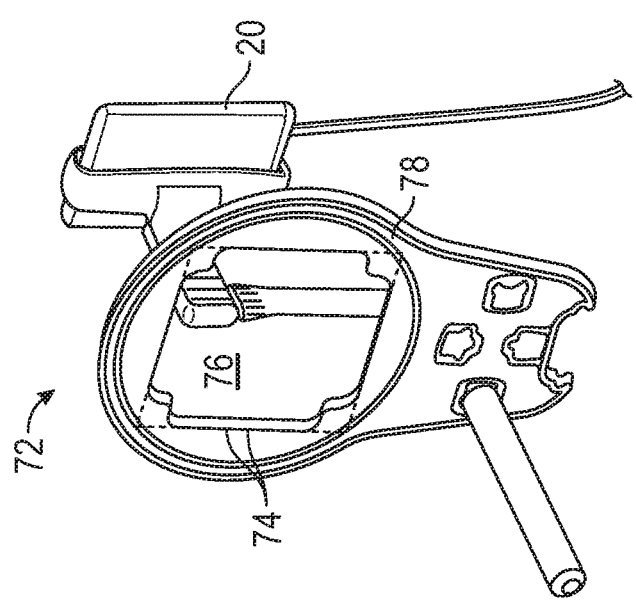
FIG. 6C is a schematic diagram that displays a holder having an arrangement of radio-opaque alignment markers about a central opening.

One method and/or apparatus example embodiment according to the present invention provides autofocus and alignment functions using an arrangement of embedded markers within a holder that is used for positioning the intraoral sensor. FIG. 6C shows a holder 72 for a frame 78 having an arrangement of radio-opaque markers 74 about a central opening 76 that orients the x-ray source 10 (not shown in FIG. 6C). FIGS. 6D and 6E show how the markers 74 appear in the acquired image, along the borders of the imaged intraoral features. Using the alignment markers allows image processing to correlate the positions of successively acquired images and to accurately register the projection images to each other for subsequent reconstruction.

It may be observed that solutions such as those shown in FIGS. 6A-6C may be used for alignment in any number of source-to-detector arrangements, as is described in more detail herein.

Projection of Outline onto Patient or Other Alignment Feedback

Figure 7A:
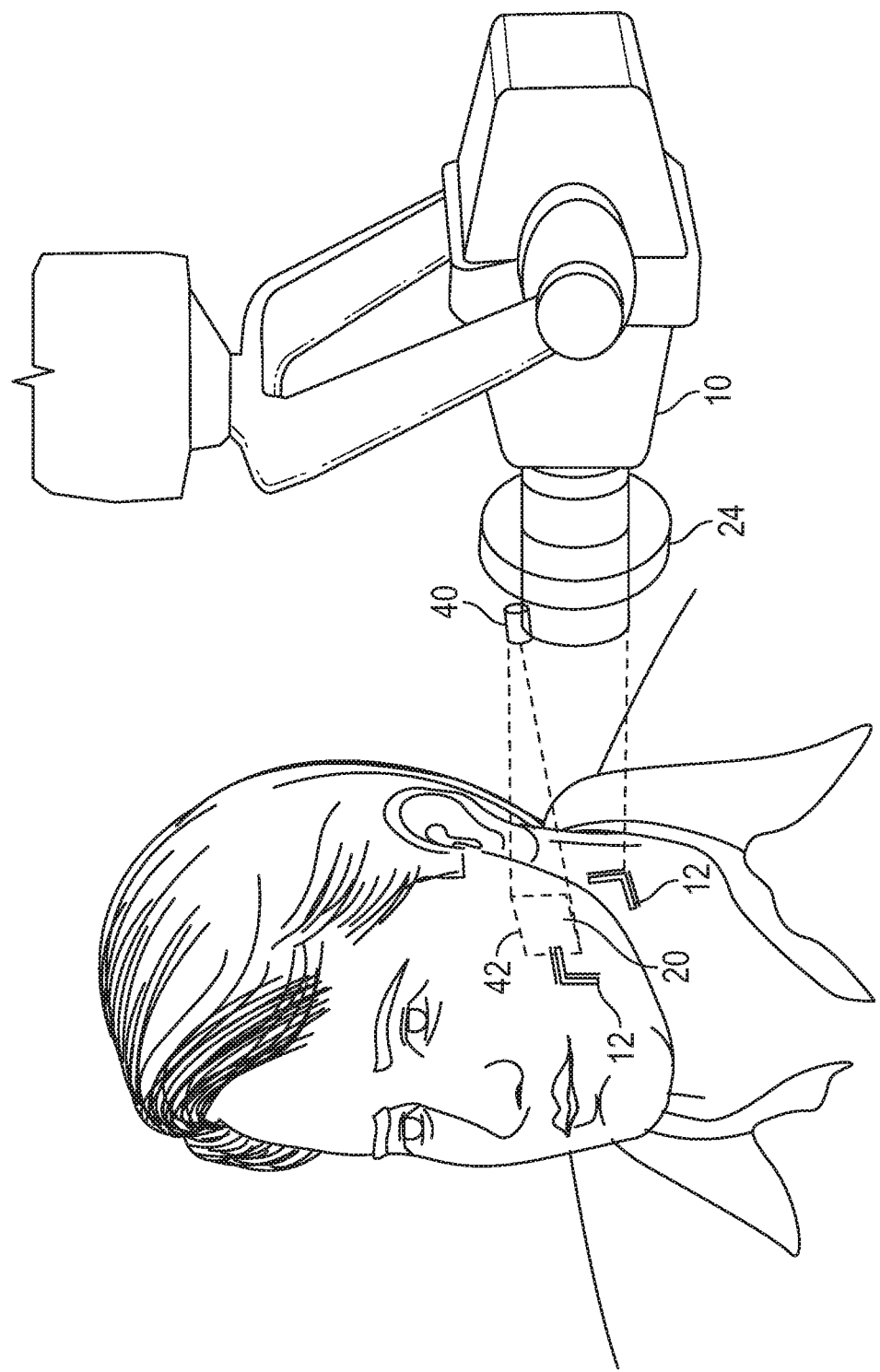
FIG. 7A is a perspective view displaying an intraoral x-ray imaging apparatus according to one example embodiment, in which alignment is not correct.
Figure 7B:
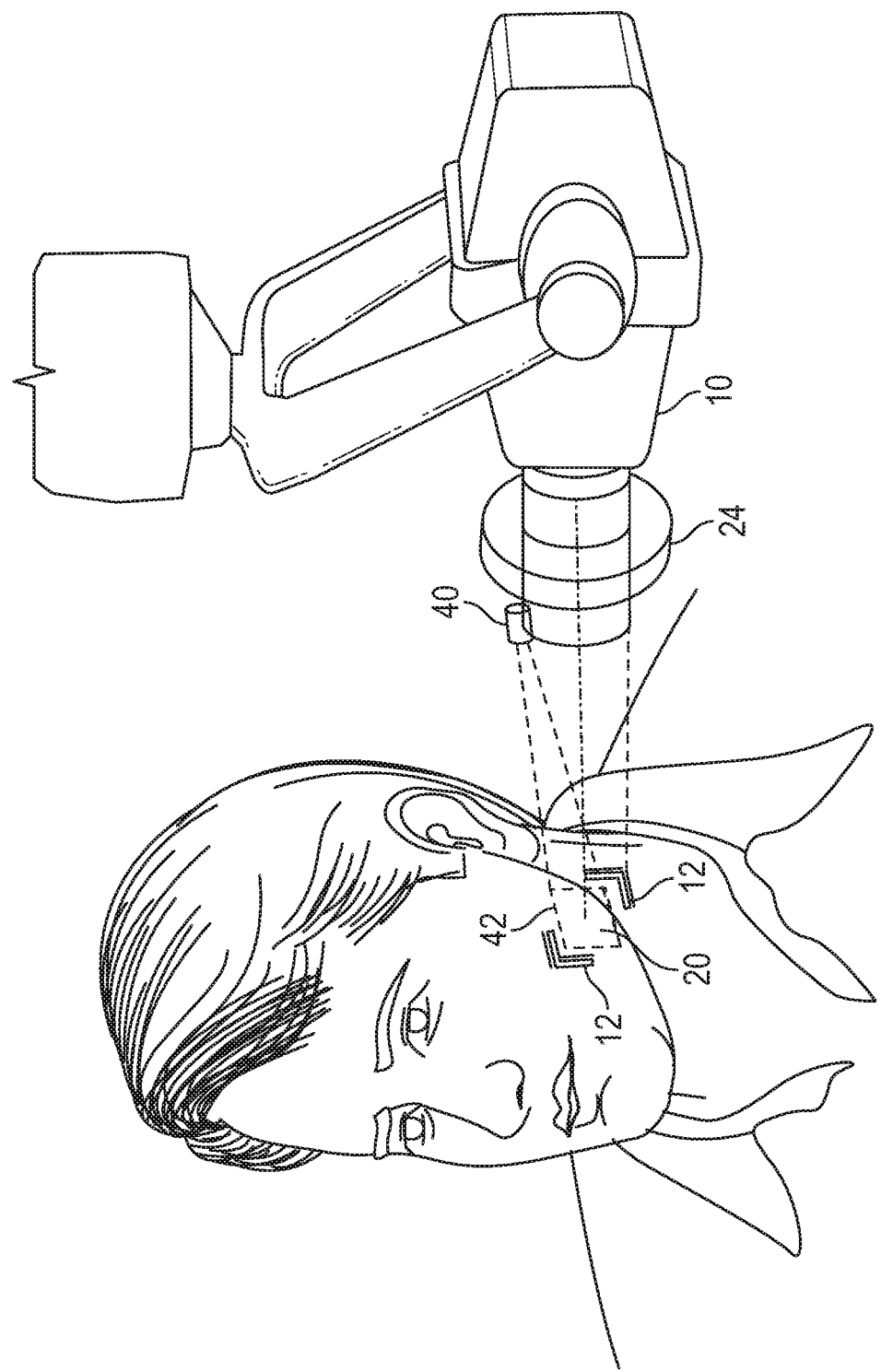
FIG. 7B is a perspective view displaying an intraoral x-ray imaging apparatus according to one example embodiment, in which alignment is correct.

Referring to the perspective views of FIGS. 7A and 7B, the added advantage of example embodiments of the present invention that provide optional image projection is shown. Projector 40, positionally coupled to x-ray source 10, such as mounted in position toward the end of the x-ray tube or on some other portion of the x-ray system, for example, projects a two-dimensional image onto the patient's cheek in order to indicate a position 42 of the concealed detector 20 (shown in dotted outline) and, unless already provided by the x-ray source 10, also to indicate the aim indices 12 of the x-ray source. FIG. 7A shows an example in which aim alignment is incorrect, since position 42 is not aligned with aim indices 12. FIG. 7B shows an example in which aim alignment is correct, with position 42 centered between aim indices 12.

Projector 40 may be any of a number of types of imaging projector that can be mounted onto x-ray source 10. In one example embodiment, projector 40 is a pico-projector such as, but not limited to, a Pico Projector Display from Microvision Inc. of Redmond, Wash. Devices such as these are advantaged for a number of reasons, including small size, low weight, and low power requirements. These pico-projectors, used in cell-phone and other highly portable electronic devices, scan one or more low-power lasers onto a display surface. The pico-projector requires a minimum of optical components for projection over a range of distances. The laser itself is turned on and off rapidly as needed so that power is consumed only for those image pixels that are projected. This allows the pico-projector to operate at low power levels so that battery power could be used for projector 40. Alternate example embodiments use other types of electronic imaging projectors, such as those that employ a digital micromirror array such as the Digital Light Processor (DLP) from Texas Instruments, Inc.; an array of micro-electromechanical grating light valves such as the Grating Light Valve (GLV) device from Silicon Light Machines, Inc.; or, a liquid crystal device (LCD) including a Liquid Crystal on Silicon (LCOS) device.

Where lasers are used as illumination sources in projector 40, additional measures may be taken to minimize incidence of coherent laser light to the eyes of the patient or practitioner. Very low power lasers may be used, such as solid-state lasers, at scanning rates that deliver only a very small amount of light intensity at any point. A diffusive element may be provided in the light path, for example, to provide some scattering of the laser light, reducing intensity with little or no effect on the quality or utility of the projected image. Light-emitting diodes (LEDs) or other low-power solid-state illumination sources could alternately be used, such as organic LED (OLED) devices.

The image that is projected by projector 40 (FIGS. 7A and 7B) may have image content that is any of a number of forms and may include both aim indicia 12 for the x-ray source and position 42 indicator for detector 20. Alternately, where aim indicia 12 are already provided by the x-ray system, projector 40 may only provide a projection showing position 42. Because projector 40 employs a two-dimensional imaging device, the displayed image can have multiple parts and may include additional text fields, direction markers, and other elements. Position 42 may be shown in outline form, as shown in FIGS. 7A and 7B, or may be represented in some other way. In one example embodiment, the value of angular offset of detector 20 is indicated on the patient's cheek as a displayed numerical message. Alternately, animation or other capabilities of projector 40 may be used to provide, as image content, additional position and angle information.

Color may be used to help indicate the relative amount of alignment offset in various ways. For example, even with the outline of detector 20 projected on the cheek surface, it can be difficult for the technician to know how to adjust for angular alignment. Display of indicia 12 and position 42 in different colors may help to guide the technician in adjusting the angle of the x-ray tube until both aim indicia 12 and position 42 display in the same color, for example. Blinking of the display or of different portions of the displayed elements may also help to indicate and guide alignment adjustments. An audible beep may be provided to indicate acceptable or unacceptable alignment. Stationary indicators, such as arrows or target symbols may be projected as image content onto the cheek of the patient. Animation may be provided to guide adjustment.

In one example embodiment of the present invention, the projected image from projector 40 (FIG. 7B) instructs the technician on how to re-aim x-ray source 10 or how to adjust the position of the treatment chair in order to set up for the next image in the sequence. Projected color, patterning, alphanumeric text, animation, flashing or blinking, or other mechanism may be used to guide positioning adjustment between image captures.

A patient head support apparatus is provided in order to stabilize head position during the tomosynthesis image acquisition cycle. It should be noted that any type of headrest or other support mechanism cannot be metal or other highly radio-opaque material. The patient head support apparatus may be donut-shaped, expandable, or inflatable, for example.

Collimation

For select method and/or apparatus example embodiments, collimation is needed in order to constrain the radiation field to the region of interest (ROI) within the patient's mouth. One beneficial aspect of collimation relates to eliminating or reducing cone-cutting, in which excess radiation from the projected x-ray is incident on areas outside the region of interest.

A difficulty with distributed source arrangements such as CNT arrays relates to the need for appropriate collimation of the radiation. Among its functions, collimation controls the spread of radiation energy so that radiation is appropriately directed to the anatomy of interest and that the radiation field does not extend beyond the outer edges of the imaging receiver. Collimation also helps to reduce scatter. With CNT and other types of small x-ray sources in an array, collimation presents particular challenges. One set of problems relate to dimensional constraints. Because the spacing between x-ray sources is typically small, it can be difficult to effectively isolate the radiation energy from any individual source; crosstalk can occur, making it difficult to clearly define edges of the radiation field. Still other complexity relates to identifying the radiation field for imaging from each source. With conventional radiography sources, the problem is readily solved: a light source that is coupled to the radiography source can be used to outline or otherwise highlight the radiation field, using the collimator edges themselves to outline the extent of the radiation field. However, it may be impractical or impossible to provide the corresponding dual-use arrangement using collimator openings provided for CNT and other types of distributed array sources.

Figure 8:
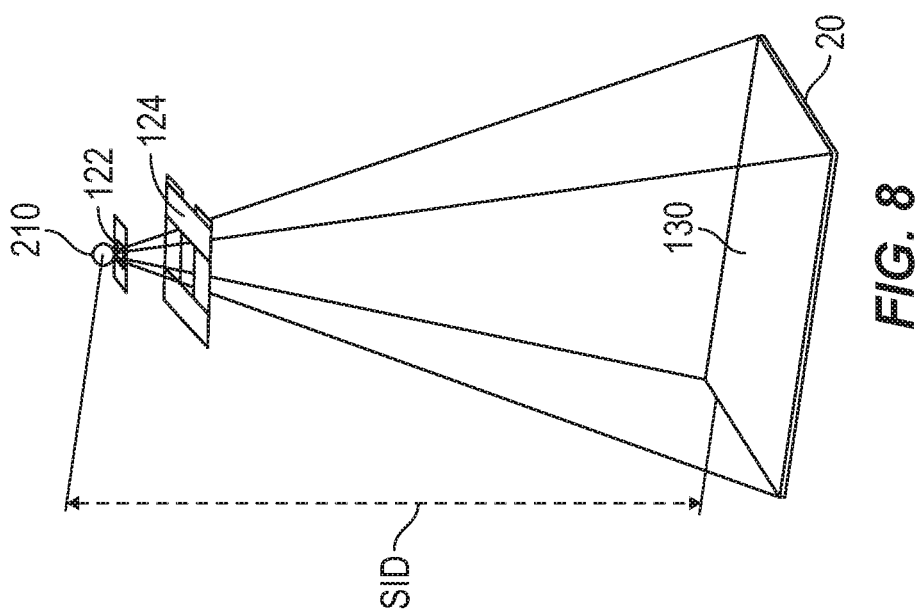
FIG. 8 displays a radiation source assembly with collimation in a substantially square arrangement.

The simplified schematic view of FIG. 8 shows some of the geometric considerations and relationships that relate to x-ray collimation for a single x-ray source 210 in general and establish some definitions useful in subsequent description of collimation for an array of x-ray sources. X-ray source 210 is idealized as a point source, to a first approximation. Radiant energy from source 210 is directed along a radiation path that extends through a first aperture 122 that is typically very close to source 210 and may even be optional under some conditions for very small x-ray sources. The radiant energy then continues along the radiation path through a second aperture 124 that shapes an x-ray field 130 on a detector 20. The shape and dimensions of the radiation path that determine the aspect ratio of x-ray field 130 are then determined by the geometric constraints such as aperture 122, 124 size and location relative to the source 210 and to each other and source-to-image distance (SID). The shape of x-ray field 130 is typically bounded by the dimensions of detector 20 but may be smaller and of a different shape, depending on the anatomy being imaged.

Scan Sequence for Tomosynthesis Imaging

The alignment apparatus that is provided by the triangulation sensing apparatus of FIG. 6A or 6B may be used to assist in capturing a series of images of the same tooth or other structure, taken in quick succession and each at a slightly different angle, for forming a limited-angle volume image. As noted in the background section above, this type of volume imaging may have diagnostic value and advantages over a single x-ray image, but without requiring the expense and dose requirements of full-fledged CBCT imaging. In addition, unlike with CBCT imaging, the limited-angle volume image can be acquired with the patient seated in the treatment chair.

Figure 9:
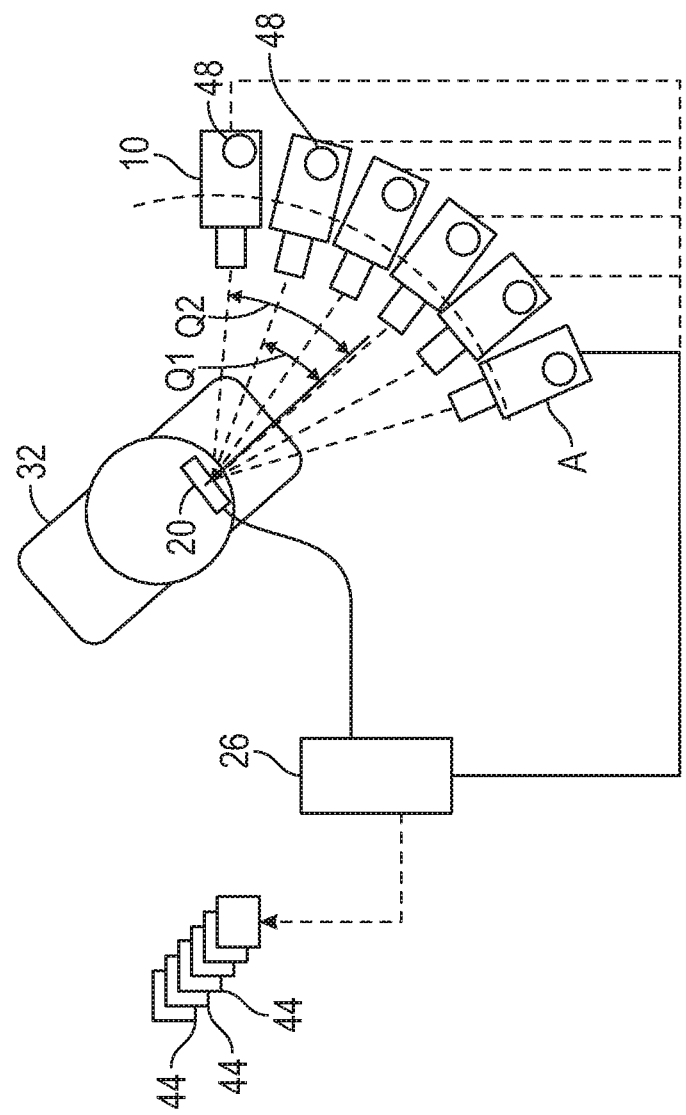
FIG. 9 is a schematic block diagram that displayes an imaging pattern used for obtaining a layers/volume image from a limited number of x-rays.

Referring to FIG. 9, there is shown, from a top view, a schematic block diagram of an imaging pattern used for obtaining a limited-angle volume image from a patient 32 using a limited number of x-rays from a single source 10 and a digital detector. X-ray source 10 is used to direct exposure to detector 20 from a number of angular orientations, shown as capture or exposure angles in FIG. 9, along a non-linear, curved or arcuate path A. At each of two or more exposure angle positions, with two called out by way of example as angles Q1 and Q2 in FIG. 9, radiation energy is directed to detector 20 and the corresponding image data from the digital detector obtained by control logic processor 26 and stored as a component or projection image 44, indexed according to the relative acquisition geometry for the image, such as by the exposure angle orientation. In this way, one component image 44 is obtained and stored for each exposure angle. Control logic processor 26 can then generate a volume image as a composite image, using the combined data from the individual component projection images 44.

It should be noted that the pattern traced by changes in the relative position of the x-ray emitter to the detector, as shown in the top view of FIG. 9 for example, can be linear or curved.

Additional sensing components and logic associated therewith are used to provide positional and angular information about each image that is obtained. In one example embodiment, for example, fixed positional and angular coordinates are assigned to an initial spatial position and angular orientation of x-ray source 10. Then, system logic records the changed position and angle that correspond to each imaging position in the series of images that are obtained. This data then provides the needed reference geometry for reconstruction of the 3-D volume image from a series of 2-D image captures. Spatial position data can be obtained in a number of ways, such as using an angular sensor 48 that is coupled with a gantry or other transport apparatus that is used for movement of x-ray source 10, for example.

In order for this type of limited-angle volume imaging to work correctly, the angular orientation and spatial arrangement of x-ray source 10 relative to detector 20 must be known for each projection image acquired throughout the imaging cycle so that the component data that is obtained can be properly aligned and correlated between projection images. For the embodiment shown in FIG. 9, the head of patient 32 and spatial position of detector 20 are rigidly fixed in position while x-ray source 10 is moved orbitally from one relative angular orientation to the next. It may be necessary to mechanically fix the spatial position of detector 20 relative to the subject that is being imaged. With respect to FIG. 9, for example, one or more bite blocks or a clip-on device may be useful for rigidly fixing detector 20 at a position within the mouth of patient 32.

In practice, it may be impractical to translate a conventional x-ray head over an arc in order to acquire projection images as shown schematically in the top view of FIG. 9. Example embodiments of the present invention address the difficulty of source movement by providing an enclosure that accurately fixes components in space and that has the positional geometry needed for exposure in acquiring projection images for tomosynthesis.

Figure 10A:
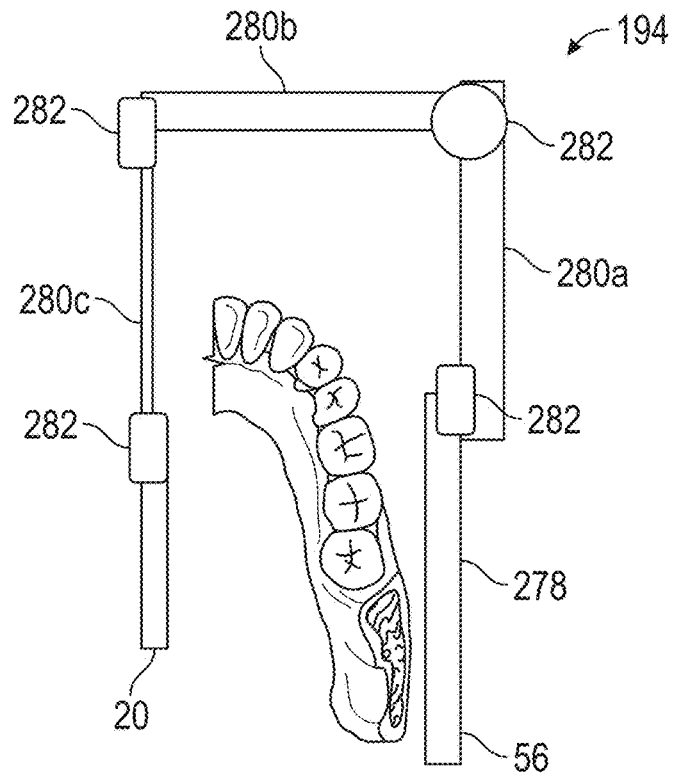
FIGS. 10A and 10B are top view schematic diagrams that display a frame having multiple articulated sections at each adjustable joint for reporting sensed extension and rotation data.

The schematic top view of FIG. 10A shows a frame 278 of an example embodiment for rigidly fixing detector 20 position within the mouth. Frame 278 has multiple articulated sections 280a, 280b, 280c with an encoder 282 at each adjustable joint for reporting sensed extension and rotation data. This arrangement provides a positioning apparatus 194 that allows resizing for the patient and provides repositioning of detector 20 relative to collimator 56, with sensed data available for correlating component positions relative to a reference position and relative to each other. Alternately, an accelerometer or electromagnetic, magnetic, or radio-frequency (RF) sensing may be provided and used as positioning apparatus 194 for correlating detector 20 position to the secondary collimator 56 and relating these positions to the position of the x-ray source at any acquisition angle in a tomosynthesis sequence.

An example embodiment of the present invention provides an apparatus for dental tomosynthesis imaging in which an enclosure provides the components that generate and shape the x-ray path, as well as providing geometric calibration information that may be detected in each acquired radiographic image. The enclosure includes the x-ray source, or array of x-ray sources, including a first collimator for initial shaping of the emitted radiation, a second collimator for further definition of the radiation beam, and a phantom that is coupled to the second collimator and provides geometric calibration information in each acquired 2-D projection image. According to an example embodiment using a single x-ray source, the enclosure also provides a translation apparatus with an actuator that translates the position of the x-ray source along a translation path in order to provide radiation over the range of angles needed for tomosynthesis imaging. The combination of source, calibration phantom, and first and second collimators cooperates to constrain the radiation field to the detector position during exposure and image acquisition needed for tomosynthesis imaging.

Figure 10B:
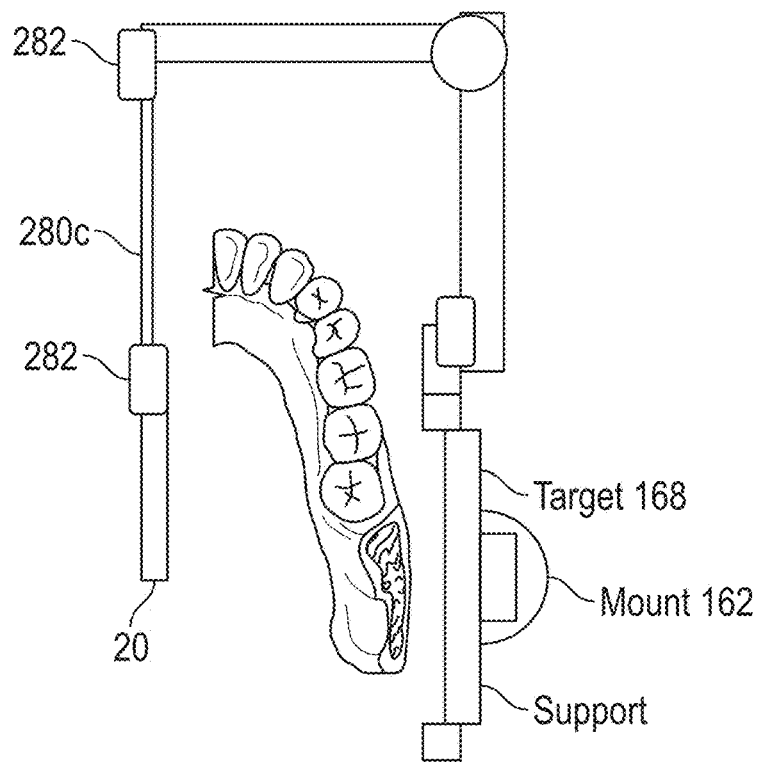
Figure 10C:
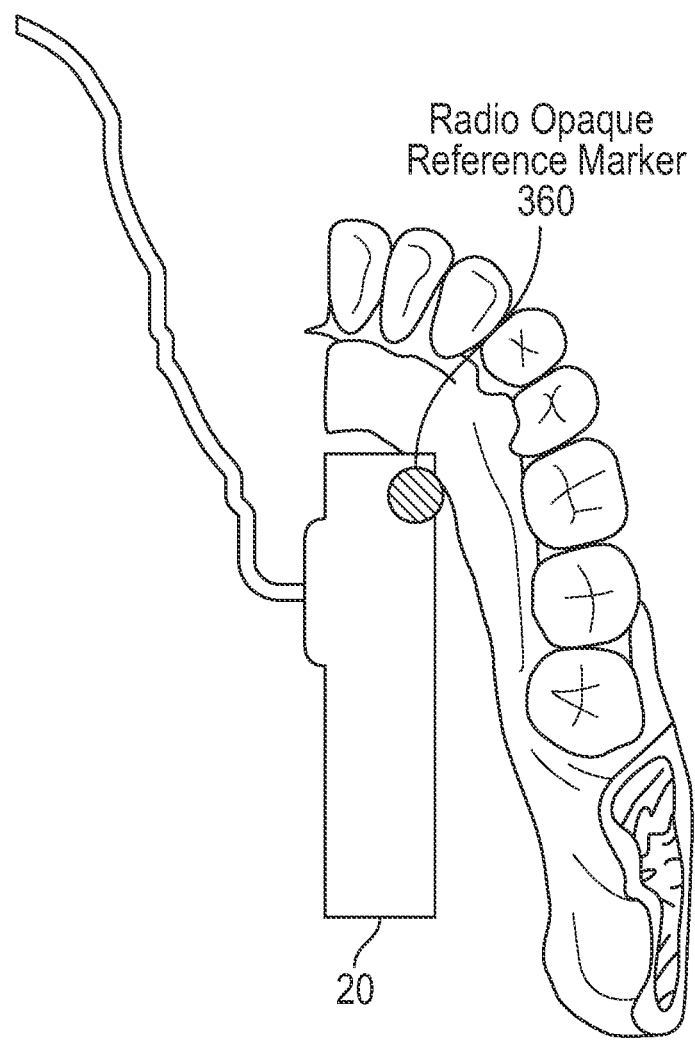
FIG. 10C is top view schematic diagram that displays a detector not coupled to a frame and with an embedded radio-opaque reference marker on the margin of an imaging area.

An example embodiment of the present invention may use the frame 278 of FIG. 10A or other similar support for positioning detector 20 relative to the enclosure and second collimator 56. FIG. 10B shows an alternate example embodiment in which frame 278 does not include the collimator, but instead has a target aperture 168 for coupling with an enclosure as described below. Frame 278 may also have a mount 162 that is coupled to the dental chair or other accessory.

An example embodiment of the present invention may also completely avoid using the frame 278 of FIG. 10A by using a radio-opaque marker embedded in a detector. In conjunction with a marker attached to the collimator of the x-ray source assembly, this provides a way to determine the x-ray beam focus to the detector by recovering source geometry via image features.

Figure 11:
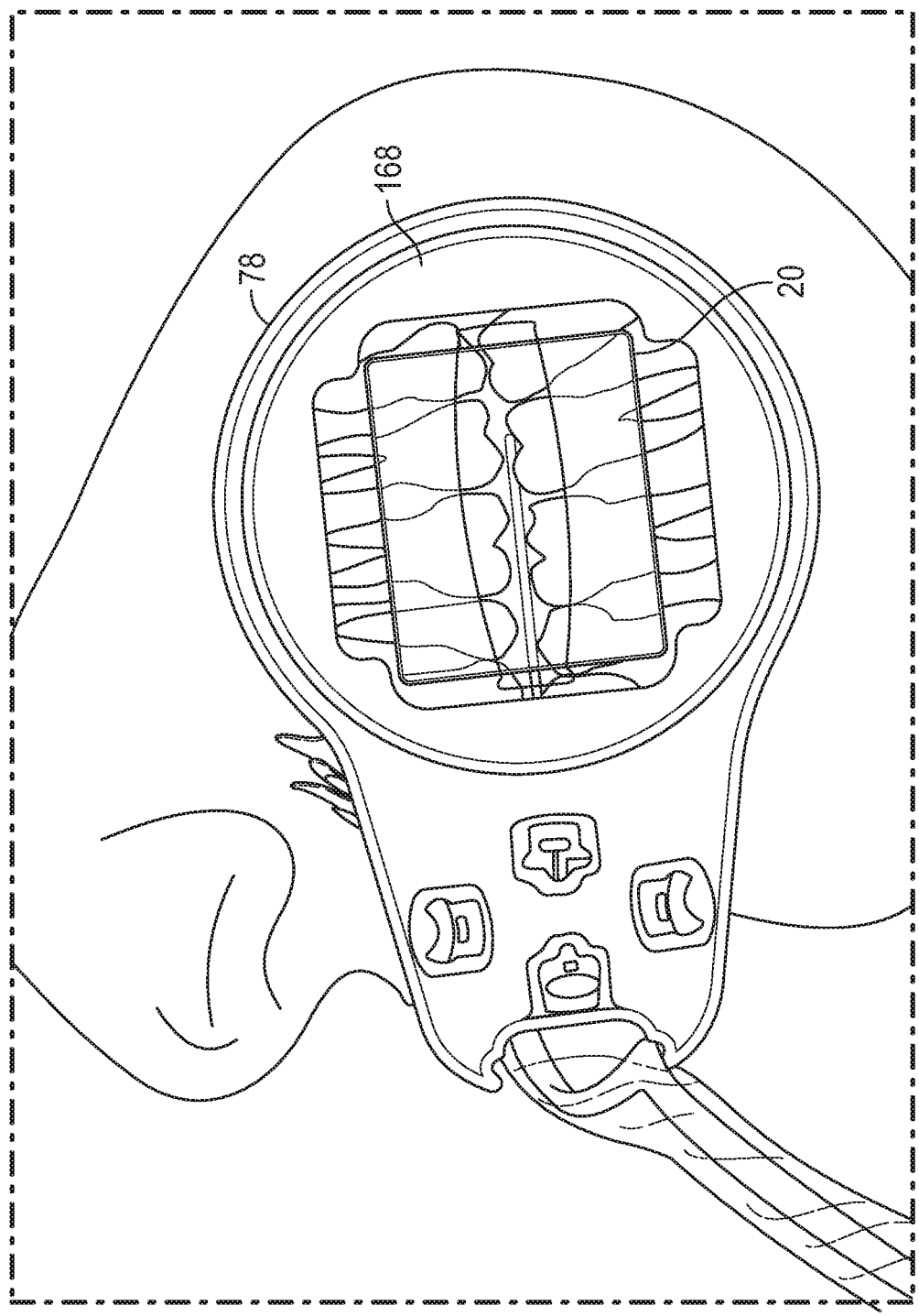
FIG. 11 displays a position of a frame against a patient's face for alignment and collimation support.

The enlarged side view of FIG. 11 shows, in schematic form, a frame 78 having target aperture 168. Positioning apparatus 194 maintains target aperture 168 in position so that it is effectively centered about detector 20 that is held within the patient's mouth. According to the example embodiment shown in FIG. 11, target aperture 168 is a ring aperture.

Phantom for Geometric Calibration

Figure 12:
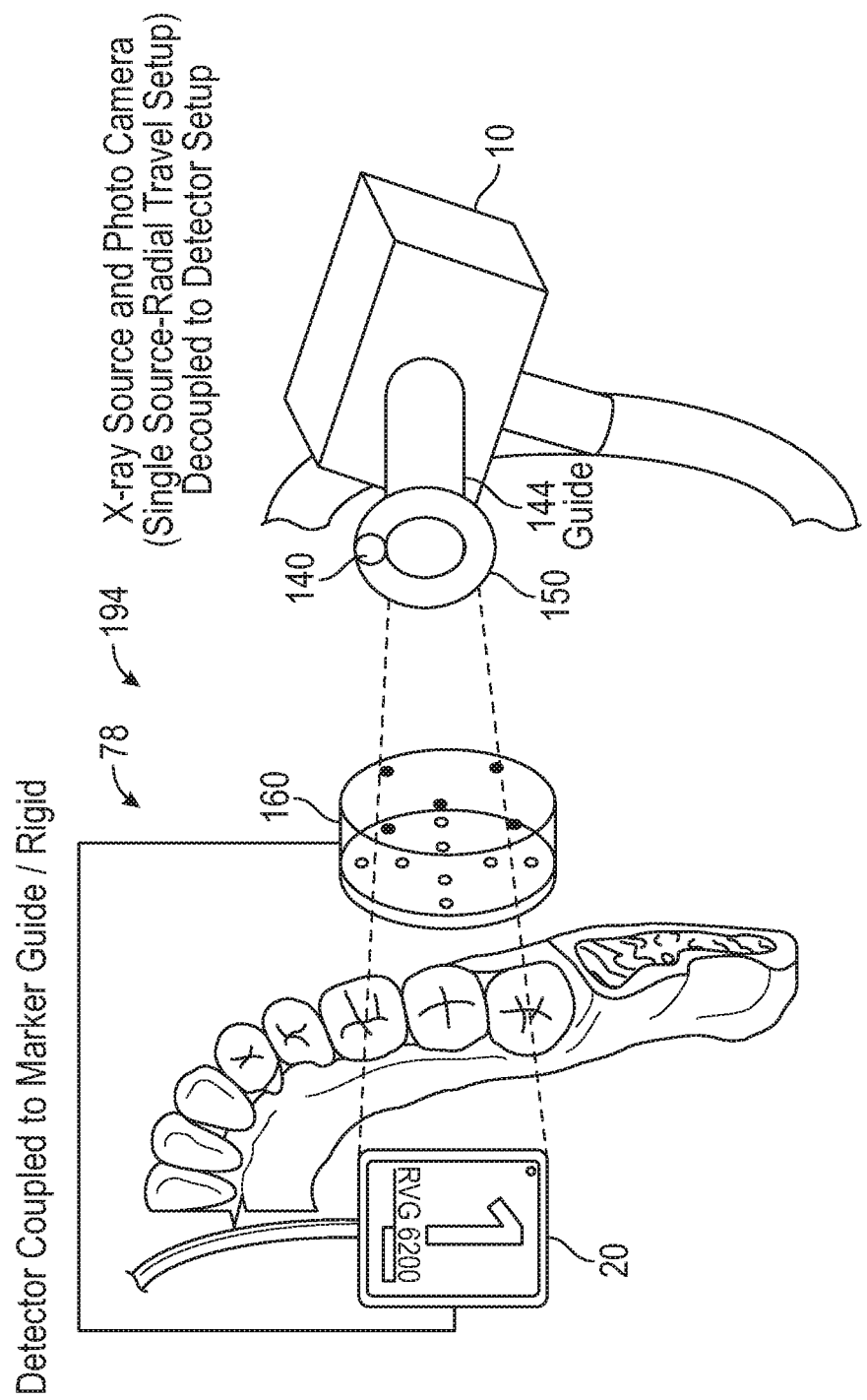
FIG. 12 is a schematic diagram that displays the use of a geometric calibration phantom that is coupled with the intraoral detector.

According to an example embodiment of the present invention, as shown in FIG. 12, a geometric calibration phantom 160 is positioned in the radiation path, coupled to the secondary collimator 150, as described in more detail subsequently. An optional guide 144 is shown as part of source 10.

The schematic diagram of FIG. 12 shows the use of an example calibration phantom 160 that is disposed in the radiation path. Calibration phantom 160 provides a number of functions that assist in alignment and collimation for the x-ray source 10 and relate the spatial position of the intraoral x-ray detector to the position of x-ray source 10. An optional camera 140 may be used for sensing markers associated with phantom 160 that are radio-transparent.

When using phantom 160, radio-opaque markers therein provide information on the location of the source relative to the detector in the image content of the 2-D projection images, preferably around the edge of the FOV. Additional radio-transparent optical markers may also be provided for viewing under visible or infrared illumination using optional camera 140. The radio-transparent optical markers may aid in alignment of the source to the detector as well as in collimator positioning. Radio-transparent optical markers may have a 3-D orientation that allows the location of the source relative to the detector can be determined from camera, reflectance or optical image content, which can be sequentially or simultaneously obtained relative to the x-ray image content.

Phantom Composition

Figure 13A:
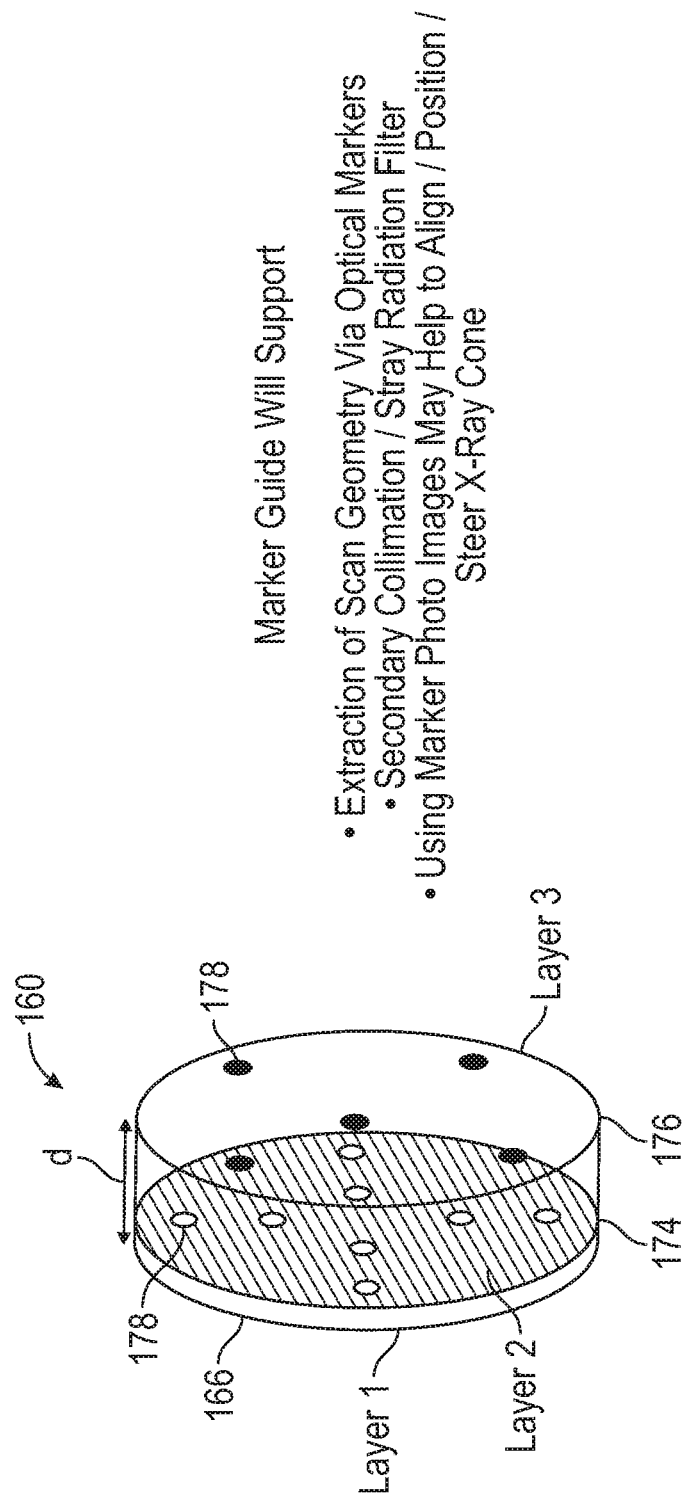
FIGS. 13A and 13B display features of a geometric calibration phantom.
Figure 13B:
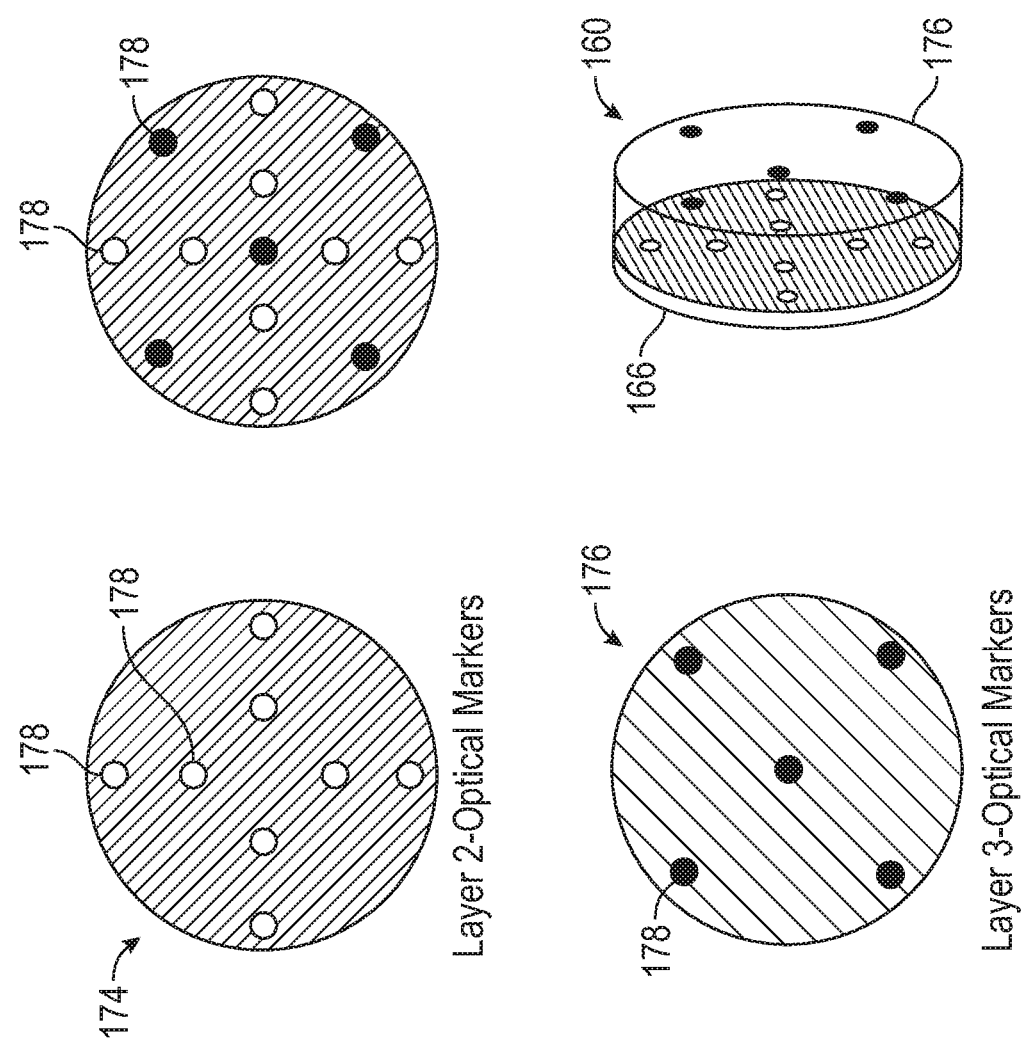

FIGS. 13A and 13B show the assembly and components of geometric calibration phantom 160 according to method and/or apparatus example embodiments of the present invention. FIG. 13A shows an example calibration phantom 160 as assembled and having a number of planar layers. FIG. 13B shows layered components for forming calibration phantom 160. Layer 1 166 can be positioned in close contact with the face of the patient. Layer 2 174 and layer 3 176 can provide optional optical markers 178 as well as radio-opaque markers 178 for assisting in extraction of scan geometry for alignment. Separation of layers 174, 176 by a distance, d, helps to facilitate alignment measurement. Markers 178 may have an overlaid arrangement shown in FIG. 13B and may be sensed by an optional camera 140 (FIG. 12), with the resulting image processed for obtaining alignment data. Markers 178 may be different shapes (e.g., non-symmetric), layers, 3-D configurations, or colors to support alignment detection when using a camera. One or more of markers 178 can be radio-opaque to support alignment detection from the projection image.

Figure 14A:
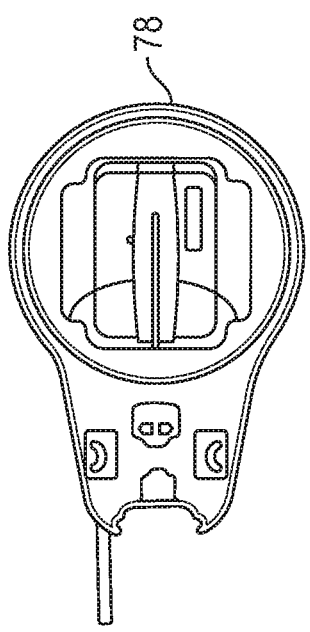
FIG. 14A displays components of a frame that stabilizes and provides a reference for an intraoral detector.

FIG. 14A shows side and top views of frame 78 and associated components. A bite block 154 helps to stabilize the position of detector 20 within the mouth. An adjustable rod 156 allows positioning of the bite block 154 and detector 20 to suit the patient's comfort. Frame 78 defines target aperture 168 for directing exposure energy to detector 20.

Figure 14B:
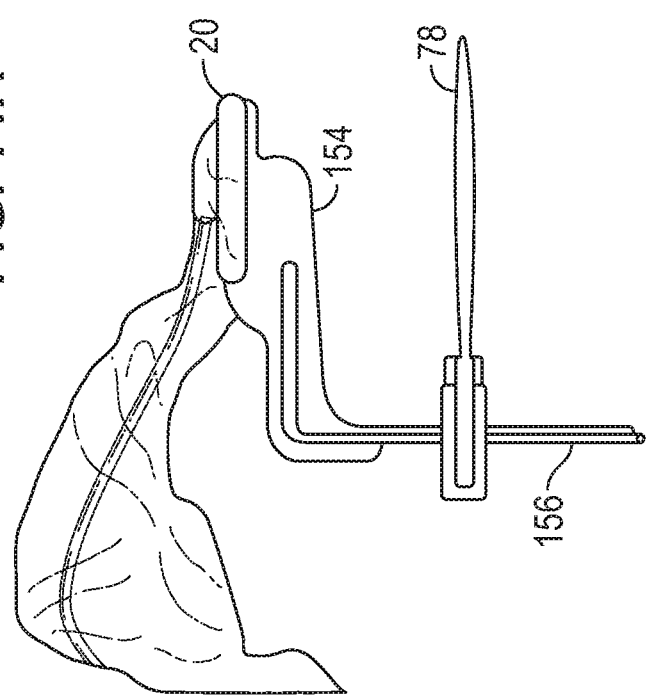
FIG. 14B displays components for source positioning and provides a reference for an intraoral detector via radio-opaque markers embedded both in a collimator of a radiation source assembly and on detector surface.

FIG. 14B shows an alternate arrangement without frame 78 to focus the x-ray beam on the detector using radio opaque markers on the collimator and the detector, without any additional positioner at the patient's mouth. This arrangement uses an image-based method for determining the detector position with respect to the source and directing exposure energy to the detector 20.

Imaging Enclosure Embodiments

An example embodiment of the present invention, as shown for example in FIG. 15, provides an intraoral imaging apparatus 300 for tomosynthesis imaging that has an x-ray source enclosure 310 that is configured to seat against target aperture 168 of the frame, such as using a mechanical or magnetic coupling that fastens x-ray source enclosure 310 to aperture 168. X-ray source enclosure 310 components are arranged to direct a collimated x-ray beam to detector 20 through the target aperture 168 and to compensate for changes in the relative position of the target aperture 168 relative to detector 20.

In the FIG. 15 example embodiment, a single x-ray source 10 is energizable to emit a radiation beam from each of a plurality of focal points, f. Only three focal points, f, are shown for clarity. In practice, a number of focal points, f, would be used for tomosynthesis imaging, such as 12 or 20 or more, for example.

Not shown in FIG. 15, but typically provided with x-ray source 10, whether in an array or in single-source form, as shown, a local collimator, spaced close to the focal point, f, provides a measure of secondary collimation for the emitted beam. X-ray source enclosure 310 provides a primary collimator 320 at an exit end E that is disposed to form a collimated beam from the emitted radiation beam and direct the collimated radiation beam through the target aperture 168 and to the detector 20 as the incident radiation beam. Geometric calibration phantom 160 is adjacent to collimator 320 and is disposed in the path of the collimated beam.

A source transport assembly 330 translates the position of x-ray source 10 to each focal point, f. Source transport assembly 330 has an actuator 332 that is energizable to translate source 10 from one focal point, f, position to the next. At each source position, the source is slightly rotated by actuator to direct the x-ray beam through primary collimator 320 the detector 20. The e x-ray source enclosure 310 is positioned using the target 168 on patient face to obtain the images.

Figure 15A:
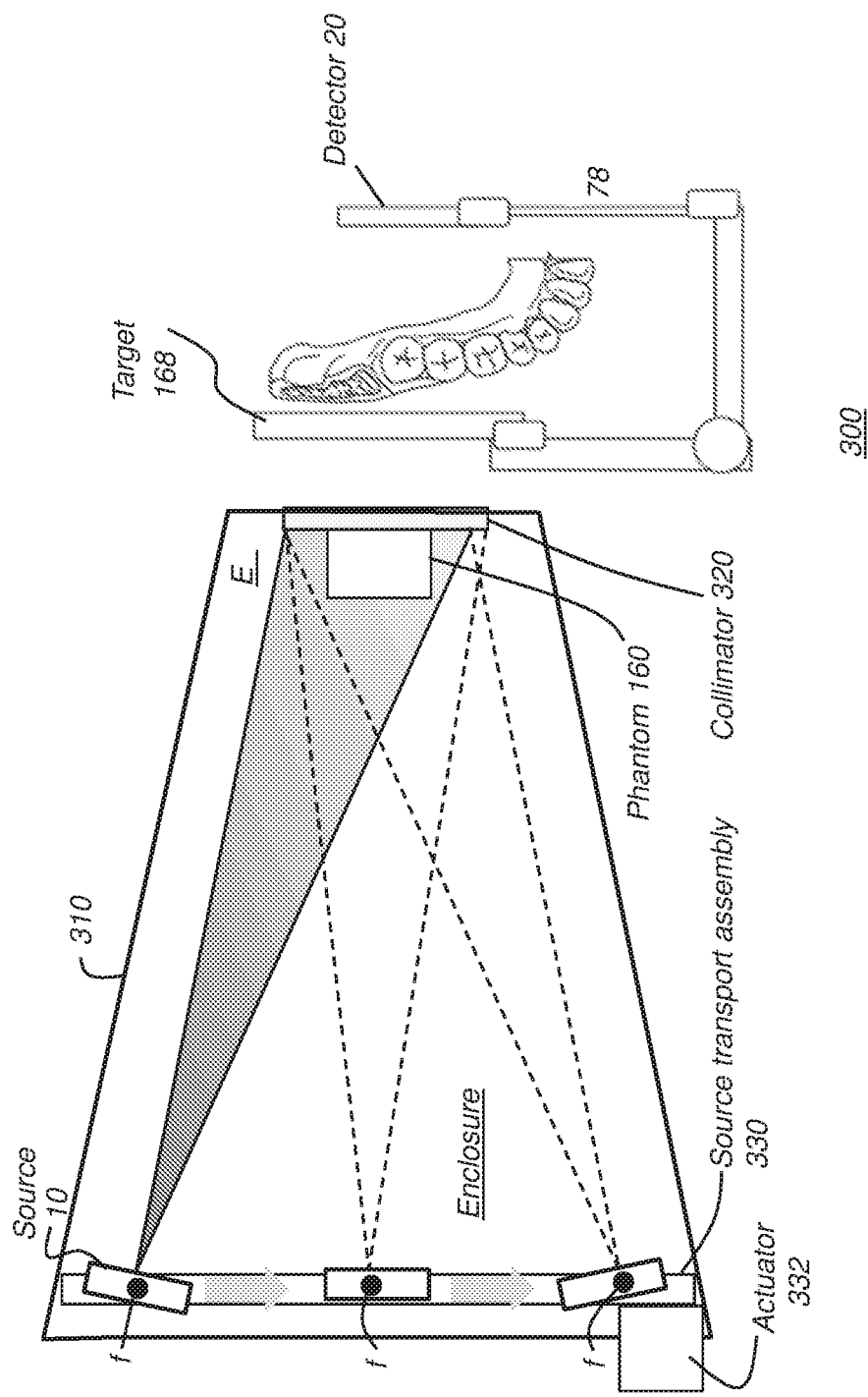
FIG. 15A is a schematic diagram that displays an intraoral apparatus for tomosynthesis imaging with an x-ray source enclosure and a target frame coupled to a detector. A single x-ray source is moved and rotated within the x-ray source enclosure to focus on a collimator and/or detector during imaging.

FIG. 15A is an example embodiment of the present invention, which includes x-ray source enclosure 310 shown in FIG. 15 including the moving and rotating source arrangement by actuator 332 and uses radio opaque reference markers 360 embedded in primary collimator 320 and detector 20. Detection of the reference marker shadows in the captured images is used to automatically steer the x-ray source enclosure 310 to accurate positions on the desired anatomy.

Figure 15B:
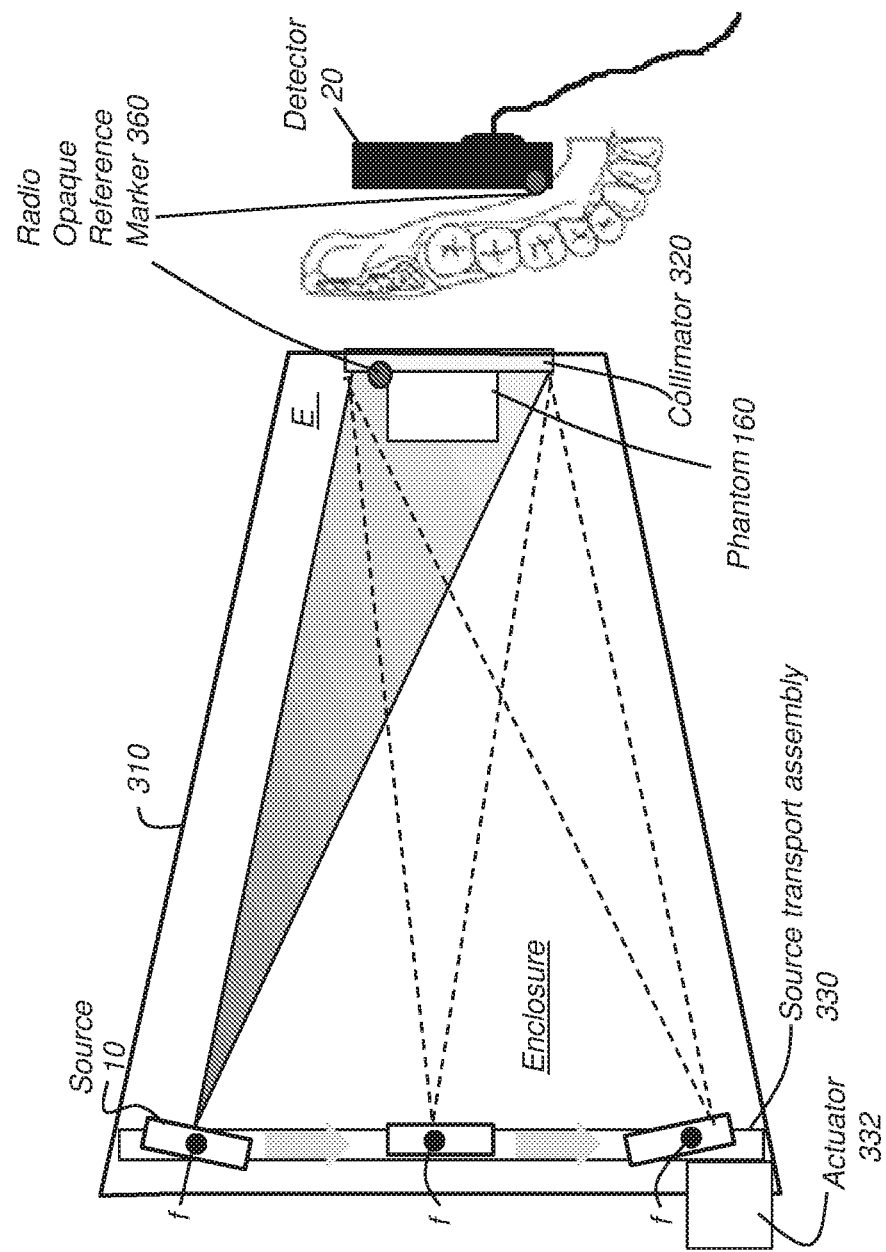
FIG. 15B is a schematic diagram that displays an intraoral apparatus for tomosynthesis imaging with an x-ray source enclosure and a detector without a target frame using radio-opaque reference markers to position an x-ray source with respect to the detector. The x-ray source is moved and rotated within the x-ray source enclosure to focus on a collimator and/or detector during imaging.

FIG. 15B is an example embodiment of the present invention, where a single x-ray source 10 is moved in a linear path by actuator 332 and directs the x-ray beam directly to target 168. The x-ray source enclosure 310 and rolling shutter collimator 325 block any x-ray beam not directed to the detector 20. In addition, source transport assembly 330 provides a measure of rotation in order to direct the emitted radiation beam through collimator 320 to detector 20. A control logic processor 340, such as a controlling computer or dedicated microprocessor or similar control logic apparatus, is configured to execute programmed instructions for driving the collimator translation apparatus in synchronization with emission from each of the plurality of focal points. X-ray source enclosure 310 is positioned using the target 168 on the patient's face to obtain the images.

Figure 15C:
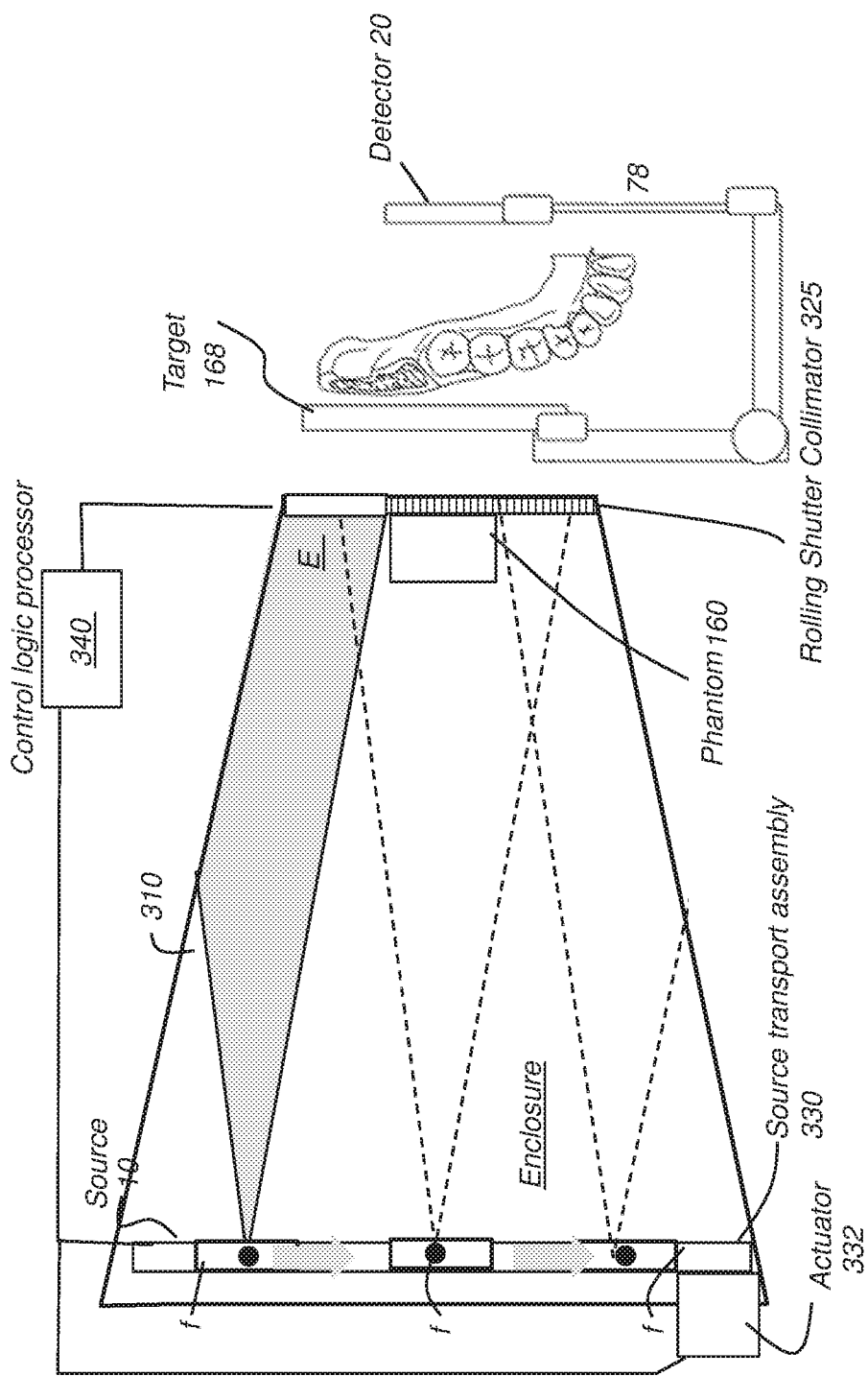
FIG. 15C is a schematic diagram that displays an intraoral apparatus for tomosynthesis imaging with an x-ray source enclosure and a target frame coupled to a detector. The x-ray source enclosure includes a rolling shutter for collimation. A single x-ray source is moved in a linear path within the x-ray source enclosure.

FIG. 15C is an example embodiment of the present invention in which single x-ray source 10 is moved in a linear path by actuator 332 and directs the x-ray beam to primary collimator 325. The x-ray source enclosure 310 and rolling shutter collimator 325 block any x-ray beam not directed to the detector 20. In addition, source transport assembly 330 provides a measure of rotation to direct the emitted radiation beam through collimator 320 to detector 20. A control logic processor 340, such as a controlling computer or dedicated microprocessor or similar control logic apparatus, is configured to execute programmed instructions for driving the collimator translation apparatus in synchronization with emission from each of the plurality of focal points. The radio opaque reference markers 360 embedded in primary collimator 320 and detector 20 are used to automatically steer x-ray source enclosure 310 to accurate positions on the desired anatomy by detection of the reference marker shadows in the captured images.

Figure 15D:
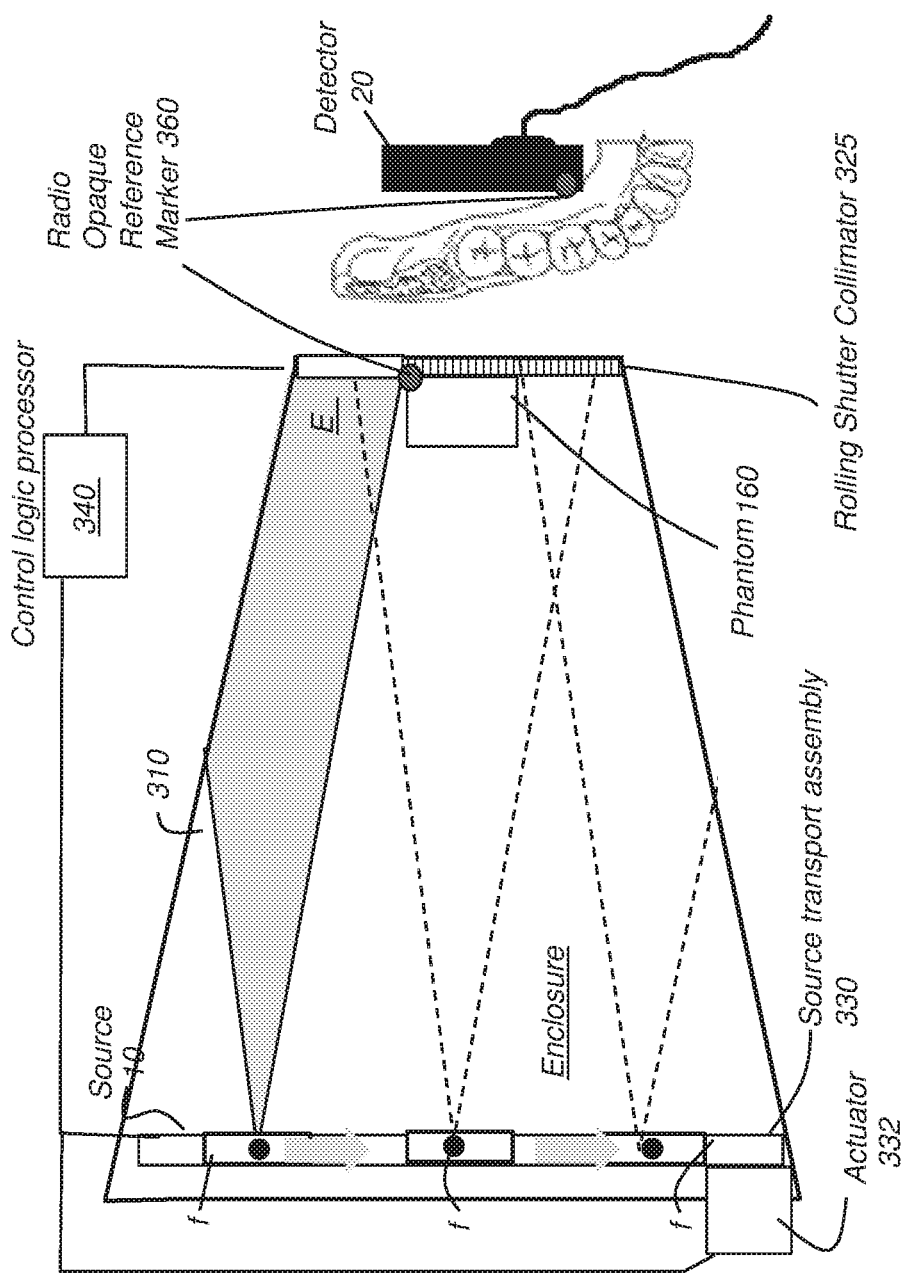
FIG. 15D is a schematic diagram that displays an intraoral apparatus for tomosynthesis imaging with an x-ray source enclosure and a detector without a target frame using radio-opaque reference markers to position an x-ray source with respect to the detector. The x-ray source enclosure includes a rolling shutter for collimation. The x-ray is source is moved in a linear path within the x-ray source enclosure.

FIG. 15D is an example embodiment of the present invention in which an array of stationary sources 11 replaces the single source movement by actuator shown in FIG. 15B. X-ray source enclosure 310 is positioned using the target 168 on the patient's face to obtain the images.

Figure 15E:
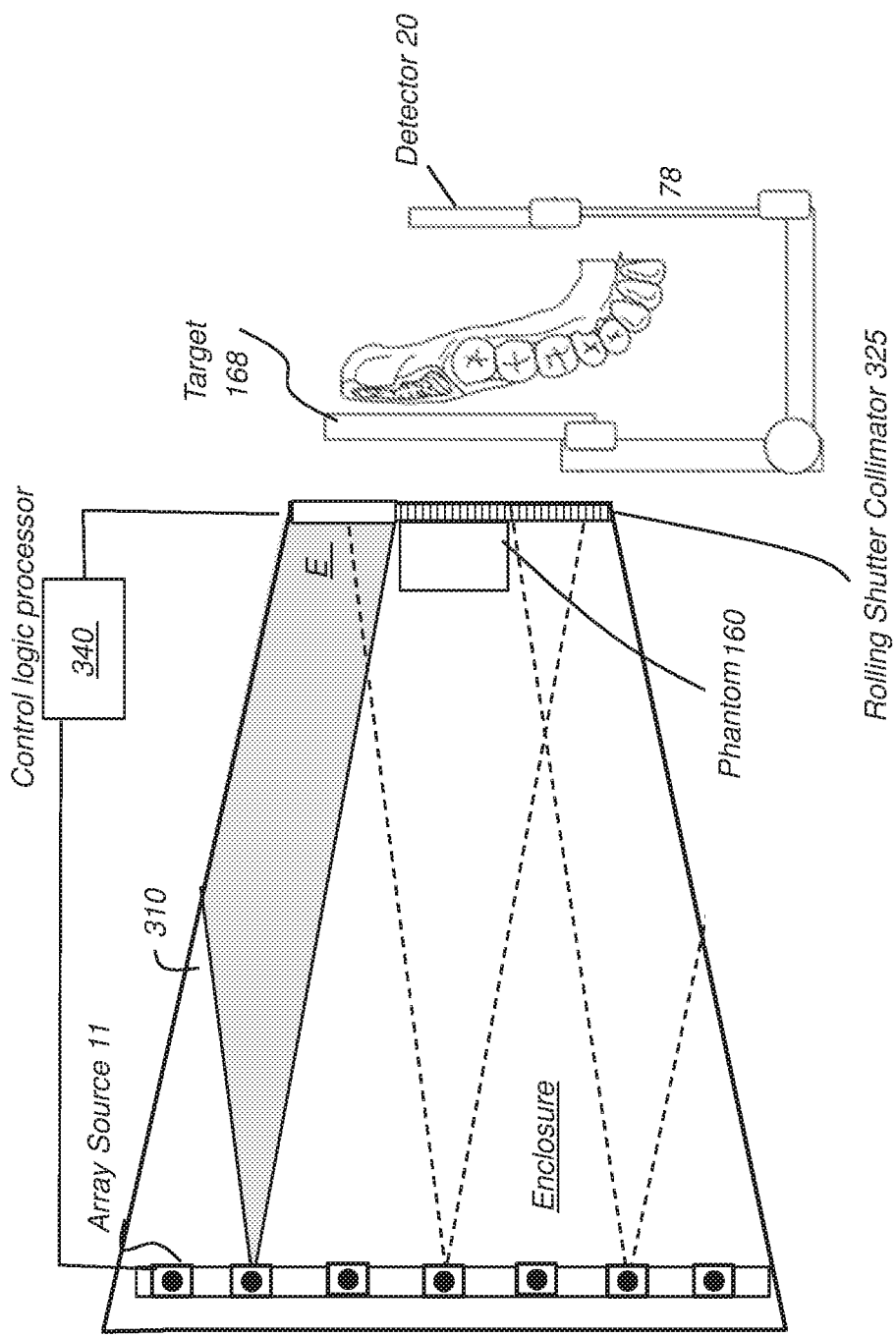
FIG. 15E is a schematic diagram that displays an intraoral apparatus for tomosynthesis imaging an x-ray source enclosure and a target frame coupled to a detector. The x-ray source enclosure includes a rolling shutter for collimation and multiple x-ray sources in a fixed linear array configuration.

FIG. 15E is an example embodiment of the present invention in which an array of stationary sources 11 replaces the single source movement by actuator in FIG. 15C. The radio opaque reference markers 360 embedded in primary collimator 320 and detector 20 are used to automatically steer x-ray source enclosure 310 to accurate positions on the desired anatomy by detection of the reference marker shadows in the captured images.

Figure 15F:
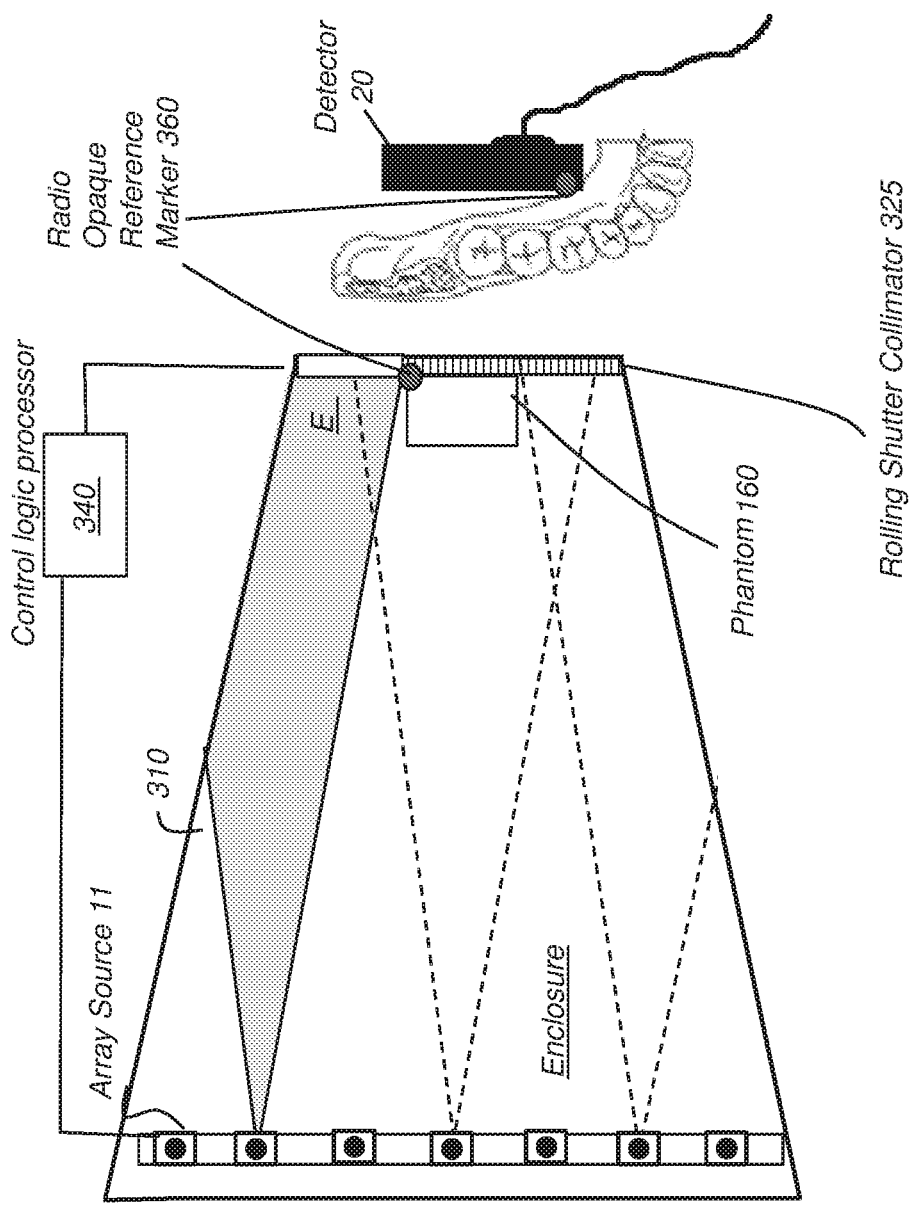
FIG. 15F is a schematic diagram that displays an intraoral apparatus for tomosynthesis imaging with an x-ray source enclosure and a detector without a target frame using radio-opaque reference markers to position an x-ray source with respect to the detector. The x-ray source enclosure includes a rolling shutter for collimation and multiple x-ray sources in a fixed array configuration.

FIG. 15F is an example embodiment of the present invention in which a panel (2D array) of stationary sources 11a replaces the single source movement by actuator in FIG. 15B. X-ray source enclosure 310 is positioned using the target 168 on patient face to obtain the images.

Figure 15G:
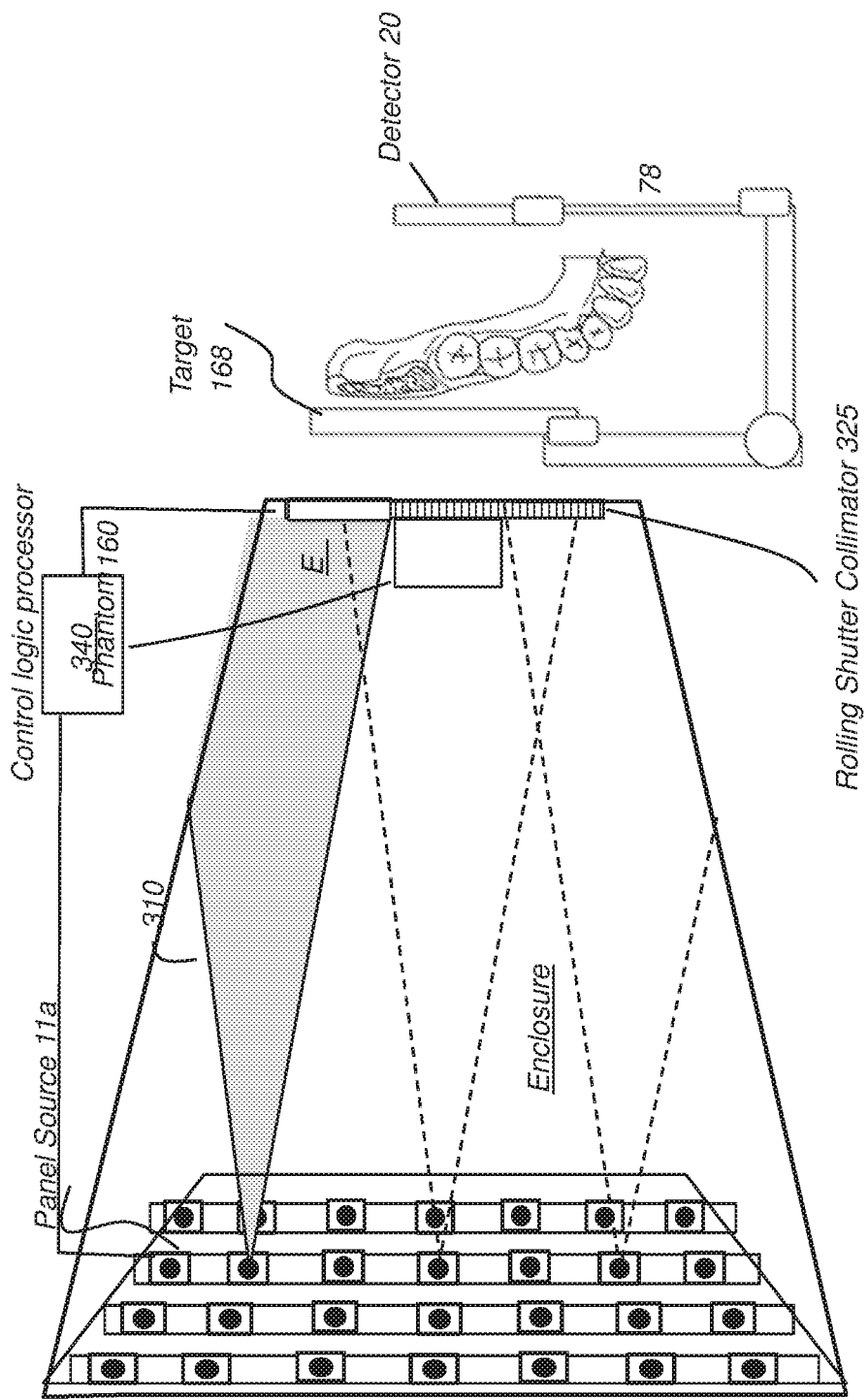
FIG. 15G is a schematic diagram that displays an intraoral apparatus for tomosynthesis imaging an x-ray source enclosure and a target frame coupled to a detector. The x-ray source enclosure includes a rolling shutter for collimation and multiple x-ray sources in a fixed 2-D panel.
Figure 15H:
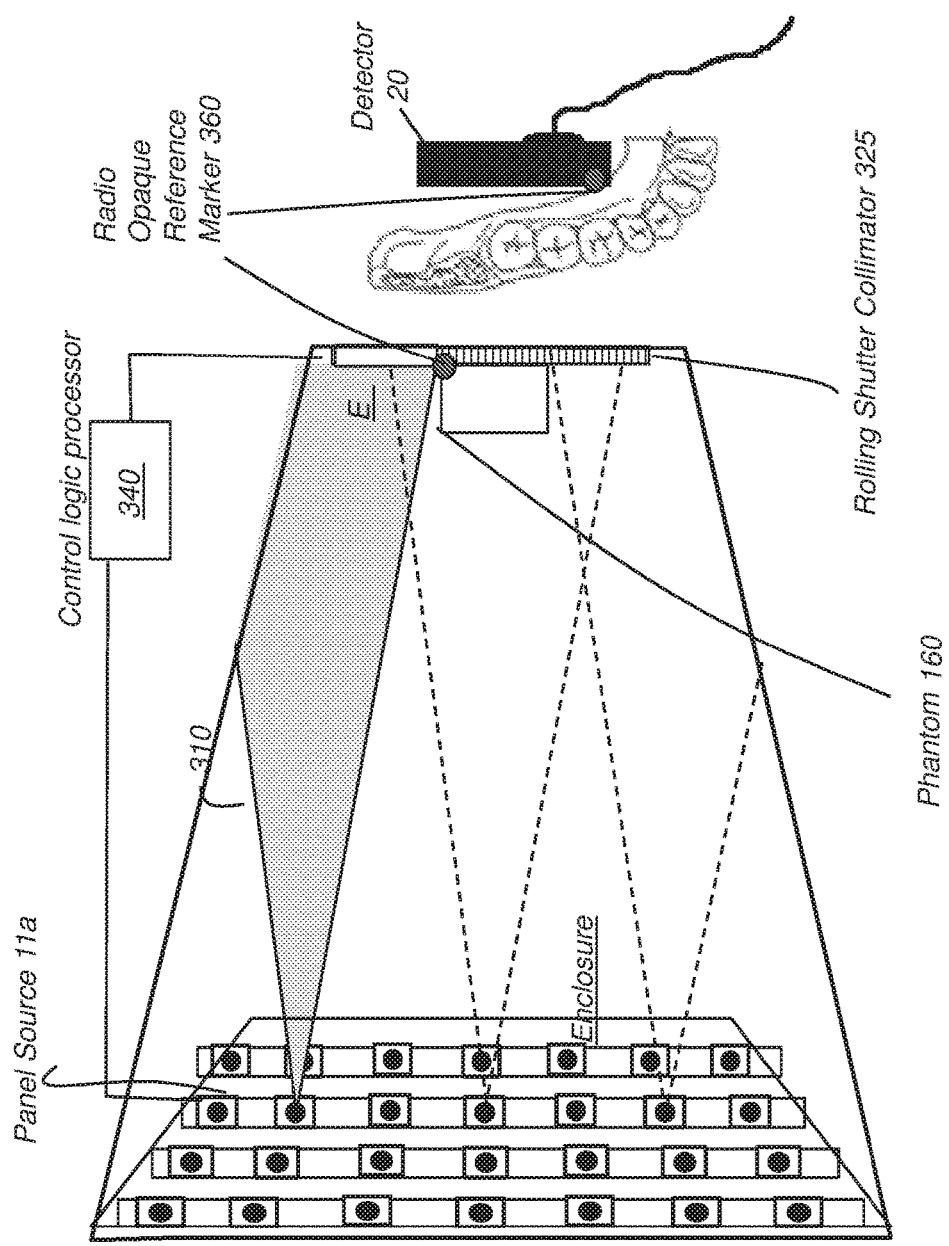
FIG. 15H is a schematic diagram that displays an intraoral apparatus for tomosynthesis imaging with an x-ray source enclosure and a detector without a target frame using radio-opaque reference markers to position an x-ray source with respect to the detector. The x-ray source enclosure includes a rolling shutter for collimation and multiple x-ray sources in a fixed 2-D array.

FIG. 15G is an example embodiment of the present invention in which a panel (2D array) of stationary sources 11a replaces the single source movement by actuator in FIG. 15C. The radio opaque reference markers 360 embedded in primary collimator 320 and detector 20 are used to automatically steer x-ray source enclosure 310 to accurate positions on the desired anatomy by detection of the reference marker shadows in the captured images.

Figure 16A:
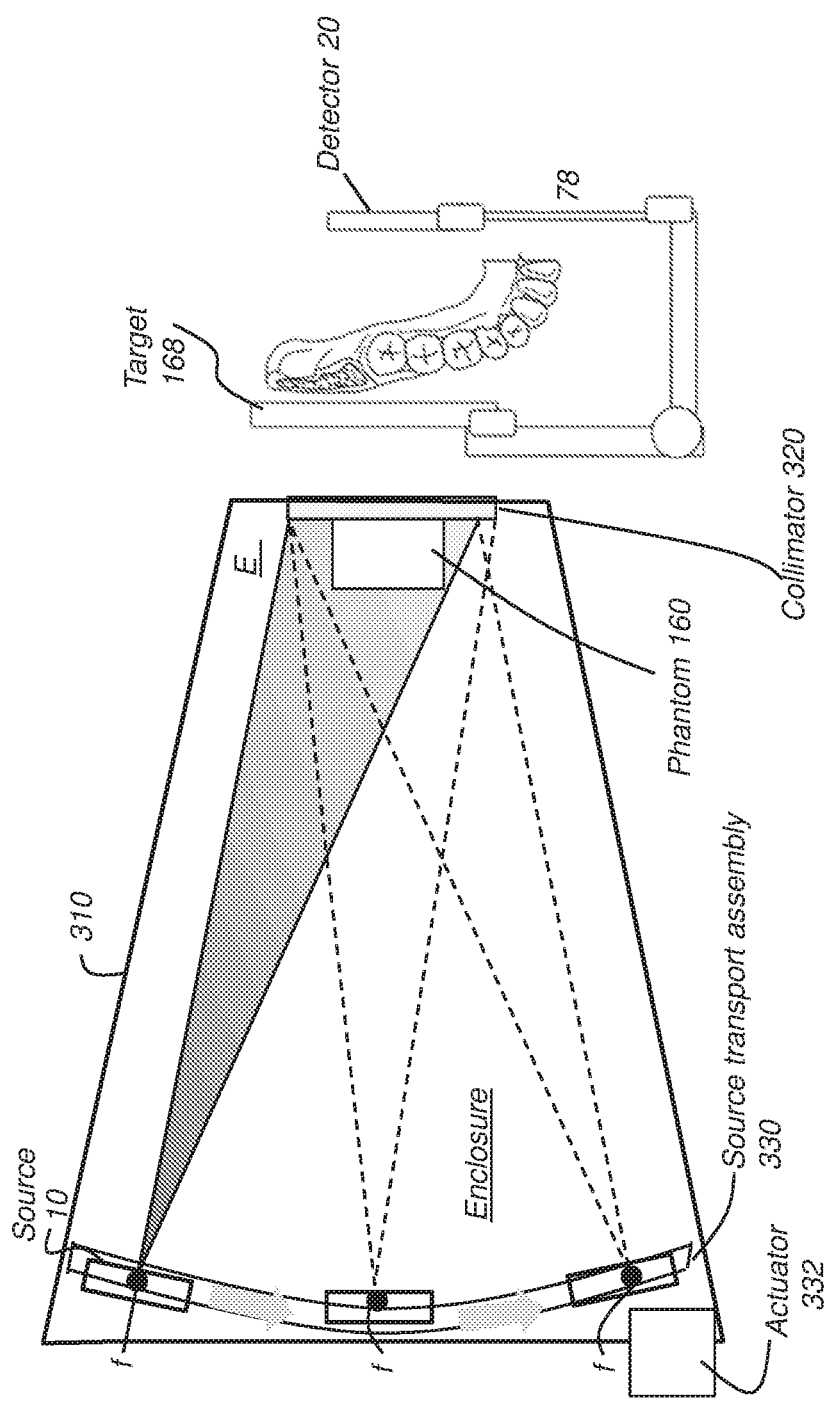
FIG. 16A is a schematic diagram that displays an intraoral apparatus for tomosynthesis imaging including an x-ray source enclosure and a target frame coupled to a detector. The x-ray source enclosure includes a fixed collimator and a single x-ray source translated in an arcuate path.

FIG. 16A shows an alternate example embodiment according to the present invention in which the transport path provided by transport assembly 330 for source 10 is curved, obviating the need to rotate the source 10 as in the FIG. 15 embodiment.

Figure 16B:
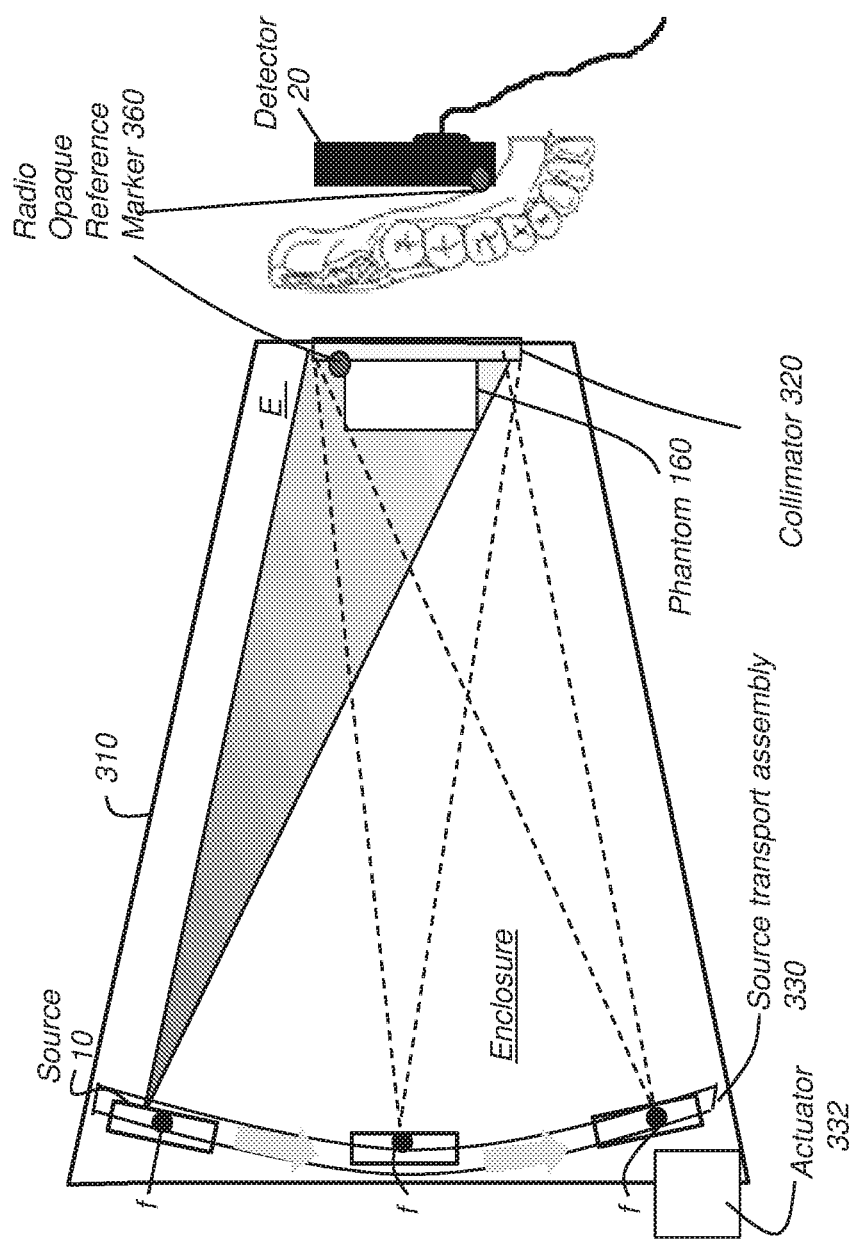
FIG. 16B is a schematic diagram that displays an intraoral apparatus for tomosynthesis imaging with an x-ray source enclosure and a detector without a target frame using radio-opaque reference markers to position the x-ray source with respect to the detector. The x-ray source enclosure includes a fixed collimator and a single x-ray source translated in an arcuate path.

FIG. 16B shows an alternate example embodiment according to the present invention in which the transport path provided by transport assembly 330 for source 10 is curved, obviating the need to rotate the source 10 as in the FIG. 15A embodiment.

Figure 16C:
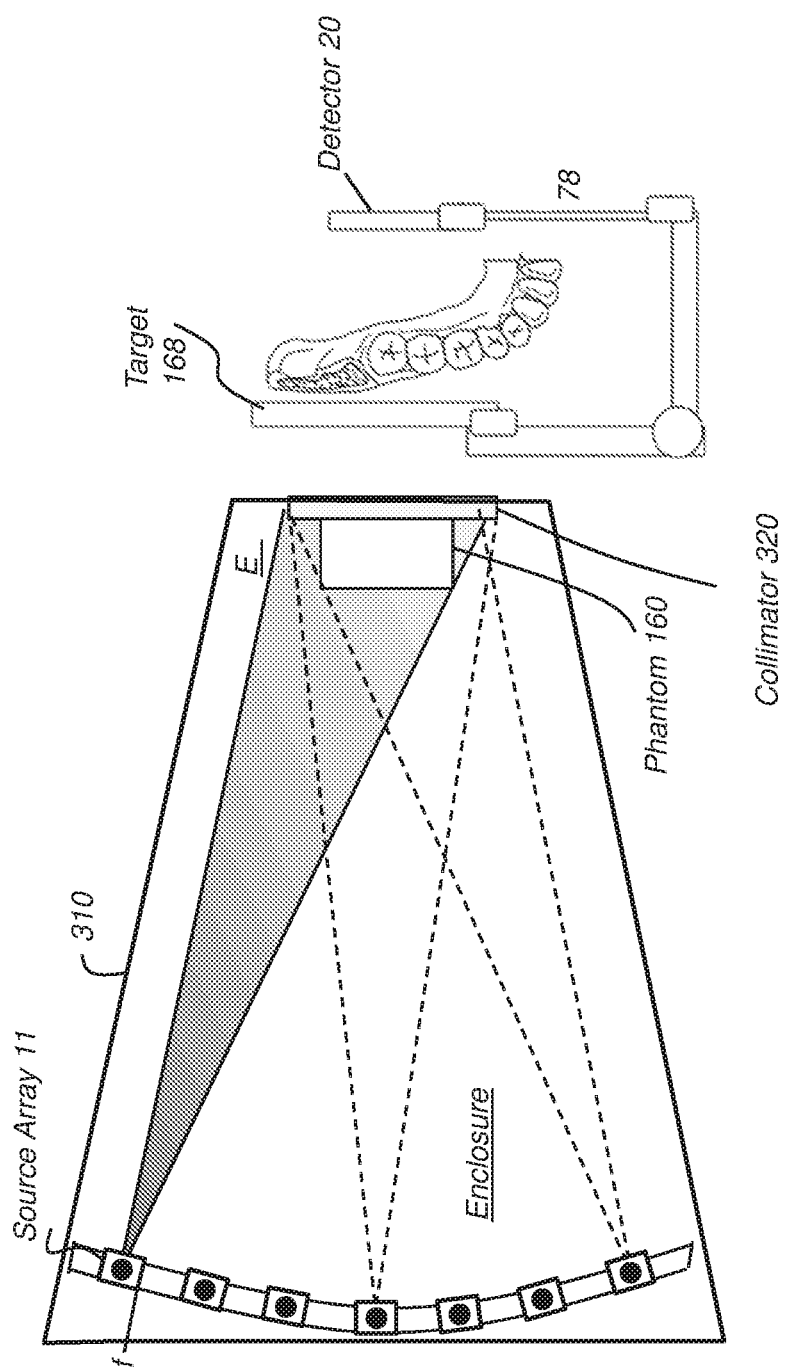
FIG. 16C is a schematic diagram that displays an intraoral apparatus for tomosynthesis imaging an x-ray source enclosure and a target frame coupled to a detector. The x-ray source enclosure includes a fixed collimator and an array of x-ray sources positioned in fixed location in an arc.

FIG. 16C shows an alternate example embodiment according to the present invention in which the array of stationary sources is arranged in a curved path so each source will emit towards the collimator 320 and avoid any mechanical actuator either at source or primary collimator. The x-ray source enclosure 310 uses target 168 to position the x-ray beam on the desired patient anatomy/detector combination.

Figure 16D:
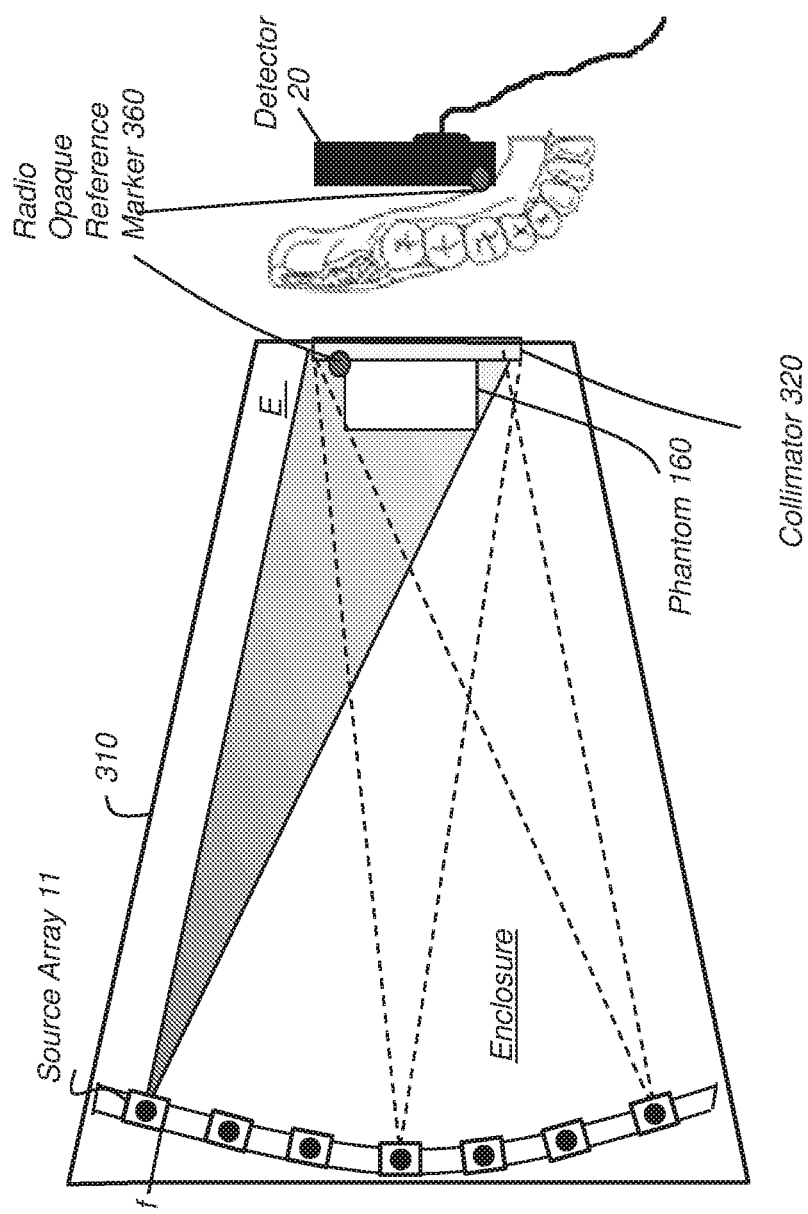
FIG. 16D is a schematic diagram that displays an intraoral apparatus for tomosynthesis imaging with an x-ray source enclosure and a detector without a target frame using radio-opaque reference markers to position an x-ray source with respect to the detector. The x-ray source enclosure includes a fixed collimator and an array of x-ray sources positioned in fixed location in an arc.

FIG. 16D shows an alternate example embodiment according to the present invention in which the array of stationary sources is arranged in a curved path so each source will emit towards the collimator 320 and avoid any mechanical actuator either at the source or primary collimator. The radio opaque reference markers 360 embedded in primary collimator 320 and detector 20 are used to automatically steer x-ray source enclosure 310 to accurate positions on the desired anatomy by detection of the reference marker shadows in the captured images.

Figure 16E:
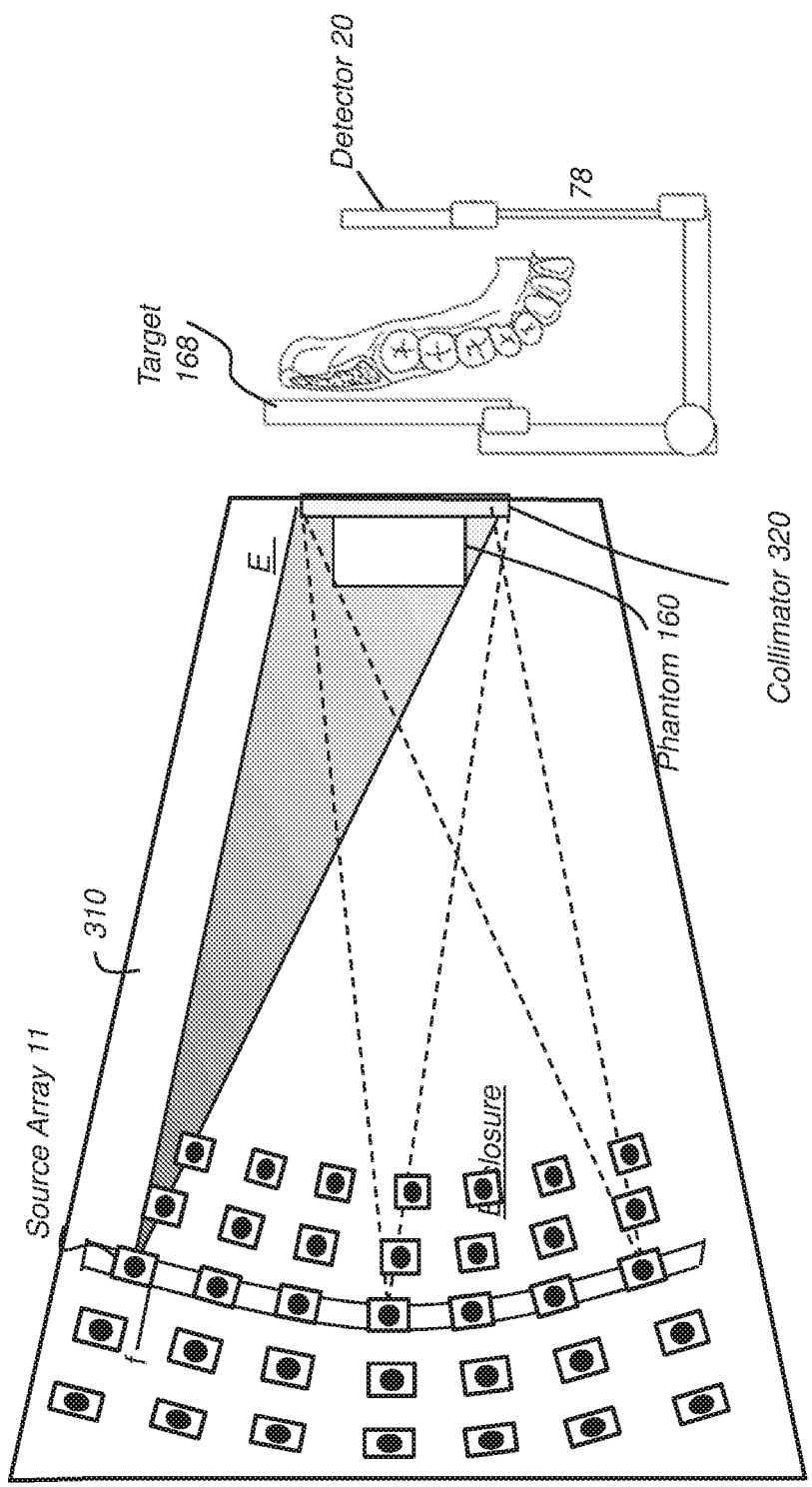
FIG. 16E is a schematic diagram that displays an intraoral apparatus for tomosynthesis imaging with an x-ray source enclosure and a target frame coupled to a detector. The x-ray source enclosure includes a fixed collimator and a 2-D array of x-ray sources arranged in a spherical shape.

FIG. 16E shows an alternate example embodiment according to the present invention in which a 2-D panel of stationary sources is arranged in a concave (spheroid) 2-D surface so each source is positioned to emit towards the collimator 320 and avoid any mechanical actuator either at the source or primary collimator. The x-ray source enclosure 310 uses target 168 to position the x-ray beam on the desired patient anatomy/detector combination.

Figure 16F:
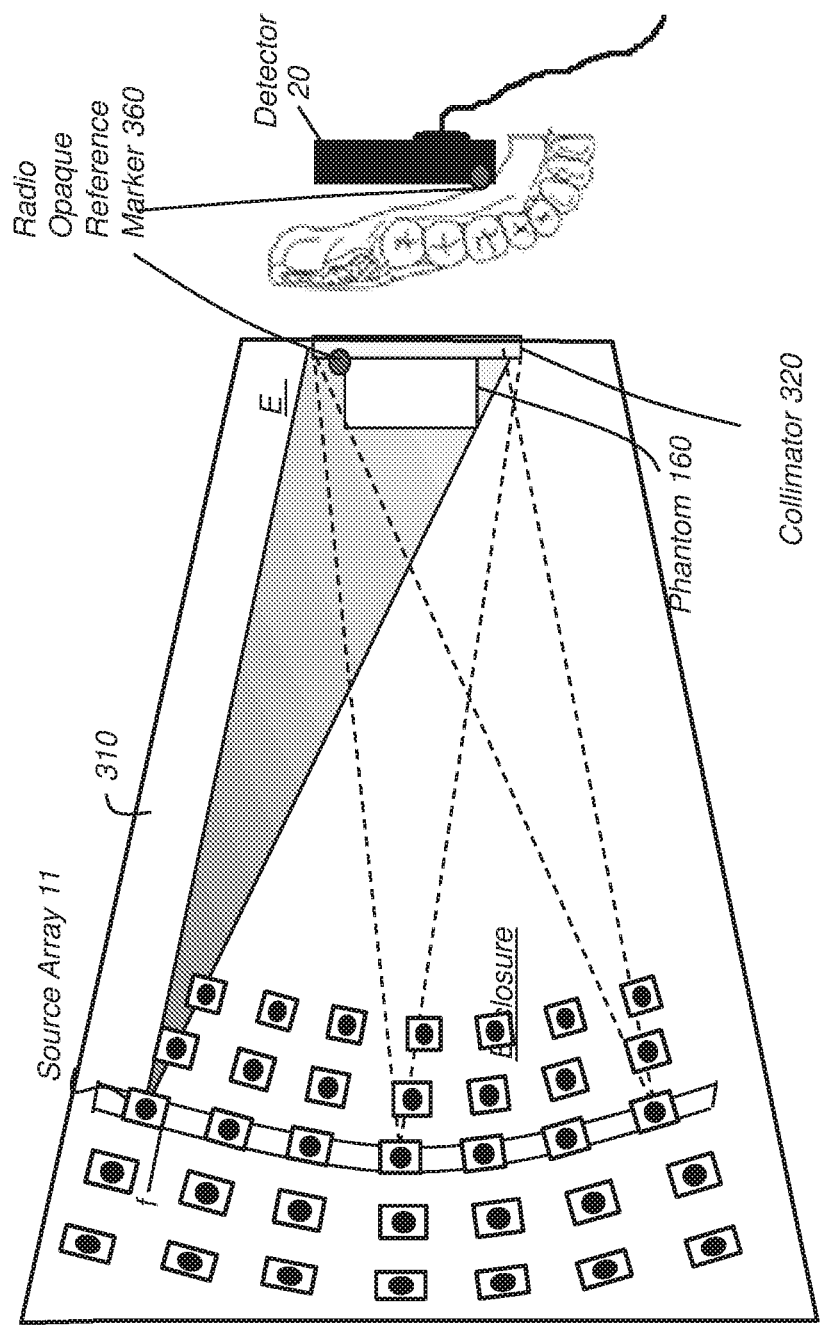
FIG. 16F is a schematic diagram that displays an intraoral apparatus for tomosynthesis imaging with an x-ray source enclosure and a detector without a target frame using radio-opaque reference markers to position an x-ray source with respect to the detector. The x-ray source enclosure includes a fixed collimator and a 2-D array of x-ray sources arranged in a spherical shape.

FIG. 16F shows an alternate example embodiment according to the present invention in which a 2-D panel of stationary sources is arranged in a concave (spheroid) 2-D surface so each source is positioned to emit towards the collimator 320 and avoid any mechanical actuator either at the source or primary collimator. The radio opaque reference markers 360 embedded in primary collimator 320 and detector 20 are used to automatically steer x-ray source enclosure 310 to accurate positions on the desired anatomy by detection of the reference marker shadows in the captured images.

Figure 17A:
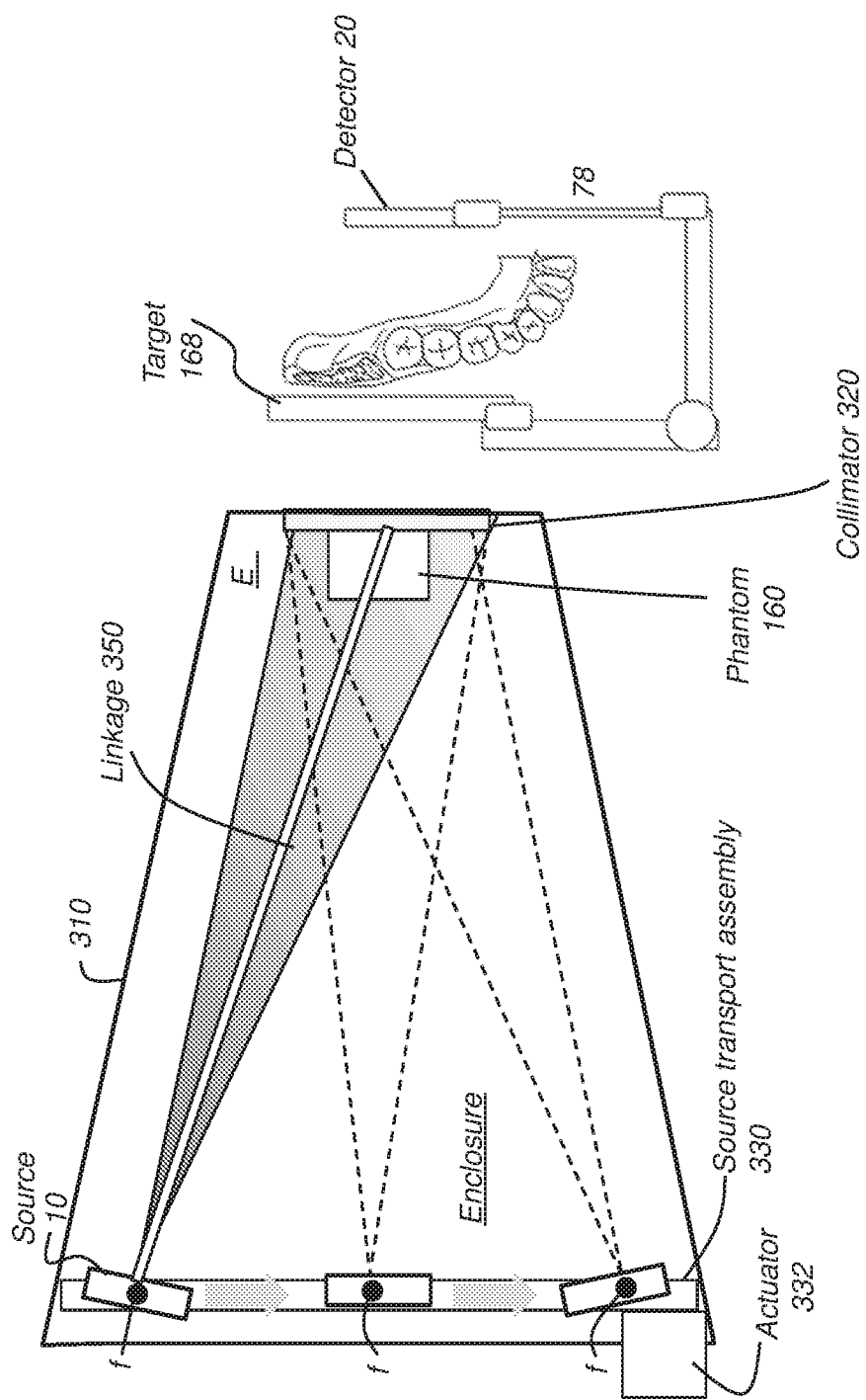
FIG. 17A is a schematic diagram that displays an intraoral apparatus for tomosynthesis imaging with an x-ray source enclosure and a target frame coupled to a detector. The x-ray source enclosure includes a single x-ray source and a linkage means for coordinated movement of a collimator window with respect to source position during imaging.
Figure 17B:
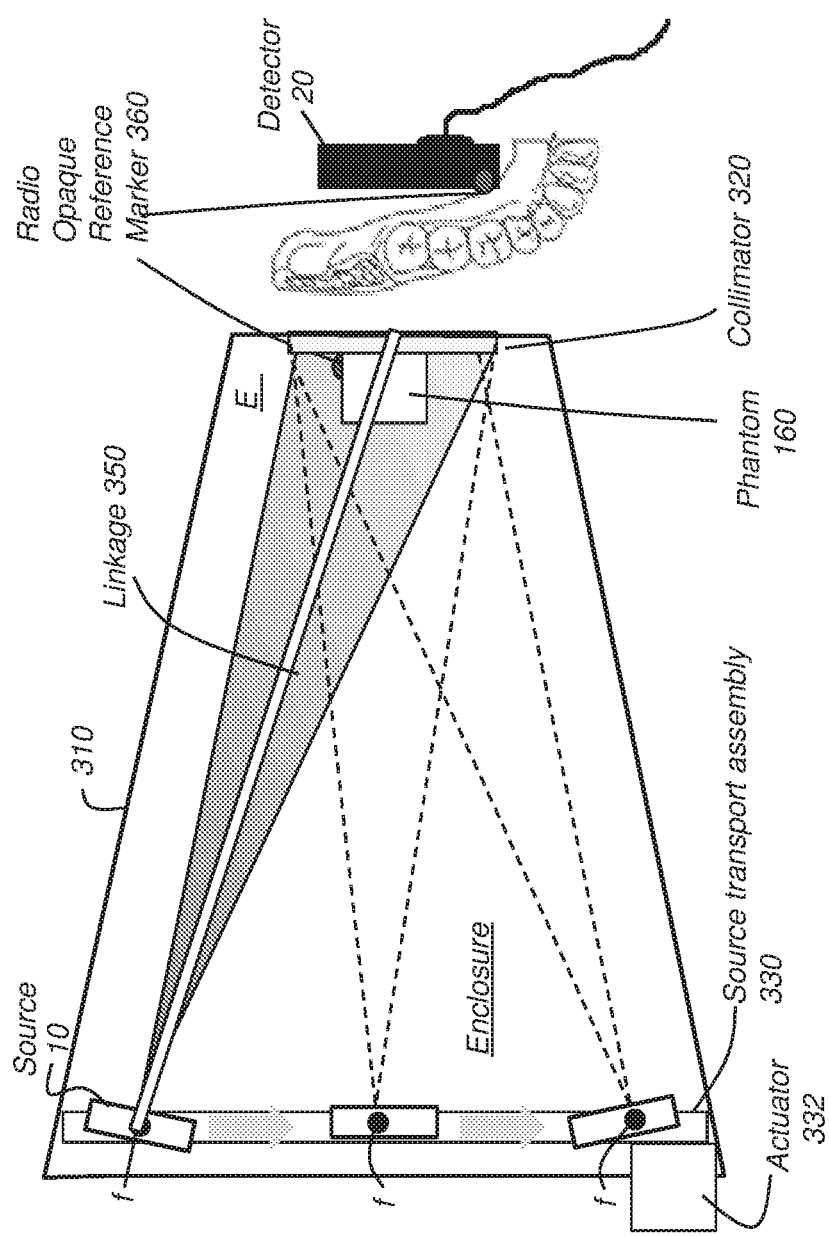
FIG. 17B is a schematic diagram that displays an intraoral apparatus for tomosynthesis imaging with an x-ray source enclosure and a detector without a target frame using radio-opaque reference markers to position an x-ray source with respect to the detector. The x-ray source enclosure includes a single x-ray source and a linkage means for coordinated movement of a collimator window with respect to source position during imaging.

FIG. 17A (frame coupled to detector) and FIG. 17B (radio opaque markers embedded in collimator and detector) show an alternate example embodiment according to the present invention in which a linkage 350 is provided for adjusting the collimator 320 in synchronization with the changing position of x-ray source 10. Coordination of movement by linkage 350 may use an arrangement of levers, gears, belts, or other devices, such that linkage 350 mechanically or otherwise couples source transport assembly 330 movement to the collimator 320 adjustment mechanism, as described in more detail below.

Figure 17C:
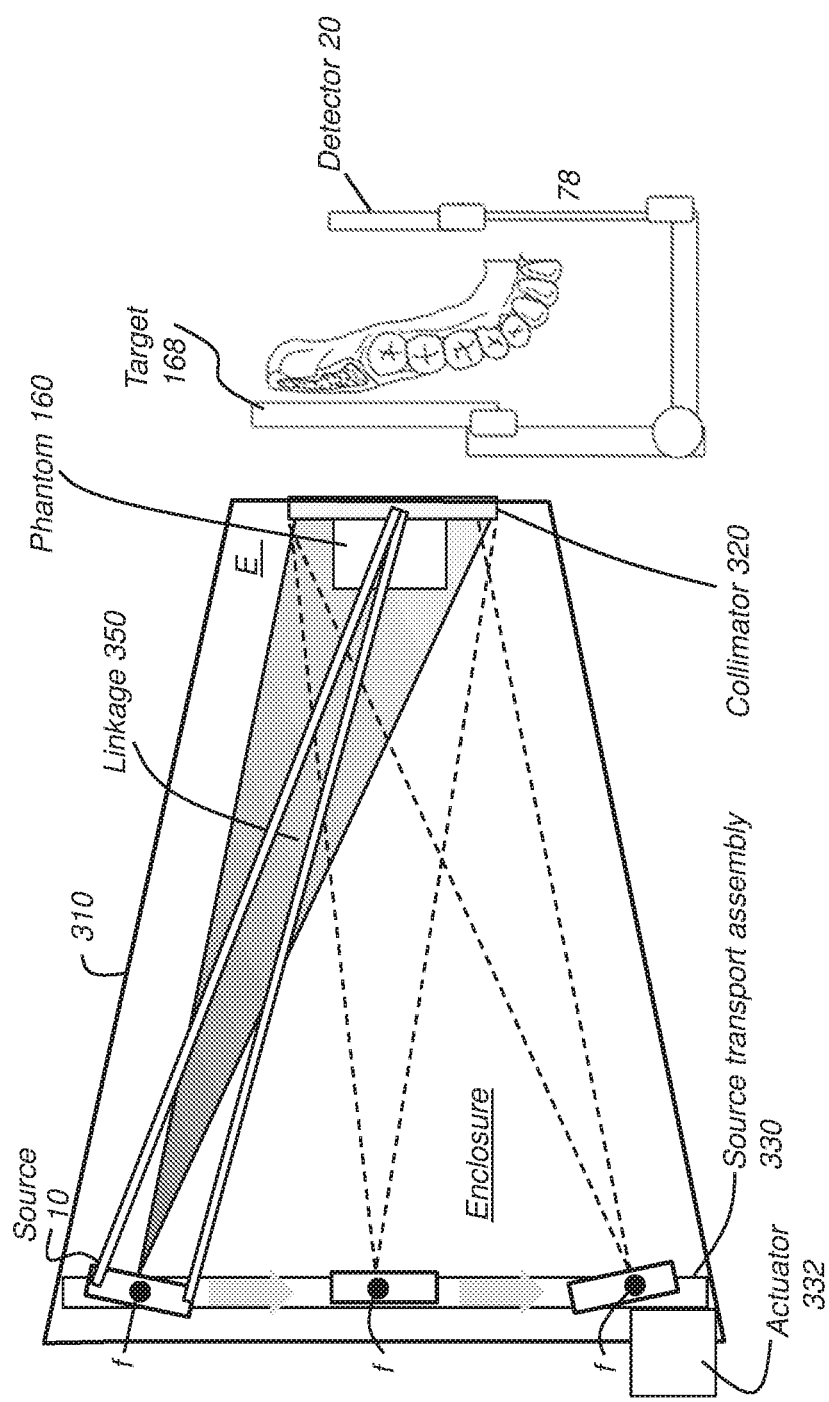
FIG. 17C is a schematic diagram that displays an intraoral apparatus for tomosynthesis imaging with an x-ray source enclosure and a target frame coupled to a detector. The x-ray source enclosure includes a single x-ray source and a linkage means between the source and a collimator window to provide coordinated rotation of the x-ray source by means of a pulley.
Figure 17D:
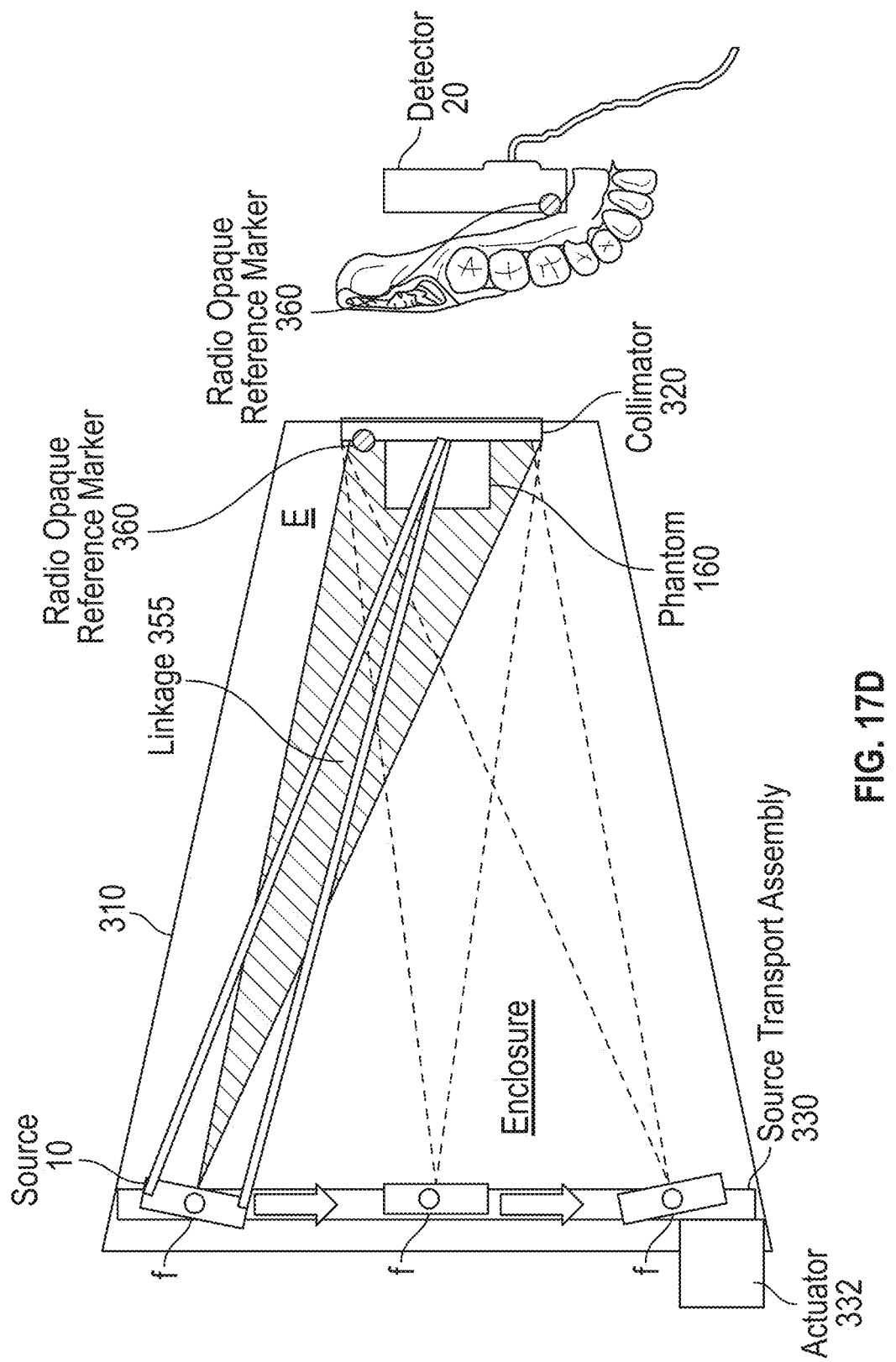
FIG. 17D is a schematic diagram that displays an intraoral apparatus for tomosynthesis imaging with an x-ray source enclosure and a detector without a target frame using radio-opaque reference markers to position an x-ray source with respect to the detector. The x-ray source enclosure includes a single x-ray source and a linkage means between the x-ray source and a collimator window to provide coordinated rotation of the x-ray source by means of a pulley.

FIG. 17C (frame coupled to detector) and FIG. 17D (radio opaque markers embedded in collimator and detector) show an alternate example embodiment according to the present invention in which a linkage pair 355 is provided for adjusting the collimator 320 in synchronization with the changing position of x-ray source 10 beside rotate the source to focus on collimator/detector, eliminating the need for collimator sliding. Coordination of movement by linkage 355 may use an arrangement of levers, gears, belts, or other devices, such that linkage 355 mechanically or otherwise couples source transport assembly 330 movement to the collimator 320 adjustment mechanism, as described in more detail below.

Sliding Collimator

Figure 18A:
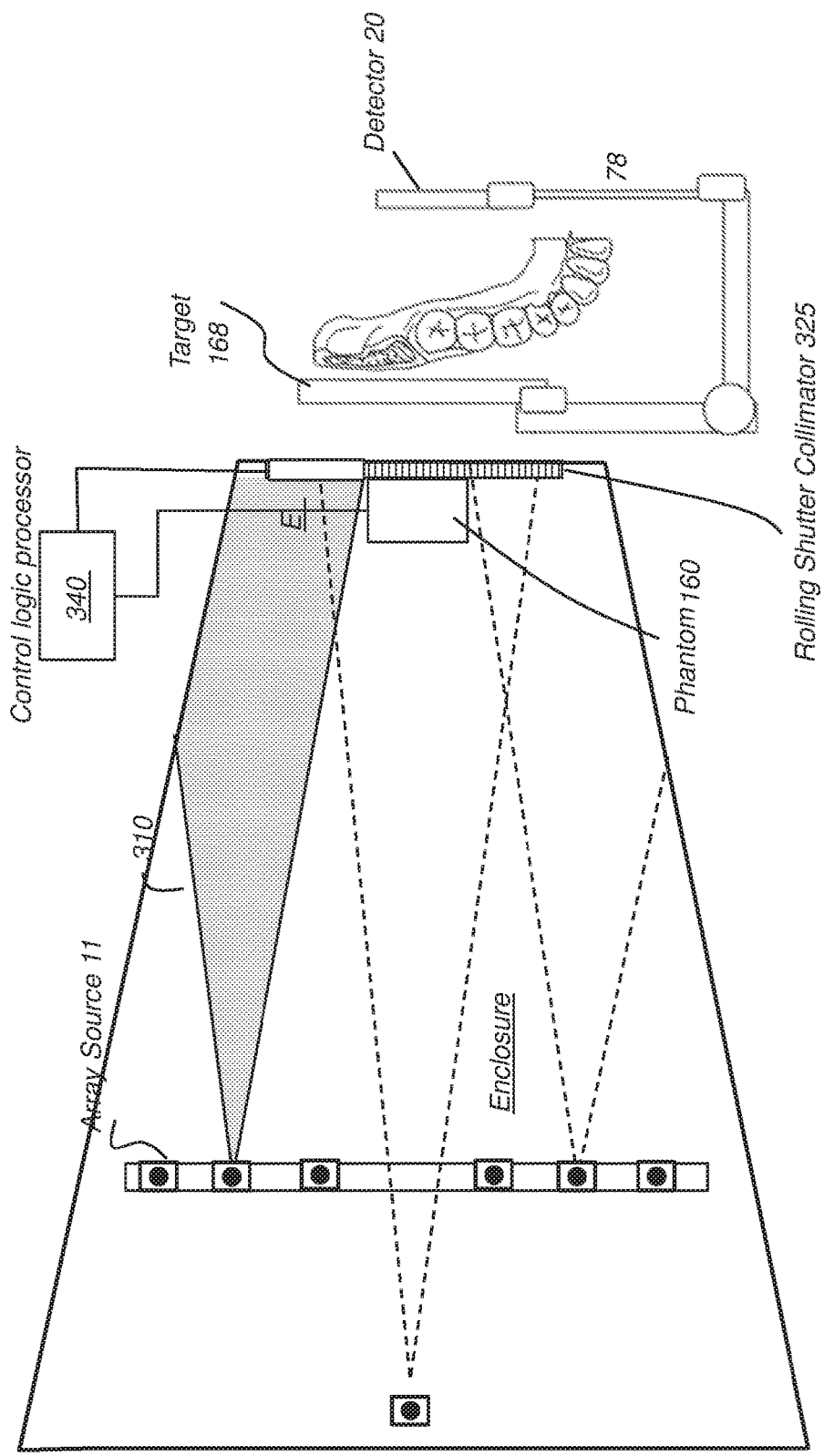
FIG. 18A is a schematic diagram that displays an intraoral apparatus for tomosynthesis imaging with an x-ray source enclosure and a target frame coupled to a detector. The x-ray source enclosure includes a high-dose central x-ray source at a different distance from an array of low dose x-ray sources in a linear configuration. The x-ray sources radiate the entire detector surface via a rolling shutter collimator while a phantom is displaced in and out of x-ray beam coverage to enable single image capture and perform tomosynthesis imaging with target frame or without target frame using radio-opaque reference. The high dose central source, individually operated without a phantom in the field of view, or phantom is mechanically moved during the capture, enable the regular intra-oral 2-D imaging option. This arrangement of mixing high dose, differently located source along with array of low dose sources enable both regular 2-D intraoral imaging as well as newer tomosynthesis volume imaging.
Figure 18B:
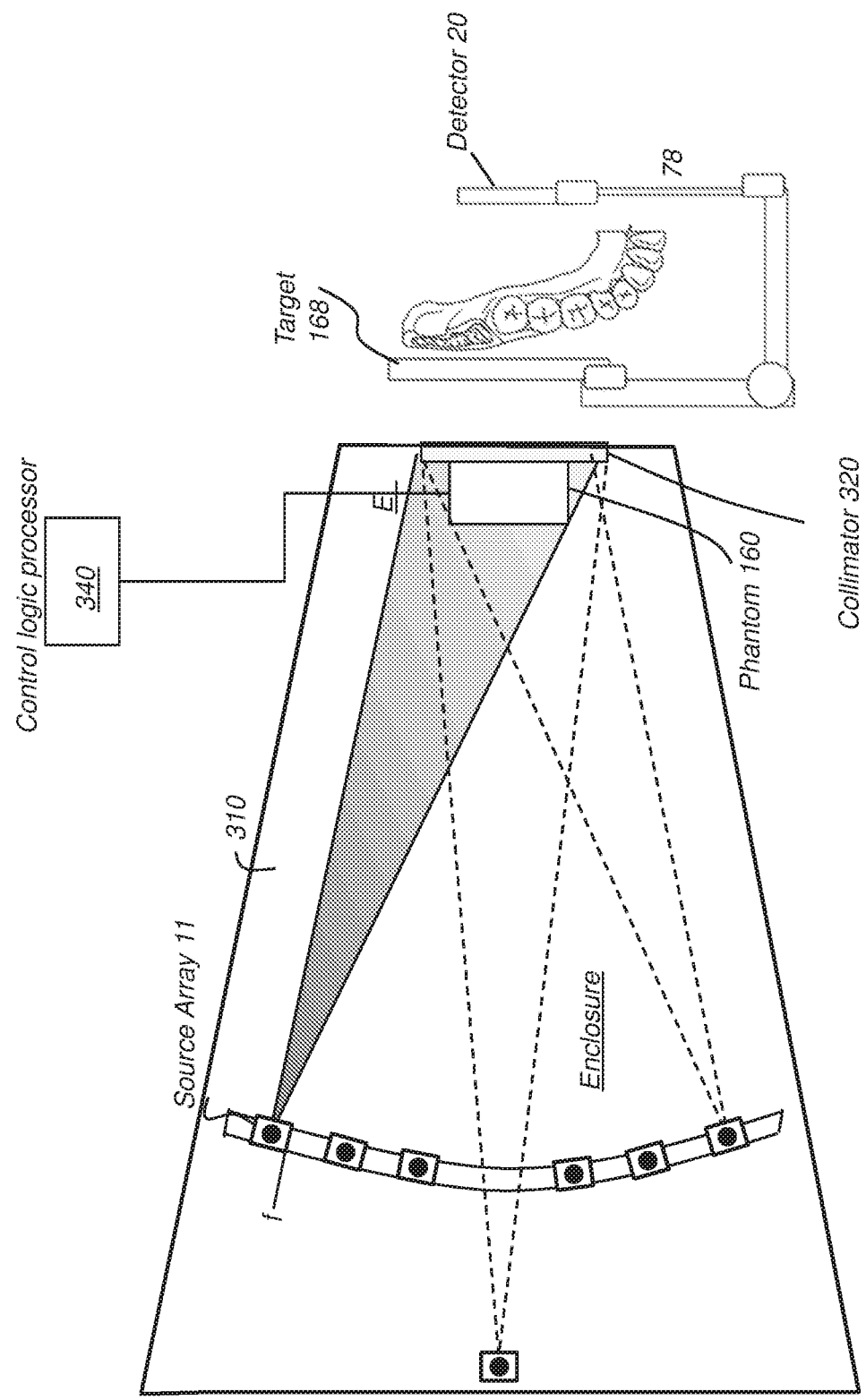
FIG. 18B is a schematic diagram that displays an intraoral apparatus for tomosynthesis imaging with an x-ray source enclosure and a target frame coupled to a detector. The x-ray source enclosure includes a high-dose central x-ray source at different distance from an array of x-ray sources positioned in a fixed location in an arc. The x-ray sources radiate the entire detector surface via a rolling shutter collimator while a phantom is displaced in and out of x-ray beam coverage to enable single image capture and tomosynthesis imaging. A high-power central x-ray source at different distance from rest of the x-ray sources in an arch path arrangement and radiate the entire detector surface via a fixed collimator while phantom is displaced in and out of x-ray beam coverage so to help regular intraoral single capture without phantom in the field as well as multiple projections with phantom in the field of view to do tomosynthesis and form tomosynthesis imaging with target frame or without target frame and use radio opaque reference.
Figure 18C:
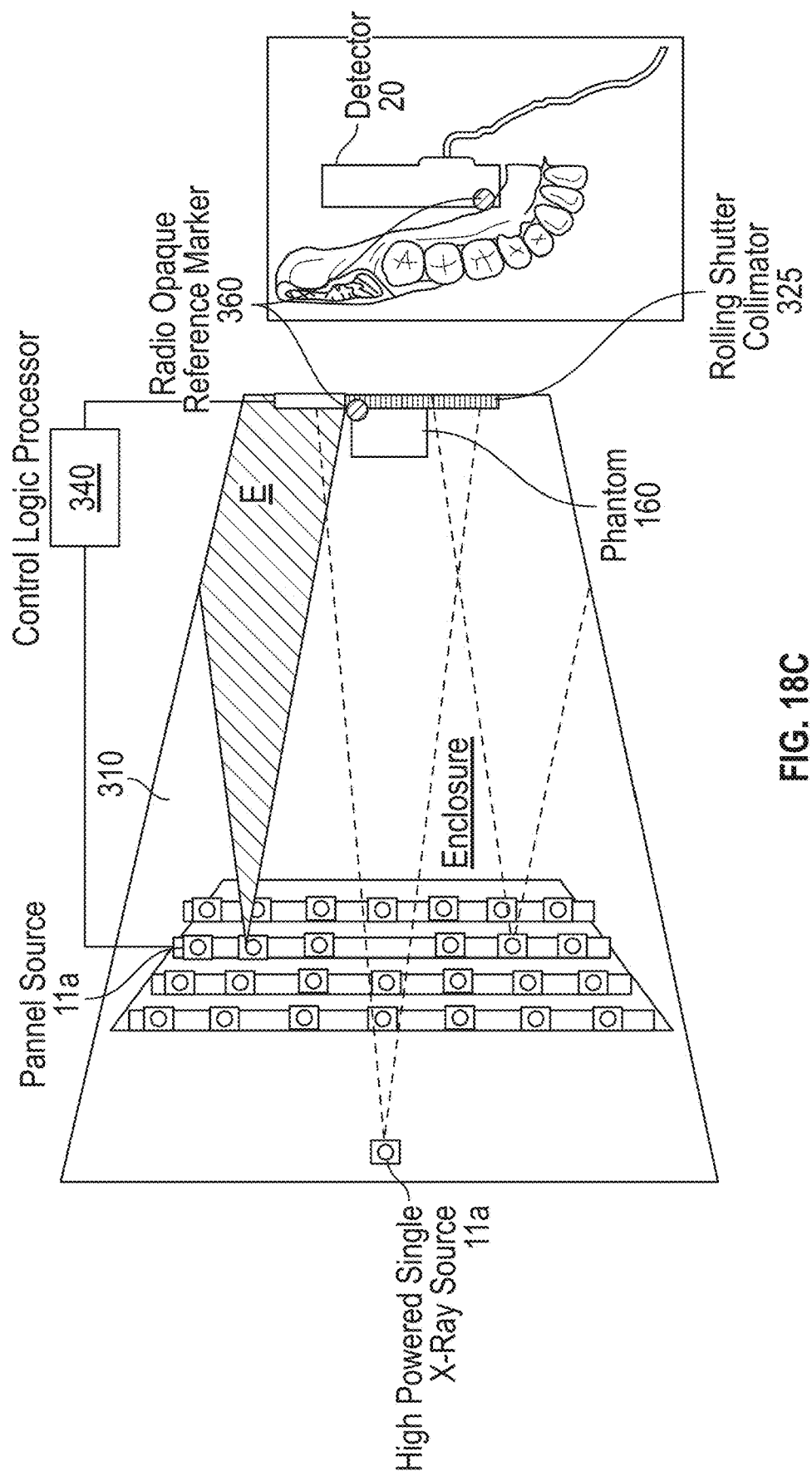
FIG. 18C is a schematic diagram that displays an intraoral apparatus for tomosynthesis imaging with an x-ray source enclosure and a target frame coupled to a detector. The x-ray source enclosure includes a high-dose central x-ray source at a different distance from a panel of low dose two-dimensional x-ray sources in a panel configuration and the x-ray sources radiate the entire detector surface via a rolling shutter collimator while a phantom is displaced in and out of x-ray beam coverage to enable single image capture and perform tomosynthesis imaging with target frame or without target frame using radio-opaque reference. The high dose central x-ray source, individually operated without a phantom in the field of view, or phantom is mechanically moved during the capture, enable the regular intraoral 2-D imaging option. This arrangement of mixing a high dose, differently located source along with array of low dose sources enables both regular 2-D intraoral imaging as well as newer tomosynthesis volume imaging.
Figure 18D:
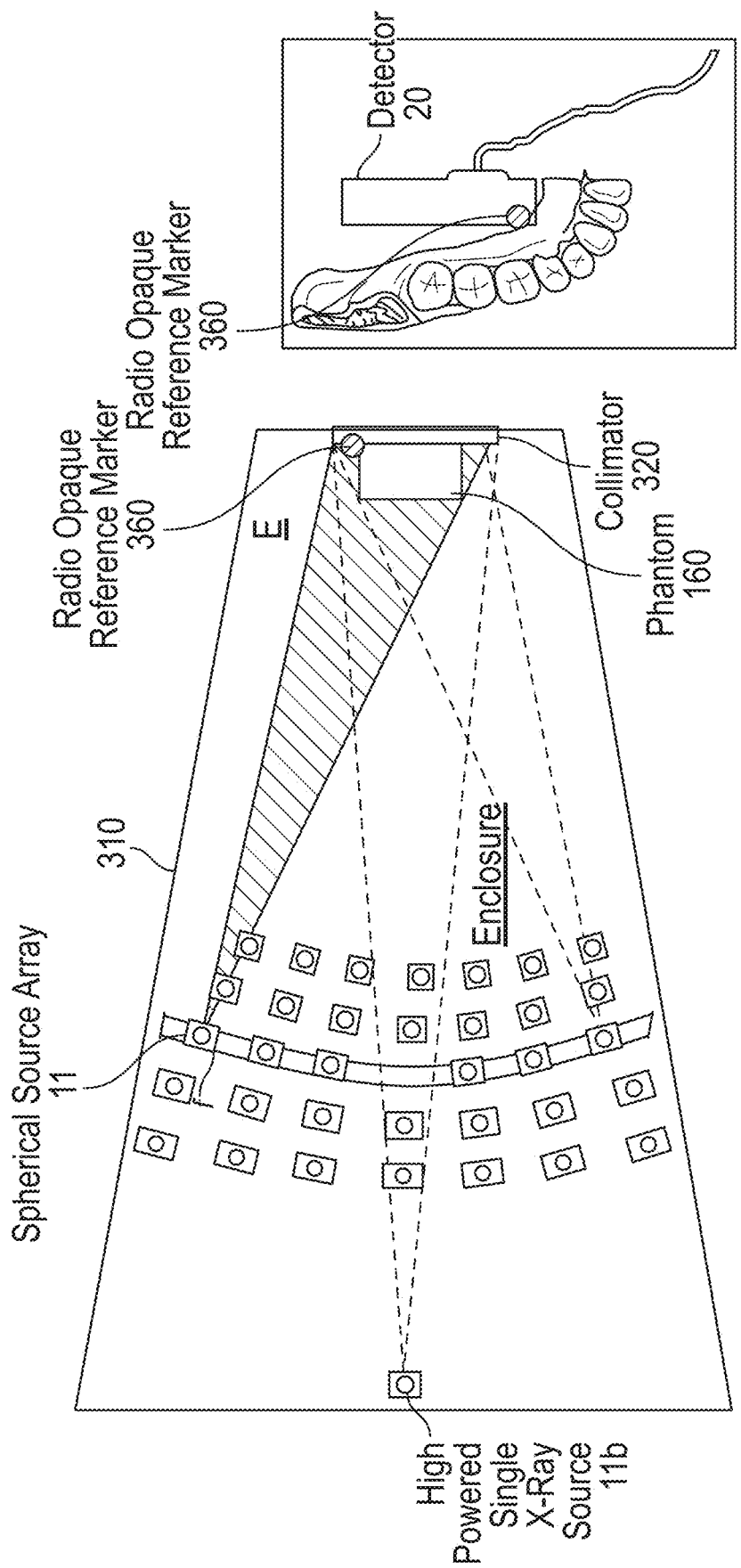
FIG. 18D is a schematic diagram that displays an intraoral apparatus for tomosynthesis imaging with an x-ray source enclosure and a target frame coupled to a detector. The x-ray source enclosure includes a high-dose central x-ray source at a different distance from a spherical panel of two-dimensional x-ray sources positioned in a fixed location in a spherical patch. The x-ray sources radiate the entire detector surface via a rolling shutter collimator while a phantom is displaced in and out of x-ray beam coverage to enable single image capture and tomosynthesis imaging. A high-power central x-ray source at a different distance from rest of the sources in an arch path arrangement radiates the entire detector surface via a fixed collimator while phantom is displaced in and out of x-ray beam coverage so to help regular intraoral single capture without phantom in the field as well as multiple projections with phantom in the field of view to do tomosynthesis and form tomosynthesis imaging with target frame or without target frame and use radio-opaque reference.

An example embodiment of the present invention addresses the problems of tomosynthesis geometry by providing collimator 320 as a sliding window or shutter that is moved into position to collimate radiation emitted at each focal point, f, position. The plan view of FIG. 18 shows adjustable collimator 320 that adapts the collimation to each source angle. A window 324 is configured to slide to an appropriate position along an axis, B, that is parallel to the plane of target aperture 168 and parallel to the linear travel path of the source 10 (FIG. 15, 17 embodiment). A slide mechanism 326 is actuable to translate window 324 along axis, B, in synchronization with the changing focal point, f. Geometric calibration phantom 160 is shown for reference; phantom 160 remains stationary as window 324 is shifted in position. The plan view of FIG. 18A shows the use of a rolling shutter collimator 325 and allows the aperture to slide while the aperture also holding phantom 160. This type of shutter collimator used in FIGS. 15B, 15C, 15D, 15E, 15F, and 15G example embodiments.

Figure 19A:
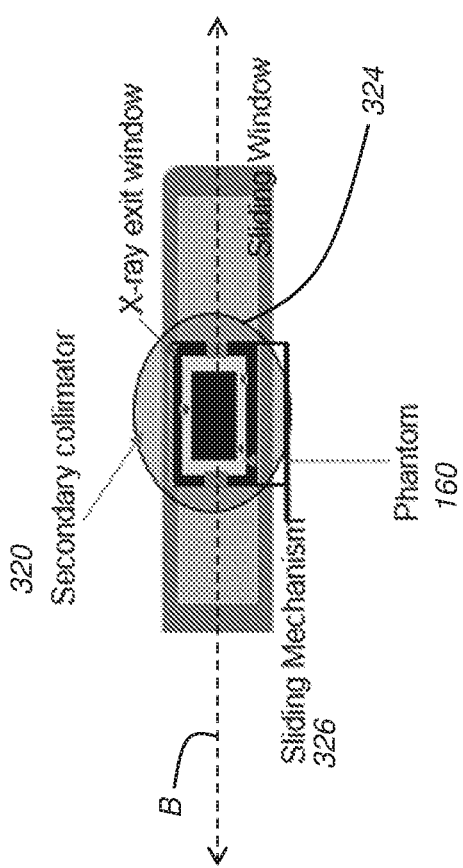
FIG. 19A is a plan view that displays a collimator with adjustable window.
Figure 19B:
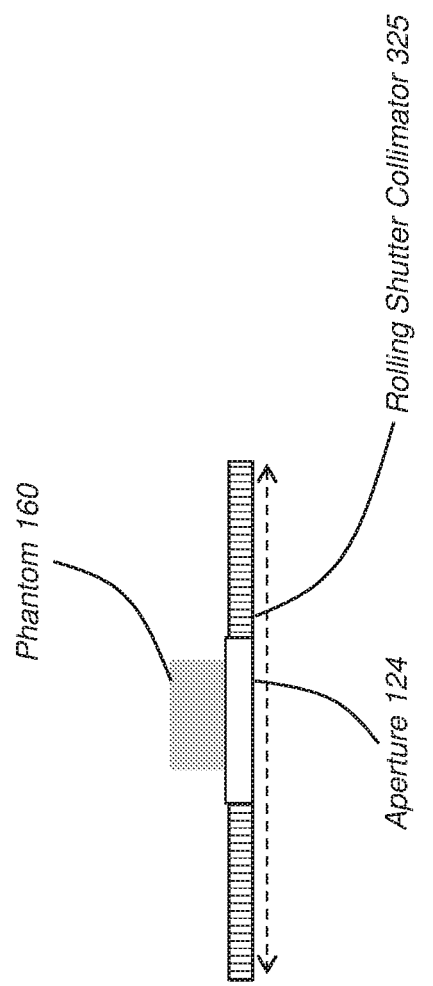
FIG. 19B is a plan view that displays a rolling shutter collimator providing sliding exit window.

FIGS. 19A and 19B show, in exaggerated form and not to scale, basic geometrical considerations for shifting window 324 according to the relative location of the emissive focal point, f. Window 324 movement helps to keep the emitted radiation directed through target aperture 168 and within the detector. It must be emphasized that source transport assembly 330 is optional. An array of sources may be used to provide sequential emission from each focal point, f, with corresponding movement of window 324 for collimation of the emitted radiation.

Window 324 may be shifted by any suitable mechanism, such as using a mechanical system, as described with reference to FIG. 17, or can be shifted by an actuator 328. Window 324 can alternately be provided by an electro-optical modulator that transmits or blocks radiation energy to provide appropriate collimation as described with reference to FIGS. 19A and 19B.

FIGS. 19C and 19D show, in exaggerated form and not to scale, basic geometrical considerations for rolling shutter collimation window 325 according to the relative location of the emissive focal point, f. Control logic processor 340 executes programmed instructions that control actuator 328 according to the position of the emitting focal point, f. A number of sensors (not shown) can be used to determine the respective positions of x-ray source 10 and window 324. Using the programmed control logic, translation and energizing of the radiation source can be synchronized with detected window 324 position. Control logic can trigger or delay exposure according to the relative movement progress and positions of window 324 at the target aperture 168 and source 10 along the source transport path.

The invention has been described in detail with particular reference to presently understood example embodiments, but it should be understood and appreciated that variations and modifications can be affected within the spirit and scope of the invention. For example, control logic processor 340 may be any of a number of types of logic processing device, including a computer or computer workstation, a dedicated host processor, a microprocessor, logic array, or other device, or combination of devices that execute stored program logic instructions. The presently disclosed example embodiments are, therefore, considered in all respects to be illustrative and not restrictive. The scope of the invention is indicated by the appended claims, and all changes that come within the meaning and range of equivalents thereof are intended to be embraced therein.

Consistent with at least one example embodiment, the example methods and apparatuses may use a computer program with stored instructions that perform on image data that is accessed from an electronic memory. As can be appreciated by those skilled in the image processing arts, a computer program of an example embodiment herein may be utilized by a suitable, general-purpose computer system, such as a personal computer or workstation. However, many other types of computer systems may be used to execute the computer program of described example embodiments, including an arrangement of one or networked processors, for example.

A computer program for performing methods of certain example embodiments described herein may be stored in a computer readable storage medium. This medium may comprise, for example; magnetic storage media such as a magnetic disk such as a hard drive or removable device or magnetic tape; optical storage media such as an optical disc, optical tape, or machine-readable optical encoding; solid state electronic storage devices such as random access memory (RAM), or read only memory (ROM); or any other physical device or medium employed to store a computer program. Computer programs for performing exemplary methods of described embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, may refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that can be directly associated with a display device and is periodically refreshed as needed in order to provide displayed data. This temporary storage buffer can also be considered to be a memory, as the term is used in the application. Memory is also used as the data workspace for executing and storing intermediate and final results of calculations and other processing. Computer-accessible memory can be volatile, non-volatile, or a hybrid combination of volatile and non-volatile types.

It should be understood and appreciated that computer program products for the example embodiments herein may make use of various image manipulation algorithms and/or processes that are well known. It should be further understood and appreciated that example computer program product embodiments herein may embody algorithms and/or processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the application, are not specifically shown or described herein and may be selected from such algorithms, systems, hardware, components and elements known in the art.

It should be still further understood and appreciated that example embodiments according to the present invention may include various features described herein (individually or in combination).

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations or example embodiments, such feature can be combined with one or more other features of the other implementations or example embodiments as can be desired and advantageous for any given or particular function. The term "about" indicates that the value listed can be somewhat altered, as long as the alteration does not result in nonconformance of the process or structure to the illustrated example embodiment. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An intraoral imaging apparatus for tomosynthesis imaging comprising:
    (a) an intraoral detector that is coupled to a frame, wherein the frame defines a target aperture for an incident radiation beam; and
    (b) an enclosure that is configured to seat against the target aperture, wherein the enclosure houses:
        (i) at least one x-ray source that is configured to emit a radiation beam from each of a plurality of focal points within the enclosure;
        (ii) a collimator, having a static, movable or rolling shutter aperture, that is disposed to form a collimated radiation beam from the emitted radiation beam and direct the collimated radiation beam through the target aperture and to the detector as the incident radiation beam; and
        (iii) a geometric calibration phantom having a plurality of radio-opaque markers and located in the path of the collimated radiation beam.

2. The apparatus of claim 1, wherein the at least one x-ray source is a linear array, radial array, rectilinear patch panel, or concave spherical patch panel of x-ray sources that are individually energizable to provide the radiation beam from each of the plurality of focal points in sequence.

3. The apparatus of claim 1, wherein the apparatus further comprises a source transport assembly that translates the position of the at least one x-ray source along a transport path within the enclosure.

4. The apparatus of claim 3 wherein the collimator has a collimator aperture and a collimator translation apparatus, and wherein the collimator translation apparatus translates the collimator in synchronization with emission from each of the plurality of focal points to position the collimator aperture with respect to the target aperture.

5. The apparatus of claim 4 wherein the collimator translation apparatus is mechanically coupled to the source transport assembly.

6. The apparatus of claim 4 further comprising a control logic processor that is configured to execute programmed instructions for driving the collimator translation apparatus in synchronization with emission from each of the plurality of focal points.

7. The apparatus of claim 1, wherein the enclosure aligns mechanically or magnetically to the frame.

8. The apparatus of claim 1, wherein the collimator has a static collimator aperture forming a collimated radiation beam large enough to irradiate the detector surface but avoid any radiation exposure to tissues surrounding the detector area.

9. The apparatus of claim 1 wherein the collimator comprises a rolling shutter collimator aperture operated by electro-mechanical means to open/roll the collimator aperture to allow emission from each of the plurality of focal points.

10. The apparatus of claim 1 wherein the markers of the plurality of radio-opaque markers are formed from radio-opaque materials having atomic numbers not exceeding 80.

11. The apparatus of claim 10 wherein the markers of the plurality of radio-opaque markers are taken from the group consisting of chromium steel, ceramic, tungsten carbide, and gold.

12. The apparatus of claim 10 wherein the markers of the plurality of radio-opaque markers are formed of a ceramic.

13. The apparatus of claim 1 wherein the markers of the plurality of radio-opaque markers are arranged in first and second parallel layers.

14. An intraoral imaging apparatus for tomosynthesis imaging comprising:
    (a) an intraoral detector having a radio-opaque marker embedded in a margin of an imaging area for intercepting an incident radiation beam, the intraoral detector being configured to be placed inside a patient's mouth without attachment to any extraoral target frame;
    (b) an enclosure that is configured for positioning proximate to the patient's face, without requiring contact with the patient's face, wherein the enclosure houses:

(i) at least one x-ray source that is configured to emit a radiation beam from each of a plurality of focal points within the enclosure;

(ii) a collimator having a static, movable or rolling shutter aperture, that is disposed to form a collimated beam from the emitted radiation beam and direct the collimated radiation beam to the detector as the incident radiation beam;

(iii) a geometric calibration phantom having a plurality of radio-opaque markers and displaceably positionable in the path of the collimated beam; and (iv) a radio-opaque marker embedded into the collimator in the path of x-ray beam to detector.

15. The apparatus of claim 14 wherein emission of the radiation beam is triggered when the collimator is in a suitable position.

16. The apparatus of claim 14 wherein the geometric calibration phantom is displaced into the path of the collimated radiation beam during acquisition with the detector of a projection image for tomosynthesis imaging.

17. The apparatus of claim 14 further comprising a control logic processor that is configured to execute programmed instructions for detecting radio-opaque marker shadows in an image captured by the detector and steering the enclosure to a predetermined positional geometry with respect to the detector based on such detected marker shadows.

18. The apparatus of claim 14 further comprising a control logic processor that is configured to execute programmed instructions for performing a geometry recovery method for source-to-detector geometry using the radio-opaque markers of the collimator and detector and resultant image features of images captured by the detector without using the geometric calibration phantom.

19. An intraoral imaging apparatus for tomosynthesis imaging comprising:

(a) an intraoral detector that is coupled to a frame, wherein the frame defines a target aperture for an incident radiation beam; or an intraoral detector having a radio-opaque marker embedded in a margin of an imaging area for intercepting an incident radiation beam, the intraoral detector being configured to be placed inside a patient's mouth without attachment to any target frame;

(b) an enclosure that is configured for positioning proximate to the patient's face, wherein the enclosure houses:

(i) a linear array, radial array, rectilinear patch panel, or concave spherical patch panel of x-ray sources configured to emit a radiation beam from each of a plurality of focal points;

(ii) a collimator that is disposed to form a collimated beam from the emitted radiation beam and direct the collimated radiation beam to the detector as the incident radiation beam;

(iii) a geometric calibration phantom having a plurality of radio-opaque markers and displaceably positionable in the path of the collimated beam for tomosynthesis capture; and (iv) a central x-ray source of higher power than, and positioned at a different source-to-detector distance than, said array or patch panel x-ray sources, for non-tomosynthesis, 2D intra-oral image capture, wherein the geometric calibration phantom is displaced out of the path of the collimated beam for said non-tomosynthesis, 2D intra-oral image capture.

20. The apparatus of claim 19 wherein the array or patch panel x-ray sources comprises stationary carbon nanotube emissive components.

21. The apparatus of claim 19 further comprising a control logic processor that is configured to execute programmed instructions for displacing the geometric calibration phantom mechanically out of the path of the collimated beam for said non-tomosynthesis, 2D intra-oral image capture.

22. The apparatus of claim 19 wherein the collimator has a collimator aperture and a collimator translation apparatus, and wherein the collimator translation apparatus translates the collimator in synchronization with emission from each of the plurality of focal points to position the collimator aperture with respect to the detector.

23. The apparatus of claim 22 further comprising a control logic processor that is configured to execute programmed instructions for driving the collimator translation apparatus in synchronization with emission from each of the plurality of focal points.

* * * * *